United States Patent [19]

Klee et al.

[11] Patent Number: 5,512,466
[45] Date of Patent: Apr. 30, 1996

[54] CONTROL OF FRUIT RIPENING AND SENESCENCE IN PLANTS

[75] Inventors: Harry J. Klee, Ballwin; Ganesh M. Kishore, Chesterfield, both of Mo.

[73] Assignee: Monsanto Company, St. Louis, Mo.

[21] Appl. No.: 809,457

[22] Filed: Dec. 17, 1991

Related U.S. Application Data

[63] Continuation-in-part of Ser. No. 632,440, Dec. 26, 1990, abandoned.

[51] Int. Cl.$^6$ .......................... A12N 15/31; A12N 15/63; A12N 15/82; C01H 5/08
[52] U.S. Cl. .................... 435/172.3; 435/320.1; 435/69.1; 435/70.1; 536/23.2; 800/205; 800/200; 800/DIG. 44
[58] Field of Search ..................................... 800/200, 205, 800/DIG. 44; 435/172.3, 320.1, 69.1, 70.1; 536/23.2

[56] References Cited

U.S. PATENT DOCUMENTS

| | | | |
|---|---|---|---|
| 4,801,540 | 1/1989 | Hiatt et al. | 435/172.3 |
| 4,843,186 | 6/1989 | Nabum | 800/200 |
| 4,943,674 | 7/1990 | Houck et al. | 800/205 |

FOREIGN PATENT DOCUMENTS

| | | |
|---|---|---|
| 0271988 | 6/1988 | European Pat. Off. . |
| 0409625 | 1/1991 | European Pat. Off. . |
| WO91/01375 | 2/1991 | WIPO . |
| WO91/09112 | 6/1991 | WIPO . |
| WO91/16417 | 10/1991 | WIPO . |

OTHER PUBLICATIONS

Barton et al., *Plant Physiology*, 85: 1103–1109 (1987).
Bouzayen et al., *Planta*, 180: 175–180 (1990).
Christoffersen et al., *Planta*, 155:52–57 (1982).
Hamilton et al., *Nature*, 346: 284–287 (1990).
Honma et al., *Agric. Biol. Chem.*, 42(10): 1825–1831 (1978).
Kende, *Plant Physiology*, 91:1–4 (1989).
Lizada et al., *Analytical Biochemistry*, 100:140–145 (1979).
McGarvey et al., *Plant Mol. Biol.*, 15: 165–167 (1990).
Slater et al., *Plant Mol. Biol.*, 5: 137–147 (1985).
Vacek et al., *Nature*, 328: 33–37 (1987).
Yang, S. F., et al. Ann. Rev. Plant Physiol., vol. 35 (1984) pp. 155–189.
Walsh, C., et al. Biochem., vol. 20 (1981) pp. 7509–7519.
Aebersold, R., et al. Proc. Nat. Acad. Sci., vol. 84 (1987) pp. 6970–6974.
Jaye, H., et al. Nucl. Acids Res., vol. 11 (1983) pp. 2325–2335.
McCormick, S., et al. Plant Cell Reports, vol. 5 (1986) pp. 81–84.
Devlin, R. *Plant Physiology*, 3rd Ed. N.Y., N.Y., D. van Nostrand Co., 1975, pp. 436 & 507–508.
Deikman, J., et al. EMBO Journal, vol. 7 (1988) pp. 3315–3320.
Sanger, M. et al. Plant Mol. Biol., vol. 14, (1990) pp. 433–443.
Sanders, P. R. Nucl. Acids Res., vol. 15 (1987) pp. 1543–1558.
Harpster, M. H. Mol. Gen. Genet, vol. 212 (1988) pp. 182–190.
E. Shahin, "Isolation and Culture of Protoplasts: Tomato", in Cell Culture and Somatic Cell Genetics of Plants, vol. 1, (1984) Academic Press, NY, pp. 370–380.

*Primary Examiner*—David T. Fox
*Assistant Examiner*—Charles Rories
*Attorney, Agent, or Firm*—Grace L. Bonner; Dennis R. Hoerner, Jr.; Richard H. Shear

[57] ABSTRACT

A method for controlling the ripening of fruits and vegetables as well as a method for controlling senescence of plant tissue is described. The method generally embraces the expression of an ACC metabolizing enzyme in the fruit or other desired plant tissue to inhibit the production of ethylene in the fruit or plant tissue. The use of the ACC metabolizing enzyme ACC deaminase is described in detail. The ripening or senescence process in the fruit or plant tissue is inhibited by the expression of the ACC deaminase gene such that the shelf-life and marketability of the fruit or plant is enhanced. The ACC metabolizing enzyme may be used in combination with other methods for reducing ethylene production in transformed plants to further reduce the production of ethylene in the fruit or plant. DNA constructs containing the ACC deaminase gene are also described.

28 Claims, 25 Drawing Sheets

| Strain | Number of Isolates Tested |
|---|---|
| *Pseudomonas putida* biovar A | 58 |
| *Pseudomonas putida* biovar B | 23 |
| *Pseudomonas chlororaphis* | 170 |
| *Pseudomonas tolaasii* | 41 |
| *Pseudomonas aureofaciens* | 28 |
| *Pseudomonas corrugata* | 13 |
| *Pseudomonas fragi* | 18 |
| *Pseudomonas marginalis* | 1 |
| *Pseudomonas syringae* (multiple pathovars) | 93 |
| *Pseudomonas fluorescens* A | 4 |
| *Pseudomonas fluorescens* B | 5 |
| *Pseudomonas fluorescens* C (Inc.ATCC 10844) | 12 |
| *Pseudomonas fluorescens* G (Inc.ATCC 13524) | 14 |
| *Pseudomonas coronafaciens* | 3 |
| *Pseudomonas aeruginosa* (Inc.ATCC 15526) | 9 |
| fluorescent pseudomonads (incomplete identification) | 61 |
| *Pseudomonas mendocina* | 1 |
| *Pseudomonas stutzeri* | 1 |
| *Pseudomonas alcaligenes* | 1 |
| *Pseudomonas testosteroni* (Inc.ATCC 17409, 17510, 11996) | 7 |
| *Pseudomonas cepacia* ATCC 10856 | 1 |
| *Pseudomonas delafieldii* ATCC 17505 | 1 |
| *Pseudomonas diminuta* ATCC 11568 | 1 |
| *Pseudomonas acidovorans* | 3 |
| *Pseudomonas cruciuriae* ATCC 13262 | 1 |
| *Pseudomonas methanolica* ATCC 21704 | 1 |
| *Pseudomonas pickettii* ATCC 27511 | 1 |
| *Pseudomonas vesicularis* ATCC 11426 | 1 |
| *Xanthomonas maltophilia* ATCC 13637 | 2 |
| *Agrobacterium tumefaciens* | 3 |
| *Erwinia herbicola* | 1 |
| *Enterobacter cloacae* ATCC 13047 | 1 |
| *Enterobacter aerogenes* ATCC 13048 | 1 |
| *Hafnia alvei* | 2 |
| non-fluorescent (incomplete identification) | 11 |
| *Bacillus thuringiensis* | 1 |
| *Bacillus licheniformis* | 1 |
| *Corynebacterium fascians* | 41 |

FIGURE 1

```
   1  GATATCCCATATCAAGGAGCAGAGTCATGAATCTGAATCGTTTTGAACGTTATCCATTGACC
                                  MetAsnLeuAsnArgPheGluArgTyrProLeuThr

63  TTCGGTCCTTCTCCCATCACGCCCTTGAAGCGCCTCAGTCAACATCTGGGGGCAAGGTCGA
      PheGlyProSerProIleThrProLeuLysArgLeuSerGlnHisLeuGlyGlyLysValGl

125  GCTGTATGCCAAACGTGAAGACTGCAACAGTGGCCTGGCCTTTGGTGGGAACAAGACGCGCA
      uLeuTyrAlaLysArgGluAspCysAsnSerGlyLeuAlaPheGlyGlyAsnLysThrArgL

187  AGCTCGAATACCTCATTCCCGAAGCGATCGAGCAAGGCTGCGATACGCTGGTTTCCATCGGC
      ysLeuGluTyrLeuIleProGluAlaIleGlnGlyCysAspThrLeuValSerIleGly

249  GGCATCCAGTCGAACCAGACCCGTCAGGTCGCTGCCGTCGCTGCCCACTTGGGCATGAAGTG
      GlyIleGlnSerAsnGlnThrArgGlnValAlaAlaValAlaAlaHisLeuGlyMetLysCy

311  CGTGTTGGTGCAGGAAAACTGGGTGAACTATTCCGACGCGGTGTATGACCGCGTAGGCAACA
      sValLeuValGlnGluAsnTrpValAsnTyrSerAspAlaValTyrAspArgValGlyAsnI

373  TCGAGATGTCGCGGATCATGGGCGCTGATGTGCGGCTTGACGCCGCTGGCTTCGATATTGGC
      leGluMetSerArgIleMetGlyAlaAspValArgLeuAspAlaAlaGlyPheAspIleGly

435  ATTCGGCCAAGTTGGGAAAAGGCCATGAGCGATGTCGTGGAACAGGGTGGCAAACCGTTTCC
      IleArgProSerTrpGluLysAlaMetSerAspValValGluGlnGlyGlyLysProPhePr

497  GATTCCAGCGGGTTGCTCCGAGCATCCCTATGGCGGCCTCGGTTTCGTCGGCTTTGCCGAAG
      oIleProAlaGlyCysSerGluHisProTyrGlyGlyLeuGlyPheValGlyPheAlaGluG

559  AGGTGCGGCAGCAGGAAAAGGAACTGGGCTTCAAGTTTGACTACATCGTGGTCTGCTCGGTG
      luValArgGlnGlnGluLysGluLeuGlyPheLysPheAspTyrIleValValCysSerVal

621  ACCGGCAGTACGCAGGCGGGCATGGTTGTTGGTTTCGCGGCTGACGGTCGTTCGAAGAATGT
      ThrGlySerThrGlnAlaGlyMetValValGlyPheAlaAlaAspGlyArgSerLysAsnVa

683  GATTGGTATCGATGCTTCGGCCAAGCCGGAACAGACCAAGGCACAGATCCTGCGCATCGCCC
      lIleGlyIleAspAlaSerAlaLysProGluGlnThrLysAlaGlnIleLeuArgIleAlaA

745  GACACACCGCTGAGTTGGTGGAGTTGGGGCGCGAGATTACGGAAGAGGACGTGGTGCTCGAT
      rgHisThrAlaGluLeuValGluLeuGlyArgGluIleThrGluGluAspValValLeuAsp

807  ACGCGTTTTGCCTACCCGGAATATGGCTTGCCCAACGAAGGCACATTGGAAGCCATCCGACT
      ThrArgPheAlaTyrProGluTyrGlyLeuProAsnGluGlyThrLeuGluAlaIleArgLe

869  GTGCGGCAGCCTTGAAGGCGTGCTGACAGACCCGGTATATGAAGGTAAATCGATGCACGGCA
      uCysGlySerLeuGluGlyValLeuThrAspProValTyrGluGlyLysSerMetHisGlyM

931  TGATTGAAATGGTCCGTCGTGGTGAATTCCCCGAAGGTTCCAAAGTGCTTTACGCACACTTG
      etIleGluMetValArgArgGlyGluPheProGluGlySerLysValLeuTyrAlaHisLeu

993  GGTGGGGCGCCGGCGCTGAACGCCTACAGCTTCCTGTTTCGTAACGGCTAAGCGTAGAACTG
      GlyGlyAlaProAlaLeuAsnAlaTyrSerPheLeuPheArgAsnGlyEnd

1055  CTTTTGGAGTCATCTGTGGGAGCTC  1079
```

FIGURE 2

```
   1  CTAGAAGGAA GCTTCACGAA ATCGGCCCTT ATTCAAAAAT AACTTTTAAA
  51  TAATGAATTT TAAATTTTAA GAAATAATAT CCAATGAATA AATGACATGT
 101  AGCATTTTAC CTAAATATTT CAACTATTTT AATCCAATAT TAATTTGTTT
 151  TATTCCCAAC AATAGAAAGT CTTGTGCAGA CATTTAATCT GACTTTTCCA
 201  GTACTAAATA TTAATTTTCT GAAGATTTTC GGGTTTAGTC CACAAGTTTT
 251  AGTGAGAAGT TTTGCTCAAA ATTTTAGGTG AGAAGGTTTG ATATTTATCT
 301  TTTGTTAAAT TAATTTATCT AGGTGACTAT TATTTATTTA AGTAGAAATT
 351  CATATCATTA CTTTTGCCAA CTTGTAGTCA TAATAGGAGT AGGTGTATAT
 401  GATGAAGGAA TAAACAAGTT CAGTGAAGTG ATTAAAATAA AATATAATTT
 451  AGGTGTACAT CAAATAAAAA CCTTAAAGTT TAGAAAGGCA CCGAATAATT
 501  TTGCATAGAA GATATTAGTA AATTTATAAA AATAAAAGAA ATGTAGTTGT
 551  CAAGTTGTCT TCTTTTTTTT GGATAAAAAT AGCAGTTGGC TTATGTCATT
 601  CTTTTACAAC CTCCATGCCA CTTGTCCAAT TGTTGACACT TAACTAATTA
 651  GTTGATTCA TGTATGAATA CTAAATAATT TTTAGGACT GACTCAAATA
 701  TTTTTATATT ATCATAGTAA TATTTATCTA ATTTTAGGA CCACTTATTA
 751  CTAAATAATA AATTAACTAC TACTATATTA TTGTTGTGAA ACAACAACGT
 801  TTTGGTTGTT ATGATGAAAC GTACACTATA TCAGTATGAA AAATTCAAAA
 851  CGATTAGTAT AAATTATATT GAAAATTTGA TATTTTTCTA TTCTTAATCA
 901  GACGTATTGG GTTTCATATT TTAAAAGGG ACTAAACTTA GAAGAGAAGT
 951  TTGTTTGAAA CTACTTTTGT CTCTTTCTTG TTCCCATTTC TCTCTTAGAT
1001  TTCAAAAAGT GAACTACTTT ATCTCTTTCT TGTTCACAT TTTATTTTAT
1051  TCTATTATAA ATATGGCATC CTCATATTGA GATTTTAGA AATTATTCTA
1101  ATCATTCACA GTGCAAAAGA AGATCTAAAG CCCTAGAG
```

FIGURE 14

```
ACAGCCGTCCTAAGGAGAAGATAAGATCTATGAAAAAACTGAAACTGCATGGCTTTAATA  60
                                MetLysLysLeuLysLeuHisGlyPheAsnA

ATCTGACCAAAAGTCTGAGTTTTTGTATTTACGATATCTGCTACGCCAAAACTGCCGAAG  120
snLeuThrLysSerLeuSerPheCysIleTyrAspIleCysTyrAlaLysThrAlaGluG

AGCGCGACGGTTATATTGCTTATATCGATGAACTCTATAATGCCAACCGTCTGACCGAAA  180
luArgAspGlyTyrIleAlaTyrIleAspGluLeuTyrAsnAlaAsnArgLeuThrGluI

TCCTGTCAGAAACCTGTTCCATTATCGGGGCTAATATTCTTAACATCGCCCGCCAGGATT  240
leLeuSerGluThrCysSerIleIleGlyAlaAsnIleLeuAsnIleAlaArgGlnAspT

ACGAACCACAGGGTGCCAGCGTCACTATTCTGGTGAGTGAAGAACCGGTTGACCCGAAAC  300
yrGluProGlnGlyAlaSerValThrIleLeuValSerGluGluProValAspProLysL

TCATCGACAAAACAGAACACCCCGGCCCACTGCCAGAAACGGTCGTTGCCCATCTTGATA  360
euIleAspLysThrGluHisProGlyProLeuProGluThrValValAlaHisLeuAspL

AAAGTCATATTTGCGTACATACCTACCCGGAAAGTCATCCTGAAGGCGGTTTATGTACCT  420
ysSerHisIleCysValHisThrTyrProGluSerHisProGluGlyGlyLeuCysThrP

TCCGCGCCGATATTGAAGTCTCTACCTGCGGCGTGATTTCTCCGCTGAAGGCGCTGAATT  480
heArgAlaAspIleGluValSerThrCysGlyValIleSerProLeuLysAlaLeuAsnT

ACCTGATCCACCAGCTTGAGTCCGATATCGTAACCATTGATTATCGCGTGCGCGGTTTTA  540
yrLeuIleHisGlnLeuGluSerAspIleValThrIleAspTyrArgValArgGlyPheT

CCCGCGACATTAACGGTATGAAGCACTTTATCGACCATGAGATTAATTCGATTCAGAACT  600
hrArgAspIleAsnGlyMetLysHisPheIleAspHisGluIleAsnSerIleGlnAsnP

TTATGTCTGACGATATGAAGGCGCTGTATGACATGGTGGATGTGAACGTCTATCAGGAAA  660
heMetSerAspAspMetLysAlaLeuTyrAspMetValAspValAsnValTyrGlnGluA

ATATCTTCCATACCAAGATGTTGCTTAAAGAGTTCGACCTTAAGCACTACATGTTCCACA  720
snIlePheHisThrLysMetLeuLeuLysGluPheAspLeuLysHisTyrMetPheHisT

CCAAACCGGAAGACTTAACCGACAGCGAGCGCCAGGAAATTACCGCTGCGCTGTGGAAAG  780
hrLysProGluAspLeuThrAspSerGluArgGlnGluIleThrAlaAlaLeuTrpLysG

AAATGCGCGAGATTTATTACGGGCGCAATATGCCAGCTGTTTAACGGCTCTGGCGGAGCT  840
luMetArgGluIleTyrTyrGlyArgAsnMetProAlaVal*

CCCAGGCTCCGCCAGATCTATTTACTTCTGCTGCACGAAATTGCGGTAAGCCGCCACGAC  900
```

FIGURE 15

```
CCAAACACATAATACTTTAATACAATTAGTTATTATTAGAAGTATTTAAAGTAAAGCA        60

CTTGTGAGTTGTGTACATTTTATTAATCTTCATCTTTCCTTAATTCTCTTCAGTTTTAATT    120

TCTTCACTTCTAAACTCATTAGTAAAAAAAAAATGGATTGAGATTGCAAAGACCAAC        180
                                 MetGlyPheGluIleAlaLysThrAsn

TCAATCTTATCAAAATTGGCTACTAATGAAGAGCATGGCGAAAACTCGCCATATTTGAT     240
SerIleLeuSerLysLeuAlaThrAsnGluGluHisGlyGluAsnSerProTyrPheAsp

GGGTGGAAAGCATACGATAGTGATCCTTTCCACCCCTAAAAAACCCCAACGGAGTTATC    300
GlyTrpLysAlaTyrAspSerAspProPheHisProLeuLysAsnProAsnGlyValIle

CAAAATGGGTCTTGCTGAAAATCAGCTTTGTTTAGACTTGATAGAAGATTGGATTAAGAGA  360
GlnMetGlyLeuAlaGluAsnGlnLeuCysLeuAspLeuIleGluAspTrpIleLysArg

AACCCAAAAGGTTCAATTTGTTCTGAAGGAATCAAATCATTCAAGGCCATTGCCAACTTT  420
AsnProLysGlySerIleCysSerGluGlyIleLysSerPheLysAlaIleAlaAsnPhe

CAAGATTATCATGGCTTGCCTGAATTCAGAAAAGCGATTGCAAATTTATGGAAAAACA    480
GlnAspTyrHisGlyLeuProGluPheArgLysAlaIleAlaLysPheMetGluLysThr

AGAGGAGGAAGAGTTAGATTTGATCCAGAAAGAGTTGTTATGGCTGGTGGTGCCACTGGA  540
ArgGlyGlyArgValArgPheAspProGluArgValValMetAlaGlyGlyAlaThrGly
```

FIG. 16A

```
GCTAATGAGACAATTATATTTGTTTGGCTGATCCTGGCGATGCATTTTAGTACCTTCA    600
AlaAsnGluThrIleIlePheCysLeuAlaAspProGlyAspAlaPheLeuValProSer

CCATACTACCCAGCATTTAACAGAGATTAAGATGGAGAACTGGAGTACAACTTATTCCA    660
ProTyrTyrProAlaPheAsnArgAspLeuArgTrpArgThrGlyValGlnLeuIlePro

ATTCACTGTGAGAGCTCCAATAATTTCAAAATTACTTCAAAAGCAGTAAAAGAAGCATAT    720
IleHisCysGluSerSerAsnAsnPheLysIleThrSerLysAlaValLysGluAlaTyr

GAAAATGCACAAAAATCAAACATCAAAGTTTGATTTTGACCAATCCATCAAAT         780
GluAsnAlaGlnLysSerAsnIleLysValLysGlyLeuIleLeuThrAsnProSerAsn

CCATTGGGCACCACTTTGGACAAAGACACACTGAAAAGTCTTGAGTTTCACCAACCAA    840
ProLeuGlyThrThrLeuAspLysAspThrLeuLysSerValLeuSerPheThrAsnGln

CACACAACATCCACCTGTTTGTGACGAAATCTACGCAGCCACTGTCTTTGACACGCCTCAA  900
HisAsnIleHisLeuValCysAspGluIleTyrAlaAlaThrValPheAspThrProGln

TTCGTCAGTATAGCTGAAATCCCTCGATGAACAGGAAATGACTTACTGCAACAAAGATTTA  960
  PheValS  IleAlaGluIleLeuLeuAspGLUGlnMetThrTyrCysAsnLysAspLeu

GTTCACATCGTCTACAGTCTTTCAAAAGACATGGGGTTACCAGGATTTAGAGTCGGAATC  1020
ValHisIleValTyrSerLeuSerLysAspMetGlyLeuProGlyPheArgValGlyIle
```

FIG. 16B

```
ATATATTCTTTTAACGACGATGTCGTTAATTGTGTCTAGAAAAATGTCGAGTTTCGGTTTA                1080
IleTyrSerPheAsnAspAspValValAsnCysAlaArgLysMetSerSerPheGlyLeu

GTATCTACACAAACGCAATATTTTTAGCGGGCAATGCCATCGGACGAAAAATTCGTCGAT                1140
ValSerThrGlnThrGlnTyrPheLeuAlaAlaMetProSerAspGluLysPheValAsp

AATTTCTAAGAGAAAGGCGCGATGAGGTTAGGTAAAAGGCACAAACATTTTACTAATGGA                1200
AsnPheLeuArgGluSerAlaMetArgLeuGlyLysArgHisLysHisPheThrAsnGly

CTTGAAGTAGTGGGAATTAAATGCTTGAAAAATAATGCGGGGCTTTTTTGTTGGATGGAT                1260
LeuGluValValGlyIleLysCysLeuLysAsnAsnAlaGlyLeuPheCysTrpMetAsp

TTGCGTCCACTTTTAAGGGAATCGACTTTCGATAGCGAAATGTCGTTATGGAGAGTTATT                1320
LeuArgProLeuLeuArgGluSerThrPheAspSerGluMetSerLeuTrpArgValIle

ATAAACGATGTTAAGCTTAACGTCTCCGCTTCGTTGAATGTCAAGAGCCAGGG                       1380
IleAsnAspValLysLeuAsnValSerLeuGlySerPheGluCysGlnGluProGly

TGGTTCCGAGTTTGTTTTGCAAATATGGATGATGGAACGGTTGATATTGCCTCGCGAGG                 1440
TrpPheArgValCysPheAlaAsnMetAspAspGlyThrValAspIleAlaLeuAlaArg
```

FIG. 16C

```
ATTCGGAGGTTCGTAGGTGTTGAGAAAAGTGGAGATAAATCGAGTTCGATGGAAAGAAG    1500
IleArgArgPheValGlyValGluLysSerGlyAspLysSerSerMetGluLysLys

CAACAATGGAAGAAGAATAATTTGAGACTTAGTTTTTCGAAAAGAATGTATGATGAAAGT    1560
GlnGlnTrpLysLysAsnAsnLeuArgLeuSerPheSerLysArgMetTyrAspGluSer

GTTTTGTCACCACTTTCGTCACCTATTCCCTCCCTCACCATTAGTTCGTTAAGACTTAATT  1620
ValLeuSerProLeuSerSerProIleProProSerProLeuValArg*

AAAAGGGAAGAATTAATTTATGTTTTTTATATTTGAAAAAATTTGTAAGAATAAGA       1680

TTATAATAGGAAAAGAAAAATAAGTATGTAGGATGAGGAGTATTTCAGAAATAGTTGTTA   1740

GCGTATGTATTGACAACTGGTCTATGTACTTAGACATCATAATTTGTCTTAGCTAATTAA   1800

TGAATGCAAAAGTGAAGTT
```

FIG. 16D

```
GGATCC ATG AAT TTG AAT CGT TTT AAA CGT TAT CCG TTG ACC TTC GGT    48
       Met Asn Leu Asn Arg Phe Lys Arg Tyr Pro Leu Thr Phe Gly
CCT TCT CCC ATC ACG CCC TTG AAG CGC CTC AGT GAA CAC TTG GGT GGC    96
Pro Ser Pro Ile Thr Pro Leu Lys Arg Leu Ser Glu His Leu Gly Gly
AAG GTC GAG CTG TAT GCC AAG CGT GAA GAC TGC AAC AGT GGC CTG GCC   144
Lys Val Glu Leu Tyr Ala Lys Arg Glu Asp Cys Asn Ser Gly Leu Ala
TTC GGC GGG AAC AAA ACG CGC AAG CTC GAA TAT TTG ATT CCC GAA GCG   192
Phe Gly Gly Asn Lys Thr Arg Lys Leu Glu Tyr Leu Ile Pro Glu Ala
CTC GAG CAA GGC TGC GAT ACC TTG GTT TCC ATC GGC GGC ATC CAG TCG   240
Leu Glu Gln Gly Cys Asp Thr Leu Val Ser Ile Gly Gly Ile Gln Ser
AAC CAG ACC CGC CAG GTG GCC GCC GTT GCC GCT CAC CTG GGC ATG AAG   288
Asn Gln Thr Arg Gln Val Ala Ala Val Ala Ala His Leu Gly Met Lys
TGC GTG CTG GTG CAG GAA AAC TGG GTG AAC TAC TCC GAT GCG GTG TAT   336
Cys Val Leu Val Gln Glu Asn Trp Val Asn Tyr Ser Asp Ala Val Tyr
GAC CGC GTT GGC AAT ATC GAA ATG TCT CGC ATC ATG GGC GCC GAG GTA   384
Asp Arg Val Gly Asn Ile Glu Met Ser Arg Ile Met Gly Ala Glu Val
CGA CTG GAC GCC GCC GGG TTC GAT ATC GGC ATT CGG CCC AGC TGG GAG   432
Arg Leu Asp Ala Ala Gly Phe Asp Ile Gly Ile Arg Pro Ser Trp Glu
AAG GCC ATG GAC GAT GTG GTG GCG CGG GGT GGC AAG CCG TTC CCG ATA   480
Lys Ala Met Asp Asp Val Val Ala Arg Gly Gly Lys Pro Phe Pro Ile
CCG GCG GGT TGT TCC GAA CAC CCC TAC GGC GGC CTT GGG TTC GTC GGC   528
Pro Ala Gly Cys Ser Glu His Pro Tyr Gly Gly Leu Gly Phe Val Gly
TTT GCC GAG GAA GTG CGA GAG CAG GAA AAA CAA CTG GGG TTC ACG TTC   576
Phe Ala Glu Glu Val Arg Glu Gln Glu Lys Gln Leu Gly Phe Thr Phe
GAC TAC ATC GTG GTC TGC TCT GTG ACC GGC AGT ACC CAG GCC GGC ATG   624
Asp Tyr Ile Val Val Cys Ser Val Thr Gly Ser Thr Gln Ala Gly Met
GTC GTC GGT TTC GCC GCG GAC GGC CGT TCG AAG AAC GTT ATC GGC ATT   672
Val Val Gly Phe Ala Ala Asp Gly Arg Ser Lys Asn Val Ile Gly Ile
GAT GCC TCG GCC AAG CCG GAG CAA ACC AAG GCA CAG ATC CTG CGT ATC   720
Asp Ala Ser Ala Lys Pro Glu Gln Thr Lys Ala Gln Ile Leu Arg Ile
GCC CGG CAC ACC GCA GAG TTG GTG GAA CTG GGC CGT GAG ATC ACC GAA   768
Ala Arg His Thr Ala Glu Leu Val Glu Leu Gly Arg Glu Ile Thr Glu
GAC GAC GTG GTG CTC GAT ACA CGT TTT GCC TAC CCG GAA TAC GGT TTG   816
Asp Asp Val Val Leu Asp Thr Arg Phe Ala Tyr Pro Glu Tyr Gly Leu
CCC AAC GAA GGC ACG CTG GAA GCC ATT CGT TTG TGC GGG AGC CTG GAA   864
Pro Asn Glu Gly Thr Leu Glu Ala Ile Arg Leu Cys Gly Ser Leu Glu
GGT GTG CTG ACC GAT CCG GTG TAC GAG GGC AAA TCC ATG CAC GGG ATG   912
Gly Val Leu Thr Asp Pro Val Tyr Glu Gly Lys Ser Met His Gly Met
ATT GAA ATG GTC CGC CGT GGC GAG TTC CCC GAA GGC TCC AAA GTG CTG   960
Ile Glu Met Val Arg Arg Gly Glu Phe Pro Glu Gly Ser Lys Val Leu
TAT GCG CAC TTG GGT GGG GCG CCT GCG CTG AAT GCC TAC AGC TTC CTG  1008
Tyr Ala His Leu Gly Gly Ala Pro Ala Leu Asn Ala Tyr Ser Phe Leu
TTT CGT AAC GGC GGATCCGGG                                        1029
Phe Arg Asn Gly
```

FIGURE 17

```
AGATCTATCGATAAGCTTGATGTAATTGGAGGAAGATCAAAATTTTCAAT    50

CCCCATTCTTCGATTGCTTCAATTGAAGTTTCTCCGATGGCGCAAGTTAG   100

CAGAATCTGCAATGGTGTGCAGAACCCATCTCTTATCTCCAATCTCTCGA   150

AATCCAGTCAACGCAAATCTCCCTTATCGGTTTCTCTGAAGACGCAGCAG   200

CATCCACGAGCTTATCCGATTTCGTCGTCGTGGGGATTGAAGAAGAGTGG   250

GATGACGTTAATTGGCTCTGAGCTTCGTCCTCTTAAGGTCATGTCTTCTG   300

TTTCCACGGCGTGCATGC                                   318
```

FIGURE 20

```
GCATGCTTCACGGTGCAAGCAGCCGTCCAGCAACTGCTCGTAAGTCCTCT   50
GGTCTTTCTGGAACCGTCCGTATTCCAGGTGACAAGTCTATCTCCCACAG  100
GTCCTTCATGTTTGGAGGTCTCGCTAGCGGTGAAACTCGTATCACCGGTC  150
TTTTGGAAGGTGAAGATGTTATCAACACTGGTAAGGCTATGCAAGCTATG  200
GGTGCCAGAATCCGTAAGGAAGGTGATACTTGGATCATTGATGGTGTTGG  250
TAACGGTGGACTCCTTGCTCCTGAGGCTCCTCTCGATTTCGGTAACGCTG  300
CAACTGGTTGCCGTTTGACTATGGGTCTTGTTGGTGTTTACGATTTCGAT  350
AGCACTTTCATTGGTGACGCTTCTCTCACTAAGCGTCCAATGGGTCGTGT  400
GTTGAACCCACTTCGCGAAATGGGTGTGCAGGTGAAGTCTGAAGACGGTG  450
ATCGTCTTCCAGTTACCTTGCGTGGACCAAAGACTCCAACGCCAATCACC  500
TACAGGGTACCTATGGCTTCCGCTCAAGTGAAGTCCGCTGTTCTGCTTGC  550
TGGTCTCAACACCCCAGGTATCACCACTGTTATCGAGCCAATCATGACTC  600
GTGACCACACTGAAAAGATGCTTCAAGGTTTTGGTGCTAACCTTACCGTT  650
GAGACTGATGCTGACGGTGTGCGTACCATCCGTCTTGAAGGTCGTGGTAA  700
GCTCACCGGTCAAGTGATTGATGTTCCAGGTGATCCATCCTCTACTGCTT  750
TCCCATTGGTTGCTGCCTTGCTTGTTCCAGGTTCCGACGTCACCATCCTT  800
AACGTTTTGATGAACCCAACCCGTACTGGTCTCATCTTGACTCTGCAGGA  850
AATGGGTGCCGACATCGAAGTGATCAACCCACGTCTTGCTGGTGGAGAAG  900
ACGTGGCTGACTTGCGTGTTCGTTCTTCTACTTTGAAGGGTGTTACTGTT  950
CCAGAAGACCGTGCTCCTTCTATGATCGACGAGTATCCAATTCTCGCTGT 1000
TGCAGCTGCATTCGCTGAAGGTGCTACCGTTATGAACGGTTTGGAAGAAC 1050
TCCGTGTTAAGGAAAGCGACCGTCTTTCTGCTGTCGCAAACGGTCTCAAG 1100
CTCAACGGTGTTGATTGCGATGAAGGTGAGACTTCTCTCGTCGTGCGTGG 1150
TCGTCCTGACGGTAAGGGTCTCGGTAACGCTTCTGGAGCAGCTGTCGCTA 1200
CCCACCTCGATCACCGTATCGCTATGAGCTTCCTCGTTATGGGTCTCGTT 1250
TCTGAAAACCCTGTTACTGTTGATGATGCTACTATGATCGCTACTAGCTT 1300
CCCAGAGTTCATGGATTTGATGGCTGGTCTTGGAGCTAAGATCGAACTCT 1350
CCGACACTAAGGCTGCTTGATGAGCTC                         1377
```

FIGURE 21

```
TCATCAAAATATTTAGCAGCATTCCAGATTGGGTTCAATCAACAAGGTAC  50
GAGCCATATCACTTTATTCAAATTGGTATCGCCAAAACCAAGAAGGAACT  100
CCCATCCTCAAAGGTTTGTAAGGAAGAATTCTCAGTCCAAAGCCTCAACA  150
AGGTCAGGGTACAGAGTCTCCAAACCATTAGCCAAAAGCTACAGGAGATC  200
AATGAAGAATCTTCAATCAAAGTAAACTACTGTTCCAGCACATGCATCAT  250
GGTCAGTAAGTTTCAGAAAAGACATCCACCGAAGACTTAAAGTTAGTGG  300
GCATCTTTGAAAGTAATCTTGTCAACATCGAGCAGCTGGCTTGTGGGAC  350
CAGACAAAAAAGGAATGGTGCAGAATTGTTAGGCGCACCTACCAAAAGCA  400
TCTTTGCCTTTATTGCAAAGATAAAGCAGATTCCTCTAGTACAAGTGGGG  450
AACAAAATAACGTGGAAAAGAGCTGTCCTGACAGCCCACTCACTAATGCG  500
TATGACGAACGCAGTGACGACCACAAAAGAATTCCCTCTATATAAGAAGG  550
CATTCATTCCCATTTGAAGGATCATCAGATACTAACCAATATTTCTC     596
```

FIGURE 22

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1079 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GATATCCCAT ATCAAGGAGC AGAGTC ATG AAT CTG AAT CGT TTT GAA CGT TAT            53
                             Met Asn Leu Asn Arg Phe Glu Arg Tyr
                              1               5

CCA TTG ACC TTC GGT CCT TCT CCC ATC ACG CCC TTG AAG CGC CTC AGT           101
Pro Leu Thr Phe Gly Pro Ser Pro Ile Thr Pro Leu Lys Arg Leu Ser
 10              15                  20                      25

CAA CAT CTG GGG GGC AAG GTC GAG CTG TAT GCC AAA CGT GAA GAC TGC           149
Gln His Leu Gly Gly Lys Val Glu Leu Tyr Ala Lys Arg Glu Asp Cys
             30                  35                  40

AAC AGT GGC CTG GCC TTT GGT GGG AAC AAG ACG CGC AAG CTC GAA TAC           197
Asn Ser Gly Leu Ala Phe Gly Gly Asn Lys Thr Arg Lys Leu Glu Tyr
             45                  50                  55

CTC ATT CCC GAA GCG ATC GAG CAA GGC TGC GAT ACG CTG GTT TCC ATC           245
Leu Ile Pro Glu Ala Ile Glu Gln Gly Cys Asp Thr Leu Val Ser Ile
             60                  65                  70

GGC GGC ATC CAG TCG AAC CAG ACC CGT CAG GTC GCT GCC GTC GCT GCC           293
Gly Gly Ile Gln Ser Asn Gln Thr Arg Gln Val Ala Ala Val Ala Ala
     75                  80                  85

CAC TTG GGC ATG AAG TGC GTG TTG GTG CAG GAA AAC TGG GTG AAC TAT           341
His Leu Gly Met Lys Cys Val Leu Val Gln Glu Asn Trp Val Asn Tyr
 90                  95                 100                 105

TCC GAC GCG GTG TAT GAC CGC GTA GGC AAC ATC GAG ATG TCG CGG ATC           389
Ser Asp Ala Val Tyr Asp Arg Val Gly Asn Ile Glu Met Ser Arg Ile
                 110                 115                 120

ATG GGC GCT GAT GTG CGG CTT GAC GCC GCT GGC TTC GAT ATT GGC ATT           437
Met Gly Ala Asp Val Arg Leu Asp Ala Ala Gly Phe Asp Ile Gly Ile
                 125                 130                 135

CGG CCA AGT TGG GAA AAG GCC ATG AGC GAT GTC GTG GAA CAG GGT GGC           485
Arg Pro Ser Trp Glu Lys Ala Met Ser Asp Val Val Glu Gln Gly Gly
         140                 145                 150

AAA CCG TTT CCG ATT CCA GCG GGT TGC TCC GAG CAT CCC TAT GGC GGC           533
Lys Pro Phe Pro Ile Pro Ala Gly Cys Ser Glu His Pro Tyr Gly Gly
         155                 160                 165
```

| | | | | | | | | | | | | | | | | |
|---|---|---|---|---|---|---|---|---|---|---|---|---|---|---|---|---|
| CTC | GGT | TTC | GTC | GGC | TTT | GCC | GAA | GAG | GTG | CGG | CAG | CAG | GAA | AAG | GAA | 581 |
| Leu | Gly | Phe | Val | Gly | Phe | Ala | Glu | Glu | Val | Arg | Gln | Gln | Glu | Lys | Glu | |
| 170 | | | | | 175 | | | | | 180 | | | | | 185 | |
| CTG | GGC | TTC | AAG | TTT | GAC | TAC | ATC | GTG | GTC | TGC | TCG | GTG | ACC | GGC | AGT | 629 |
| Leu | Gly | Phe | Lys | Phe | Asp | Tyr | Ile | Val | Val | Cys | Ser | Val | Thr | Gly | Ser | |
| | | | | 190 | | | | | 195 | | | | | 200 | | |
| ACG | CAG | GCG | GGC | ATG | GTT | GTT | GGT | TTC | GCG | GCT | GAC | GGT | CGT | TCG | AAG | 677 |
| Thr | Gln | Ala | Gly | Met | Val | Val | Gly | Phe | Ala | Ala | Asp | Gly | Arg | Ser | Lys | |
| | | | 205 | | | | | 210 | | | | | 215 | | | |
| AAT | GTG | ATT | GGT | ATC | GAT | GCT | TCG | GCC | AAG | CCG | GAA | CAG | ACC | AAG | GCA | 725 |
| Asn | Val | Ile | Gly | Ile | Asp | Ala | Ser | Ala | Lys | Pro | Glu | Gln | Thr | Lys | Ala | |
| | | 220 | | | | | 225 | | | | | 230 | | | | |
| CAG | ATC | CTG | CGC | ATC | GCC | CGA | CAC | ACC | GCT | GAG | TTG | GTG | GAG | TTG | GGG | 773 |
| Gln | Ile | Leu | Arg | Ile | Ala | Arg | His | Thr | Ala | Glu | Leu | Val | Glu | Leu | Gly | |
| | 235 | | | | | 240 | | | | | 245 | | | | | |
| CGC | GAG | ATT | ACG | GAA | GAG | GAC | GTG | GTG | CTC | GAT | ACG | CGT | TTT | GCC | TAC | 821 |
| Arg | Glu | Ile | Thr | Glu | Glu | Asp | Val | Val | Leu | Asp | Thr | Arg | Phe | Ala | Tyr | |
| 250 | | | | | 255 | | | | | 260 | | | | | 265 | |
| CCG | GAA | TAT | GGC | TTG | CCC | AAC | GAA | GGC | ACA | TTG | GAA | GCC | ATC | CGA | CTG | 869 |
| Pro | Glu | Tyr | Gly | Leu | Pro | Asn | Glu | Gly | Thr | Leu | Glu | Ala | Ile | Arg | Leu | |
| | | | | 270 | | | | | 275 | | | | | 280 | | |
| TGC | GGC | AGC | CTT | GAA | GGC | GTG | CTG | ACA | GAC | CCG | GTA | TAT | GAA | GGT | AAA | 917 |
| Cys | Gly | Ser | Leu | Glu | Gly | Val | Leu | Thr | Asp | Pro | Val | Tyr | Glu | Gly | Lys | |
| | | | 285 | | | | | 290 | | | | | 295 | | | |
| TCG | ATG | CAC | GGC | ATG | ATT | GAA | ATG | GTC | CGT | CGT | GGT | GAA | TTC | CCC | GAA | 965 |
| Ser | Met | His | Gly | Met | Ile | Glu | Met | Val | Arg | Arg | Gly | Glu | Phe | Pro | Glu | |
| | | 300 | | | | | 305 | | | | | 310 | | | | |
| GGT | TCC | AAA | GTG | CTT | TAC | GCA | CAC | TTG | GGT | GGG | GCG | CCG | GCG | CTG | AAC | 1013 |
| Gly | Ser | Lys | Val | Leu | Tyr | Ala | His | Leu | Gly | Gly | Ala | Pro | Ala | Leu | Asn | |
| | 315 | | | | | 320 | | | | | 325 | | | | | |
| GCC | TAC | AGC | TTC | CTG | TTT | CGT | AAC | GGC | TAAGCGTAGA | | ACTGCTTTTG | | | | | 1060 |
| Ala | Tyr | Ser | Phe | Leu | Phe | Arg | Asn | Gly | | | | | | | | |
| 330 | | | | | 335 | | | | | | | | | | | |

GAGTCATCTG TGGGAGCTC 1079

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GAAGGAAGCT TCACGAAATC GGCCCTTATT C  31

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

GGGGCTTTAG ATCTTCTTTT GCACTGTGAA TG  32

( 2 ) INFORMATION FOR SEQ ID NO:4:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:4:

GGTGAACCAT GGAATTCCAC ATG 23

( 2 ) INFORMATION FOR SEQ ID NO:5:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:5:

GCAATTGGAT CCCTTTCCAT AGC 23

( 2 ) INFORMATION FOR SEQ ID NO:6:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:6:

GGAGAAGATA AGATCTATGA AAAAACTGAA ACTGC 35

( 2 ) INFORMATION FOR SEQ ID NO:7:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:7:

GCAGAAGTAA ATAGATCTGG CGGAGCC 27

( 2 ) INFORMATION FOR SEQ ID NO:8:

( i ) SEQUENCE CHARACTERISTICS:
    ( A ) LENGTH: 1800 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:8:

```
CCAAACACAT AATACTTTTA ATACAATTAG TTATTTATTA GAAGTATTTA AAGTAAAGCA      60

CTTGTGAGTT GTGTACATTT TATTAATCTT CATCTTCTTA ATTCTCTTCA GTTTTTAATT     120

TCTTCACTTC TAAACTCATT TAGTAAAAAA AAA ATG GGA TTT GAG ATT GCA AAG     174
                                     Met Gly Phe Glu Ile Ala Lys
                                      1               5

ACC AAC TCA ATC TTA TCA AAA TTG GCT ACT AAT GAA GAG CAT GGC GAA      222
Thr Asn Ser Ile Leu Ser Lys Leu Ala Thr Asn Glu Glu His Gly Glu
```

|     |     |     |     |     | 10  |     |     |     |     | 15  |     |     |     |     | 20  |     |      |
| --- | --- | --- | --- | --- | --- | --- | --- | --- | --- | --- | --- | --- | --- | --- | --- | --- | ---- |
| AAC | TCG | CCA | TAT | TTT | GAT | GGG | TGG | AAA | GCA | TAC | GAT | AGT | GAT | CCT | TTC |     | 270  |
| Asn | Ser | Pro | Tyr | Phe | Asp | Gly | Trp | Lys | Ala | Tyr | Asp | Ser | Asp | Pro | Phe |     |      |
|     | 25  |     |     |     |     | 30  |     |     |     |     | 35  |     |     |     |     |     |      |
| CAC | CCT | CTA | AAA | AAC | CCC | AAC | GGA | GTT | ATC | CAA | ATG | GGT | CTT | GCT | GAA |     | 318  |
| His | Pro | Leu | Lys | Asn | Pro | Asn | Gly | Val | Ile | Gln | Met | Gly | Leu | Ala | Glu |     |      |
| 40  |     |     |     |     | 45  |     |     |     |     | 50  |     |     |     |     | 55  |     |      |
| AAT | CAG | CTT | TGT | TTA | GAC | TTG | ATA | GAA | GAT | TGG | ATT | AAG | AGA | AAC | CCA |     | 366  |
| Asn | Gln | Leu | Cys | Leu | Asp | Leu | Ile | Glu | Asp | Trp | Ile | Lys | Arg | Asn | Pro |     |      |
|     |     |     |     | 60  |     |     |     |     | 65  |     |     |     |     | 70  |     |     |      |
| AAA | GGT | TCA | ATT | TGT | TCT | GAA | GGA | ATC | AAA | TCA | TTC | AAG | GCC | ATT | GCC |     | 414  |
| Lys | Gly | Ser | Ile | Cys | Ser | Glu | Gly | Ile | Lys | Ser | Phe | Lys | Ala | Ile | Ala |     |      |
|     |     |     | 75  |     |     |     |     | 80  |     |     |     |     | 85  |     |     |     |      |
| AAC | TTT | CAA | GAT | TAT | CAT | GGC | TTG | CCT | GAA | TTC | AGA | AAA | GCG | ATT | GCG |     | 462  |
| Asn | Phe | Gln | Asp | Tyr | His | Gly | Leu | Pro | Glu | Phe | Arg | Lys | Ala | Ile | Ala |     |      |
|     |     | 90  |     |     |     |     | 95  |     |     |     |     | 100 |     |     |     |     |      |
| AAA | TTT | ATG | GAG | AAA | ACA | AGA | GGA | GGA | AGA | GTT | AGA | TTT | GAT | CCA | GAA |     | 510  |
| Lys | Phe | Met | Glu | Lys | Thr | Arg | Gly | Gly | Arg | Val | Arg | Phe | Asp | Pro | Glu |     |      |
|     |     | 105 |     |     |     |     | 110 |     |     |     |     | 115 |     |     |     |     |      |
| AGA | GTT | GTT | ATG | GCT | GGT | GGT | GCC | ACT | GGA | GCT | AAT | GAG | ACA | ATT | ATA |     | 558  |
| Arg | Val | Val | Met | Ala | Gly | Gly | Ala | Thr | Gly | Ala | Asn | Glu | Thr | Ile | Ile |     |      |
| 120 |     |     |     |     | 125 |     |     |     |     | 130 |     |     |     |     | 135 |     |      |
| TTT | TGT | TTG | GCT | GAT | CCT | GGC | GAT | GCA | TTT | TTA | GTA | CCT | TCA | CCA | TAC |     | 606  |
| Phe | Cys | Leu | Ala | Asp | Pro | Gly | Asp | Ala | Phe | Leu | Val | Pro | Ser | Pro | Tyr |     |      |
|     |     |     |     | 140 |     |     |     |     | 145 |     |     |     |     | 150 |     |     |      |
| TAC | CCA | GCA | TTT | AAC | AGA | GAT | TTA | AGA | TGG | AGA | ACT | GGA | GTA | CAA | CTT |     | 654  |
| Tyr | Pro | Ala | Phe | Asn | Arg | Asp | Leu | Arg | Trp | Arg | Thr | Gly | Val | Gln | Leu |     |      |
|     |     |     | 155 |     |     |     |     | 160 |     |     |     |     | 165 |     |     |     |      |
| ATT | CCA | ATT | CAC | TGT | GAG | AGC | TCC | AAT | AAT | TTC | AAA | ATT | ACT | TCA | AAA |     | 702  |
| Ile | Pro | Ile | His | Cys | Glu | Ser | Ser | Asn | Asn | Phe | Lys | Ile | Thr | Ser | Lys |     |      |
|     |     | 170 |     |     |     |     | 175 |     |     |     |     | 180 |     |     |     |     |      |
| GCA | GTA | AAA | GAA | GCA | TAT | GAA | AAT | GCA | CAA | AAA | TCA | AAC | ATC | AAA | GTA |     | 750  |
| Ala | Val | Lys | Glu | Ala | Tyr | Glu | Asn | Ala | Gln | Lys | Ser | Asn | Ile | Lys | Val |     |      |
|     | 185 |     |     |     |     | 190 |     |     |     |     | 195 |     |     |     |     |     |      |
| AAA | GGT | TTG | ATT | TTG | ACC | AAT | CCA | TCA | AAT | CCA | TTG | GGC | ACC | ACT | TTG |     | 798  |
| Lys | Gly | Leu | Ile | Leu | Thr | Asn | Pro | Ser | Asn | Pro | Leu | Gly | Thr | Thr | Leu |     |      |
| 200 |     |     |     |     | 205 |     |     |     |     | 210 |     |     |     |     | 215 |     |      |
| GAC | AAA | GAC | ACA | CTG | AAA | AGT | GTC | TTG | AGT | TTC | ACC | AAC | CAA | CAC | AAC |     | 846  |
| Asp | Lys | Asp | Thr | Leu | Lys | Ser | Val | Leu | Ser | Phe | Thr | Asn | Gln | His | Asn |     |      |
|     |     |     |     | 220 |     |     |     |     | 225 |     |     |     |     | 230 |     |     |      |
| ATC | CAC | CTT | GTT | TGT | GAC | GAA | ATC | TAC | GCA | GCC | ACT | GTC | TTT | GAC | ACG |     | 894  |
| Ile | His | Leu | Val | Cys | Asp | Glu | Ile | Tyr | Ala | Ala | Thr | Val | Phe | Asp | Thr |     |      |
|     |     |     | 235 |     |     |     |     | 240 |     |     |     |     | 245 |     |     |     |      |
| CCT | CAA | TTC | GTC | AGT | ATA | GCT | GAA | ATC | CTC | GAT | GAA | CAG | GAA | ATG | ACT |     | 942  |
| Pro | Gln | Phe | Val | Ser | Ile | Ala | Glu | Ile | Leu | Asp | Glu | Gln | Glu | Met | Thr |     |      |
|     |     |     | 250 |     |     |     |     | 255 |     |     |     |     | 260 |     |     |     |      |
| TAC | TGC | AAC | AAA | GAT | TTA | GTT | CAC | ATC | GTC | TAC | AGT | CTT | TCA | AAA | GAC |     | 990  |
| Tyr | Cys | Asn | Lys | Asp | Leu | Val | His | Ile | Val | Tyr | Ser | Leu | Ser | Lys | Asp |     |      |
|     | 265 |     |     |     |     | 270 |     |     |     |     | 275 |     |     |     |     |     |      |
| ATG | GGG | TTA | CCA | GGA | TTT | AGA | GTC | GGA | ATC | ATA | TAT | TCT | TTT | AAC | GAC |     | 1038 |
| Met | Gly | Leu | Pro | Gly | Phe | Arg | Val | Gly | Ile | Ile | Tyr | Ser | Phe | Asn | Asp |     |      |
| 280 |     |     |     |     | 285 |     |     |     |     | 290 |     |     |     |     | 295 |     |      |
| GAT | GTC | GTT | AAT | TGT | GCT | AGA | AAA | ATG | TCG | AGT | TTC | GGT | TTA | GTA | TCT |     | 1086 |
| Asp | Val | Val | Asn | Cys | Ala | Arg | Lys | Met | Ser | Ser | Phe | Gly | Leu | Val | Ser |     |      |
|     |     |     |     | 300 |     |     |     |     | 305 |     |     |     |     | 310 |     |     |      |
| ACA | CAA | ACG | CAA | TAT | TTT | TTA | GCG | GCA | ATG | CCA | TCG | GAC | GAA | AAA | TTC |     | 1134 |
| Thr | Gln | Thr | Gln | Tyr | Phe | Leu | Ala | Ala | Met | Pro | Ser | Asp | Glu | Lys | Phe |     |      |
|     |     |     | 315 |     |     |     |     | 320 |     |     |     |     | 325 |     |     |     |      |
| GTC | GAT | AAT | TTT | CTA | AGA | GAA | AGC | GCG | ATG | AGG | TTA | GGT | AAA | AGG | CAC |     | 1182 |
| Val | Asp | Asn | Phe | Leu | Arg | Glu | Ser | Ala | Met | Arg | Leu | Gly | Lys | Arg | His |     |      |

|   |   |   |   |   |   |   |   |   |   |   |   |   |   |   |   |      |
|---|---|---|---|---|---|---|---|---|---|---|---|---|---|---|---|------|
|   |   |   | 330 |   |   |   |   | 335 |   |   |   |   | 340 |   |   |      |
| AAA | CAT | TTT | ACT | AAT | GGA | CTT | GAA | GTA | GTG | GGA | ATT | AAA | TGC | TTG | AAA | 1230 |
| Lys | His | Phe | Thr | Asn | Gly | Leu | Glu | Val | Val | Gly | Ile | Lys | Cys | Leu | Lys |      |
|     | 345 |     |     |     | 350 |     |     |     |     | 355 |     |     |     |     |     |      |
| AAT | AAT | GCG | GGG | CTT | TTT | TGT | TGG | ATG | GAT | TTG | CGT | CCA | CTT | TTA | AGG | 1278 |
| Asn | Asn | Ala | Gly | Leu | Phe | Cys | Trp | Met | Asp | Leu | Arg | Pro | Leu | Leu | Arg |      |
| 360 |     |     |     |     | 365 |     |     |     |     | 370 |     |     |     |     | 375 |      |
| GAA | TCG | ACT | TTC | GAT | AGC | GAA | ATG | TCG | TTA | TGG | AGA | GTT | ATT | ATA | AAC | 1326 |
| Glu | Ser | Thr | Phe | Asp | Ser | Glu | Met | Ser | Leu | Trp | Arg | Val | Ile | Ile | Asn |      |
|     |     |     |     | 380 |     |     |     |     | 385 |     |     |     |     | 390 |     |      |
| GAT | GTT | AAG | CTT | AAC | GTC | TCG | CTT | GGA | TCT | TCG | TTT | GAA | TGT | CAA | GAG | 1374 |
| Asp | Val | Lys | Leu | Asn | Val | Ser | Leu | Gly | Ser | Ser | Phe | Glu | Cys | Gln | Glu |      |
|     |     |     | 395 |     |     |     |     | 400 |     |     |     |     | 405 |     |     |      |
| CCA | GGG | TGG | TTC | CGA | GTT | TGT | TTT | GCA | AAT | ATG | GAT | GAT | GGA | ACG | GTT | 1422 |
| Pro | Gly | Trp | Phe | Arg | Val | Cys | Phe | Ala | Asn | Met | Asp | Asp | Gly | Thr | Val |      |
|     |     | 410 |     |     |     |     | 415 |     |     |     |     | 420 |     |     |     |      |
| GAT | ATT | GCG | CTC | GCG | AGG | ATT | CGG | AGG | TTC | GTA | GGT | GTT | GAG | AAA | AGT | 1470 |
| Asp | Ile | Ala | Leu | Ala | Arg | Ile | Arg | Arg | Phe | Val | Gly | Val | Glu | Lys | Ser |      |
|     | 425 |     |     |     |     | 430 |     |     |     |     | 435 |     |     |     |     |      |
| GGA | GAT | AAA | TCG | AGT | TCG | ATG | GAA | AAG | AAG | CAA | CAA | TGG | AAG | AAG | AAT | 1518 |
| Gly | Asp | Lys | Ser | Ser | Ser | Met | Glu | Lys | Lys | Gln | Gln | Trp | Lys | Lys | Asn |      |
| 440 |     |     |     |     | 445 |     |     |     |     | 450 |     |     |     |     | 455 |      |
| AAT | TTG | AGA | CTT | AGT | TTT | TCG | AAA | AGA | ATG | TAT | GAT | GAA | AGT | GTT | TTG | 1566 |
| Asn | Leu | Arg | Leu | Ser | Phe | Ser | Lys | Arg | Met | Tyr | Asp | Glu | Ser | Val | Leu |      |
|     |     |     |     | 460 |     |     |     |     | 465 |     |     |     |     | 470 |     |      |
| TCA | CCA | CTT | TCG | TCA | CCT | ATT | CCT | CCC | TCA | CCA | TTA | GTT | CGT |   |   | 1608 |
| Ser | Pro | Leu | Ser | Ser | Pro | Ile | Pro | Pro | Ser | Pro | Leu | Val | Arg |   |   |      |
|     |     |     | 475 |     |     |     |     | 480 |     |     |     |     | 485 |   |   |      |

TAAGACTTAA TTAAAAGGGA AGAATTTAAT TTATGTTTTT TTATATTTTG AAAAAAATTT 1668

GTAAGAATAA GATTATAATA GGAAAAGAAA ATAAGTATGT AGGATGAGGA GTATTTTCAG 1728

AAATAGTTGT TAGCGTATGT ATTGACAACT GGTCTATGTA CTTAGACATC ATAATTTGTC 1788

TTAGCTAATT AA 1800

( 2 ) INFORMATION FOR SEQ ID NO:9:

( i ) SEQUENCE CHARACTERISTICS:
        ( A ) LENGTH: 900 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

|   |   |   |   |   |   |   |   |   |   |   |   |   |   |   |   |     |
|---|---|---|---|---|---|---|---|---|---|---|---|---|---|---|---|-----|
| ACAGCCGTCC | TAAGGAGAAG | ATAAGATCT | ATG | AAA | AAA | CTG | AAA | CTG | CAT | GGC |   |   |   |   |   | 53  |
|            |            |           | Met | Lys | Lys | Leu | Lys | Leu | His | Gly |   |   |   |   |   |     |
|            |            |           | 1   |     |     |     | 5   |     |     |     |   |   |   |   |   |     |
| TTT | AAT | AAT | CTG | ACC | AAA | AGT | CTG | AGT | TTT | TGT | ATT | TAC | GAT | ATC | TGC | 101 |
| Phe | Asn | Asn | Leu | Thr | Lys | Ser | Leu | Ser | Phe | Cys | Ile | Tyr | Asp | Ile | Cys |     |
|     | 10  |     |     |     | 15  |     |     |     |     | 20  |     |     |     |     |     |     |
| TAC | GCC | AAA | ACT | GCC | GAA | GAG | CGC | GAC | GGT | TAT | ATT | GCT | TAT | ATC | GAT | 149 |
| Tyr | Ala | Lys | Thr | Ala | Glu | Glu | Arg | Asp | Gly | Tyr | Ile | Ala | Tyr | Ile | Asp |     |
| 25  |     |     |     |     | 30  |     |     |     | 35  |     |     |     |     |     | 40  |     |
| GAA | CTC | TAT | AAT | GCC | AAC | CGT | CTG | ACC | GAA | ATC | CTG | TCA | GAA | ACC | TGT | 197 |
| Glu | Leu | Tyr | Asn | Ala | Asn | Arg | Leu | Thr | Glu | Ile | Leu | Ser | Glu | Thr | Cys |     |
|     |     |     |     | 45  |     |     |     | 50  |     |     |     |     | 55  |     |     |     |
| TCC | ATT | ATC | GGG | GCT | AAT | ATT | CTT | AAC | ATC | GCC | CGC | CAG | GAT | TAC | GAA | 245 |
| Ser | Ile | Ile | Gly | Ala | Asn | Ile | Leu | Asn | Ile | Ala | Arg | Gln | Asp | Tyr | Glu |     |
|     |     |     | 60  |     |     |     | 65  |     |     |     |     | 70  |     |     |     |     |
| CCA | CAG | GGT | GCC | AGC | GTC | ACT | ATT | CTG | GTG | AGT | GAA | GAA | CCG | GTT | GAC | 293 |

| | | | | | | | | | | | | | | |
|---|---|---|---|---|---|---|---|---|---|---|---|---|---|---|
|Pro|Gln|Gly|Ala|Ser|Val|Thr|Ile|Leu|Val|Ser|Glu|Glu|Pro|Val|Asp|
| |  |75 | | | | |80 | | | | |85 | | | |

```
CCG  AAA  CTC  ATC  GAC  AAA  ACA  GAA  CAC  CCC  GGC  CCA  CTG  CCA  GAA  ACG       341
Pro  Lys  Leu  Ile  Asp  Lys  Thr  Glu  His  Pro  Gly  Pro  Leu  Pro  Glu  Thr
     90                       95                      100

GTC  GTT  GCC  CAT  CTT  GAT  AAA  AGT  CAT  ATT  TGC  GTA  CAT  ACC  TAC  CCG       389
Val  Val  Ala  His  Leu  Asp  Lys  Ser  His  Ile  Cys  Val  His  Thr  Tyr  Pro
105                      110                      115                      120

GAA  AGT  CAT  CCT  GAA  GGC  GGT  TTA  TGT  ACC  TTC  CGC  GCC  GAT  ATT  GAA       437
Glu  Ser  His  Pro  Glu  Gly  Gly  Leu  Cys  Thr  Phe  Arg  Ala  Asp  Ile  Glu
                         125                      130                      135

GTC  TCT  ACC  TGC  GGC  GTG  ATT  TCT  CCG  CTG  AAG  GCG  CTG  AAT  TAC  CTG       485
Val  Ser  Thr  Cys  Gly  Val  Ile  Ser  Pro  Leu  Lys  Ala  Leu  Asn  Tyr  Leu
               140                      145                      150

ATC  CAC  CAG  CTT  GAG  TCC  GAT  ATC  GTA  ACC  ATT  GAT  TAT  CGC  GTG  CGC       533
Ile  His  Gln  Leu  Glu  Ser  Asp  Ile  Val  Thr  Ile  Asp  Tyr  Arg  Val  Arg
          155                      160                      165

GGT  TTT  ACC  CGC  GAC  ATT  AAC  GGT  ATG  AAG  CAC  TTT  ATC  GAC  CAT  GAG       581
Gly  Phe  Thr  Arg  Asp  Ile  Asn  Gly  Met  Lys  His  Phe  Ile  Asp  His  Glu
170                      175                      180

ATT  AAT  TCG  ATT  CAG  AAC  TTT  ATG  TCT  GAC  GAT  ATG  AAG  GCG  CTG  TAT       629
Ile  Asn  Ser  Ile  Gln  Asn  Phe  Met  Ser  Asp  Asp  Met  Lys  Ala  Leu  Tyr
185                      190                      195                      200

GAC  ATG  GTG  GAT  GTG  AAC  GTC  TAT  CAG  GAA  AAT  ATC  TTC  CAT  ACC  AAG       677
Asp  Met  Val  Asp  Val  Asn  Val  Tyr  Gln  Glu  Asn  Ile  Phe  His  Thr  Lys
               205                      210                      215

ATG  TTG  CTT  AAA  GAG  TTC  GAC  CTT  AAG  CAC  TAC  ATG  TTC  CAC  ACC  AAA       725
Met  Leu  Leu  Lys  Glu  Phe  Asp  Leu  Lys  His  Tyr  Met  Phe  His  Thr  Lys
          220                      225                      230

CCG  GAA  GAC  TTA  ACC  GAC  AGC  GAG  CGC  CAG  GAA  ATT  ACC  GCT  GCG  CTG       773
Pro  Glu  Asp  Leu  Thr  Asp  Ser  Glu  Arg  Gln  Glu  Ile  Thr  Ala  Ala  Leu
          235                      240                      245

TGG  AAA  GAA  ATG  CGC  GAG  ATT  TAT  TAC  GGG  CGC  AAT  ATG  CCA  GCT  GTT       821
Trp  Lys  Glu  Met  Arg  Glu  Ile  Tyr  Tyr  Gly  Arg  Asn  Met  Pro  Ala  Val
     250                      255                      260

TAACGGCTCT  GGCGGAGCTC  CCAGGCTCCG  CCAGATCTAT  TTACTTCTGC  TGCACGAAAT              881

TGCGGTAAGC  CGCCACGAC                                                               900
```

( 2 ) INFORMATION FOR SEQ ID NO:10:

( i ) SEQUENCE CHARACTERISTICS:
                ( A ) LENGTH: 1138 base pairs
                ( B ) TYPE: nucleic acid
                ( C ) STRANDEDNESS: double
                ( D ) TOPOLOGY: linear ( i i ) MOLECULE TYPE: DNA (genomic)

( x i ) SEQUENCE DESCRIPTION: SEQ ID NO:10:

```
CTAGAAGGAA  GCTTCACGAA  ATCGGCCCTT  ATTCAAAAAT  AACTTTTAAA  TAATGAATTT      60

TAAATTTTAA  GAAATAATAT  CCAATGAATA  AATGACATGT  AGCATTTTAC  CTAAATATTT     120

CAACTATTTT  AATCCAATAT  TAATTTGTTT  TATTCCCAAC  AATAGAAAGT  CTTGTGCAGA     180

CATTTAATCT  GACTTTTCCA  GTACTAAATA  TTAATTTTCT  GAAGATTTTC  GGGTTTAGTC     240

CACAAGTTTT  AGTGAGAAGT  TTTGCTCAAA  ATTTTAGGTG  AGAAGGTTTG  ATATTTATCT     300

TTTGTTAAAT  TAATTTATCT  AGGTGACTAT  TATTTATTTA  AGTAGAAATT  CATATCATTA     360

CTTTTGCCAA  CTTGTAGTCA  TAATAGGAGT  AGGTGTATAT  GATGAAGGAA  TAAACAAGTT     420

CAGTGAAGTG  ATTAAAATAA  AATATAATTT  AGGTGTACAT  CAAATAAAAA  CCTTAAAGTT     480
```

| | | | | | |
|---|---|---|---|---|---|
| TAGAAAGGCA | CCGAATAATT | TTGCATAGAA | GATATTAGTA | AATTTATAAA | AATAAAAGAA | 540 |
| ATGTAGTTGT | CAAGTTGTCT | TCTTTTTTTT | GGATAAAAAT | AGCAGTTGGC | TTATGTCATT | 600 |
| CTTTTACAAC | CTCCATGCCA | CTTGTCCAAT | TGTTGACACT | TAACTAATTA | GTTGATTCA | 660 |
| TGTATGAATA | CTAAATAATT | TTTTAGGACT | GACTCAAATA | TTTTATATT | ATCATAGTAA | 720 |
| TATTTATCTA | ATTTTTAGGA | CCACTTATTA | CTAAATAATA | AATTAACTAC | TACTATATTA | 780 |
| TTGTTGTGAA | ACAACAACGT | TTTGGTTGTT | ATGATGAAAC | GTACACTATA | TCAGTATGAA | 840 |
| AAATTCAAAA | CGATTAGTAT | AAATTATATT | GAAAATTTGA | TATTTTCTA | TTCTTAATCA | 900 |
| GACGTATTGG | GTTTCATATT | TTAAAAGGG | ACTAAACTTA | GAAGAGAAGT | TTGTTTGAAA | 960 |
| CTACTTTGT | CTCTTTCTTG | TTCCATTTC | TCTCTTAGAT | TTCAAAAGT | GAACTACTTT | 1020 |
| ATCTCTTTCT | TTGTTCACAT | TTTATTTAT | TCTATTATAA | ATATGGCATC | CTCATATTGA | 1080 |
| GATTTTAGA | AATTATTCTA | ATCATTCACA | GTGCAAAAGA | AGATCTAAAG | CCCTAGAG | 1138 |

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:11:

CCCGGATCCA TGAATCTGAA TCGTTTT                                    27

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

CCCGGATCCG CCGTTACGAA ACAGGAA                                    27

( 2 ) INFORMATION FOR SEQ ID NO:13:

( i ) SEQUENCE CHARACTERISTICS:
        ( A ) LENGTH: 318 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

```
AGATCTATCG ATAAGCTTGA TGTAATTGGA GGAAGATCAA AATTTTCAAT CCCCATTCTT      60

CGATTGCTTC AATTGAAGTT TCTCCG ATG GCG CAA GTT AGC AGA ATC TGC AAT     113
                              Met Ala Gln Val Ser Arg Ile Cys Asn
                                1               5

GGT GTG CAG AAC CCA TCT CTT ATC TCC AAT CTC TCG AAA TCC AGT CAA      161
Gly Val Gln Asn Pro Ser Leu Ile Ser Asn Leu Ser Lys Ser Ser Gln
 10              15                  20                  25

CGC AAA TCT CCC TTA TCG GTT TCT CTG AAG ACG CAG CAG CAT CCA CGA      209
Arg Lys Ser Pro Leu Ser Val Ser Leu Lys Thr Gln Gln His Pro Arg
              30                  35                  40

GCT TAT CCG ATT TCG TCG TCG TGG GGA TTG AAG AAG AGT GGG ATG ACG      257
```

|     |     |     |     |     |     |     |     |     |     |     |     |     |     |     |
|---|---|---|---|---|---|---|---|---|---|---|---|---|---|---|
| Ala | Tyr | Pro | Ile<br>45 | Ser | Ser | Ser | Trp | Gly<br>50 | Leu | Lys | Lys | Ser | Gly<br>55 | Met | Thr |

```
TTA  ATT  GGC  TCT  GAG  CTT  CGT  CCT  CTT  AAG  GTC  ATG  TCT  TCT  GTT  TCC     305
Leu  Ile  Gly  Ser  Glu  Leu  Arg  Pro  Leu  Lys  Val  Met  Ser  Ser  Val  Ser
          60                       65                      70

ACG  GCG  TGC  ATG  C                                                              318
Thr  Ala  Cys  Met
          75
```

( 2 ) INFORMATION FOR SEQ ID NO:14:

( i ) SEQUENCE CHARACTERISTICS:
( A ) LENGTH: 1377 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

```
GC  ATG  CTT  CAC  GGT  GCA  AGC  AGC  CGT  CCA  GCA  ACT  GCT  CGT  AAG  TCC      47
    Met  Leu  His  Gly  Ala  Ser  Ser  Arg  Pro  Ala  Thr  Ala  Arg  Lys  Ser
     1              5                        10                       15

TCT  GGT  CTT  TCT  GGA  ACC  GTC  CGT  ATT  CCA  GGT  GAC  AAG  TCT  ATC  TCC     95
Ser  Gly  Leu  Ser  Gly  Thr  Val  Arg  Ile  Pro  Gly  Asp  Lys  Ser  Ile  Ser
               20                       25                       30

CAC  AGG  TCC  TTC  ATG  TTT  GGA  GGT  CTC  GCT  AGC  GGT  GAA  ACT  CGT  ATC    143
His  Arg  Ser  Phe  Met  Phe  Gly  Gly  Leu  Ala  Ser  Gly  Glu  Thr  Arg  Ile
                    35                       40                       45

ACC  GGT  CTT  TTG  GAA  GGT  GAA  GAT  GTT  ATC  AAC  ACT  GGT  AAG  GCT  ATG    191
Thr  Gly  Leu  Leu  Glu  Gly  Glu  Asp  Val  Ile  Asn  Thr  Gly  Lys  Ala  Met
          50                       55                       60

CAA  GCT  ATG  GGT  GCC  AGA  ATC  CGT  AAG  GAA  GGT  GAT  ACT  TGG  ATC  ATT    239
Gln  Ala  Met  Gly  Ala  Arg  Ile  Arg  Lys  Glu  Gly  Asp  Thr  Trp  Ile  Ile
     65                       70                       75

GAT  GGT  GTT  GGT  AAC  GGT  GGA  CTC  CTT  GCT  CCT  GAG  GCT  CCT  CTC  GAT    287
Asp  Gly  Val  Gly  Asn  Gly  Gly  Leu  Leu  Ala  Pro  Glu  Ala  Pro  Leu  Asp
 80                      85                       90                       95

TTC  GGT  AAC  GCT  GCA  ACT  GGT  TGC  CGT  TTG  ACT  ATG  GGT  CTT  GTT  GGT    335
Phe  Gly  Asn  Ala  Ala  Thr  Gly  Cys  Arg  Leu  Thr  Met  Gly  Leu  Val  Gly
                    100                      105                      110

GTT  TAC  GAT  TTC  GAT  AGC  ACT  TTC  ATT  GGT  GAC  GCT  TCT  CTC  ACT  AAG    383
Val  Tyr  Asp  Phe  Asp  Ser  Thr  Phe  Ile  Gly  Asp  Ala  Ser  Leu  Thr  Lys
               115                      120                      125

CGT  CCA  ATG  GGT  CGT  GTG  TTG  AAC  CCA  CTT  CGC  GAA  ATG  GGT  GTG  CAG    431
Arg  Pro  Met  Gly  Arg  Val  Leu  Asn  Pro  Leu  Arg  Glu  Met  Gly  Val  Gln
          130                      135                      140

GTG  AAG  TCT  GAA  GAC  GGT  GAT  CGT  CTT  CCA  GTT  ACC  TTG  CGT  GGA  CCA    479
Val  Lys  Ser  Glu  Asp  Gly  Asp  Arg  Leu  Pro  Val  Thr  Leu  Arg  Gly  Pro
     145                      150                      155

AAG  ACT  CCA  ACG  CCA  ATC  ACC  TAC  AGG  GTA  CCT  ATG  GCT  TCC  GCT  CAA    527
Lys  Thr  Pro  Thr  Pro  Ile  Thr  Tyr  Arg  Val  Pro  Met  Ala  Ser  Ala  Gln
160                      165                      170                      175

GTG  AAG  TCC  GCT  GTT  CTG  CTT  GCT  GGT  CTC  AAC  ACC  CCA  GGT  ATC  ACC    575
Val  Lys  Ser  Ala  Val  Leu  Leu  Ala  Gly  Leu  Asn  Thr  Pro  Gly  Ile  Thr
                    180                      185                      190

ACT  GTT  ATC  GAG  CCA  ATC  ATG  ACT  CGT  GAC  CAC  ACT  GAA  AAG  ATG  CTT    623
Thr  Val  Ile  Glu  Pro  Ile  Met  Thr  Arg  Asp  His  Thr  Glu  Lys  Met  Leu
               195                      200                      205

CAA  GGT  TTT  GGT  GCT  AAC  CTT  ACC  GTT  GAG  ACT  GAT  GCT  GAC  GGT  GTG    671
Gln  Gly  Phe  Gly  Ala  Asn  Leu  Thr  Val  Glu  Thr  Asp  Ala  Asp  Gly  Val
          210                      215                      220
```

| | | | | | | | | | | | | | | | | |
|---|---|---|---|---|---|---|---|---|---|---|---|---|---|---|---|---|
| CGT | ACC | ATC | CGT | CTT | GAA | GGT | CGT | GGT | AAG | CTC | ACC | GGT | CAA | GTG | ATT | 719 |
| Arg | Thr | Ile | Arg | Leu | Glu | Gly | Arg | Gly | Lys | Leu | Thr | Gly | Gln | Val | Ile | |
| 225 | | | | | 230 | | | | | 235 | | | | | | |
| GAT | GTT | CCA | GGT | GAT | CCA | TCC | TCT | ACT | GCT | TTC | CCA | TTG | GTT | GCT | GCC | 767 |
| Asp | Val | Pro | Gly | Asp | Pro | Ser | Ser | Thr | Ala | Phe | Pro | Leu | Val | Ala | Ala | |
| 240 | | | | | 245 | | | | | 250 | | | | | 255 | |
| TTG | CTT | GTT | CCA | GGT | TCC | GAC | GTC | ACC | ATC | CTT | AAC | GTT | TTG | ATG | AAC | 815 |
| Leu | Leu | Val | Pro | Gly | Ser | Asp | Val | Thr | Ile | Leu | Asn | Val | Leu | Met | Asn | |
| | | | | 260 | | | | | 265 | | | | | 270 | | |
| CCA | ACC | CGT | ACT | GGT | CTC | ATC | TTG | ACT | CTG | CAG | GAA | ATG | GGT | GCC | GAC | 863 |
| Pro | Thr | Arg | Thr | Gly | Leu | Ile | Leu | Thr | Leu | Gln | Glu | Met | Gly | Ala | Asp | |
| | | | 275 | | | | | 280 | | | | | 285 | | | |
| ATC | GAA | GTG | ATC | AAC | CCA | CGT | CTT | GCT | GGT | GGA | GAA | GAC | GTG | GCT | GAC | 911 |
| Ile | Glu | Val | Ile | Asn | Pro | Arg | Leu | Ala | Gly | Gly | Glu | Asp | Val | Ala | Asp | |
| | | 290 | | | | | 295 | | | | | 300 | | | | |
| TTG | CGT | GTT | CGT | TCT | TCT | ACT | TTG | AAG | GGT | GTT | ACT | GTT | CCA | GAA | GAC | 959 |
| Leu | Arg | Val | Arg | Ser | Ser | Thr | Leu | Lys | Gly | Val | Thr | Val | Pro | Glu | Asp | |
| | 305 | | | | | 310 | | | | | 315 | | | | | |
| CGT | GCT | CCT | TCT | ATG | ATC | GAC | GAG | TAT | CCA | ATT | CTC | GCT | GTT | GCA | GCT | 1007 |
| Arg | Ala | Pro | Ser | Met | Ile | Asp | Glu | Tyr | Pro | Ile | Leu | Ala | Val | Ala | Ala | |
| 320 | | | | | 325 | | | | | 330 | | | | | 335 | |
| GCA | TTC | GCT | GAA | GGT | GCT | ACC | GTT | ATG | AAC | GGT | TTG | GAA | GAA | CTC | CGT | 1055 |
| Ala | Phe | Ala | Glu | Gly | Ala | Thr | Val | Met | Asn | Gly | Leu | Glu | Glu | Leu | Arg | |
| | | | | 340 | | | | | 345 | | | | | 350 | | |
| GTT | AAG | GAA | AGC | GAC | CGT | CTT | TCT | GCT | GTC | GCA | AAC | GGT | CTC | AAG | CTC | 1103 |
| Val | Lys | Glu | Ser | Asp | Arg | Leu | Ser | Ala | Val | Ala | Asn | Gly | Leu | Lys | Leu | |
| | | | 355 | | | | | 360 | | | | | 365 | | | |
| AAC | GGT | GTT | GAT | TGC | GAT | GAA | GGT | GAG | ACT | TCT | CTC | GTC | GTG | CGT | GGT | 1151 |
| Asn | Gly | Val | Asp | Cys | Asp | Glu | Gly | Glu | Thr | Ser | Leu | Val | Val | Arg | Gly | |
| | | 370 | | | | | 375 | | | | | 380 | | | | |
| CGT | CCT | GAC | GGT | AAG | GGT | CTC | GGT | AAC | GCT | TCT | GGA | GCA | GCT | GTC | GCT | 1199 |
| Arg | Pro | Asp | Gly | Lys | Gly | Leu | Gly | Asn | Ala | Ser | Gly | Ala | Ala | Val | Ala | |
| | 385 | | | | | 390 | | | | | 395 | | | | | |
| ACC | CAC | CTC | GAT | CAC | CGT | ATC | GCT | ATG | AGC | TTC | CTC | GTT | ATG | GGT | CTC | 1247 |
| Thr | His | Leu | Asp | His | Arg | Ile | Ala | Met | Ser | Phe | Leu | Val | Met | Gly | Leu | |
| 400 | | | | | 405 | | | | | 410 | | | | | 415 | |
| GTT | TCT | GAA | AAC | CCT | GTT | ACT | GTT | GAT | GAT | GCT | ACT | ATG | ATC | GCT | ACT | 1295 |
| Val | Ser | Glu | Asn | Pro | Val | Thr | Val | Asp | Asp | Ala | Thr | Met | Ile | Ala | Thr | |
| | | | | 420 | | | | | 425 | | | | | 430 | | |
| AGC | TTC | CCA | GAG | TTC | ATG | GAT | TTG | ATG | GCT | GGT | CTT | GGA | GCT | AAG | ATC | 1343 |
| Ser | Phe | Pro | Glu | Phe | Met | Asp | Leu | Met | Ala | Gly | Leu | Gly | Ala | Lys | Ile | |
| | | | 435 | | | | | 440 | | | | | 445 | | | |
| GAA | CTC | TCC | GAC | ACT | AAG | GCT | GCT | TGATGAGCTC | | | | | | | | 1377 |
| Glu | Leu | Ser | Asp | Thr | Lys | Ala | Ala | | | | | | | | | |
| | | 450 | | | | 455 | | | | | | | | | | |

( 2 ) INFORMATION FOR SEQ ID NO:15:

( i ) SEQUENCE CHARACTERISTICS:
        ( A ) LENGTH: 1029 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 7..1020

( x i ) SEQUENCE DESCRIPTION: SEQ ID NO:15:

| | | | | | | | | | | | | |
|---|---|---|---|---|---|---|---|---|---|---|---|---|
| GGATCC | ATG | AAT | TTG | AAT | CGT | TTT | AAA | CGT | TAT | CCG | TTG | ACC | TTC | GGT | 48 |
| | Met | Asn | Leu | Asn | Arg | Phe | Lys | Arg | Tyr | Pro | Leu | Thr | Phe | Gly | |
| | 1 | | | | 5 | | | | | 10 | | | | | |

| | | | | | | | | | | | | | | | | |
|---|---|---|---|---|---|---|---|---|---|---|---|---|---|---|---|---|
| CCT | TCT | CCC | ATC | ACG | CCC | TTG | AAG | CGC | CTC | AGT | GAA | CAC | TTG | GGT | GGC | 96 |
| Pro | Ser | Pro | Ile | Thr | Pro | Leu | Lys | Arg | Leu | Ser | Glu | His | Leu | Gly | Gly | |
| 15 | | | | | 20 | | | | | 25 | | | | | 30 | |
| AAG | GTC | GAG | CTG | TAT | GCC | AAG | CGT | GAA | GAC | TGC | AAC | AGT | GGC | CTG | GCC | 144 |
| Lys | Val | Glu | Leu | Tyr | Ala | Lys | Arg | Glu | Asp | Cys | Asn | Ser | Gly | Leu | Ala | |
| | | | | 35 | | | | | 40 | | | | | 45 | | |
| TTC | GGC | GGG | AAC | AAA | ACG | CGC | AAG | CTC | GAA | TAT | TTG | ATT | CCC | GAA | GCG | 192 |
| Phe | Gly | Gly | Asn | Lys | Thr | Arg | Lys | Leu | Glu | Tyr | Leu | Ile | Pro | Glu | Ala | |
| | | | 50 | | | | | 55 | | | | | 60 | | | |
| CTC | GAG | CAA | GGC | TGC | GAT | ACC | TTG | GTT | TCC | ATC | GGC | GGC | ATC | CAG | TCG | 240 |
| Leu | Glu | Gln | Gly | Cys | Asp | Thr | Leu | Val | Ser | Ile | Gly | Gly | Ile | Gln | Ser | |
| | | 65 | | | | | 70 | | | | | 75 | | | | |
| AAC | CAG | ACC | CGC | CAG | GTG | GCC | GCC | GTT | GCC | GCT | CAC | CTG | GGC | ATG | AAG | 288 |
| Asn | Gln | Thr | Arg | Gln | Val | Ala | Ala | Val | Ala | Ala | His | Leu | Gly | Met | Lys | |
| | | 80 | | | | | 85 | | | | | 90 | | | | |
| TCG | GTG | CTG | GTC | GAG | GAA | AAC | TGG | GTG | AAC | TAC | TCC | GAT | GCG | GTG | TAT | 336 |
| Ser | Val | Leu | Val | Glu | Glu | Asn | Trp | Val | Asn | Tyr | Ser | Asp | Ala | Val | Tyr | |
| 95 | | | | | 100 | | | | | 105 | | | | | 110 | |
| GAC | CGC | GTT | GGC | AAT | ATC | GAA | ATG | TCT | CGC | ATC | ATG | GGC | GCC | GAG | GTA | 384 |
| Asp | Arg | Val | Gly | Asn | Ile | Glu | Met | Ser | Arg | Ile | Met | Gly | Ala | Glu | Val | |
| | | | | 115 | | | | | 120 | | | | | 125 | | |
| CGA | CTG | GAC | GCC | GCC | GGG | TTC | GAT | ATC | GGC | ATT | CGG | CCC | AGC | TGG | GAG | 432 |
| Arg | Leu | Asp | Ala | Ala | Gly | Phe | Asp | Ile | Gly | Ile | Arg | Pro | Ser | Trp | Glu | |
| | | | 130 | | | | | 135 | | | | | 140 | | | |
| AAG | GCC | ATG | GAC | GAT | GTG | GTG | GCG | CGG | GGT | GGC | AAG | CCG | TTC | CCG | ATA | 480 |
| Lys | Ala | Met | Asp | Asp | Val | Val | Ala | Arg | Gly | Gly | Lys | Pro | Phe | Pro | Ile | |
| | | 145 | | | | | 150 | | | | | 155 | | | | |
| CCG | GCG | GGT | TGT | TCC | GAA | CAC | CCC | TAC | GGC | GGC | CTT | GGG | TTC | GTC | GGC | 528 |
| Pro | Ala | Gly | Cys | Ser | Glu | His | Pro | Tyr | Gly | Gly | Leu | Gly | Phe | Val | Gly | |
| | | 160 | | | | | 165 | | | | | 170 | | | | |
| TTT | GCC | GAG | GAA | GTG | CGA | GAG | CAG | GAA | AAA | CAA | CTG | GGG | TTC | ACG | TTC | 576 |
| Phe | Ala | Glu | Glu | Val | Arg | Glu | Gln | Glu | Lys | Gln | Leu | Gly | Phe | Thr | Phe | |
| 175 | | | | | 180 | | | | | 185 | | | | | 190 | |
| GAC | TAC | ATC | GTG | GTC | TGC | TCT | GTG | ACC | GGC | AGT | ACC | CAG | GCC | GGC | ATG | 624 |
| Asp | Tyr | Ile | Val | Val | Cys | Ser | Val | Thr | Gly | Ser | Thr | Gln | Ala | Gly | Met | |
| | | | | 195 | | | | | 200 | | | | | 205 | | |
| GTC | GTC | GGT | TTC | GCC | GCG | GAC | GGC | CGT | TCG | AAG | AAC | GTT | ATC | GGC | ATT | 672 |
| Val | Val | Gly | Phe | Ala | Ala | Asp | Gly | Arg | Ser | Lys | Asn | Val | Ile | Gly | Ile | |
| | | | 210 | | | | | 215 | | | | | 220 | | | |
| GAT | GCC | TCG | GCC | AAG | CCG | GAG | CAA | ACC | AAG | GCA | CAG | ATC | CTG | CGT | ATC | 720 |
| Asp | Ala | Ser | Ala | Lys | Pro | Glu | Gln | Thr | Lys | Ala | Gln | Ile | Leu | Arg | Ile | |
| | | 225 | | | | | 230 | | | | | 235 | | | | |
| GCC | CGG | CAC | ACC | GCA | GAG | TTG | GTG | GAA | CTG | GGC | CGT | GAG | ATC | ACC | GAA | 768 |
| Ala | Arg | His | Thr | Ala | Glu | Leu | Val | Glu | Leu | Gly | Arg | Glu | Ile | Thr | Glu | |
| | | 240 | | | | | 245 | | | | | 250 | | | | |
| GAC | GAC | GTG | GTG | CTC | GAT | ACA | CGT | TTT | GCC | TAC | CCG | GAA | TAC | GGT | TTG | 816 |
| Asp | Asp | Val | Val | Leu | Asp | Thr | Arg | Phe | Ala | Tyr | Pro | Glu | Tyr | Gly | Leu | |
| 255 | | | | | 260 | | | | | 265 | | | | | 270 | |
| CCC | AAC | GAA | GGC | ACG | CTG | GAA | GCC | ATT | CGT | TTG | TGC | GGG | AGC | CTG | GAA | 864 |
| Pro | Asn | Glu | Gly | Thr | Leu | Glu | Ala | Ile | Arg | Leu | Cys | Gly | Ser | Leu | Glu | |
| | | | | 275 | | | | | 280 | | | | | 285 | | |
| GGT | GTG | CTG | ACC | GAT | CCG | GTG | TAC | GAG | GGC | AAA | TCC | ATG | CAC | GGG | ATG | 912 |
| Gly | Val | Leu | Thr | Asp | Pro | Val | Tyr | Glu | Gly | Lys | Ser | Met | His | Gly | Met | |
| | | | 290 | | | | | 295 | | | | | 300 | | | |
| ATT | GAA | ATG | GTC | CGC | CGT | GGC | GAG | TTC | CCC | GAA | GGC | TCC | AAA | GTG | CTG | 960 |
| Ile | Glu | Met | Val | Arg | Arg | Gly | Glu | Phe | Pro | Glu | Gly | Ser | Lys | Val | Leu | |
| | | 305 | | | | | 310 | | | | | 315 | | | | |
| TAT | GCG | CAC | TTG | GGT | GGG | GCG | CCT | GCG | CTG | AAT | GCC | TAC | AGC | TTC | CTG | 1008 |
| Tyr | Ala | His | Leu | Gly | Gly | Ala | Pro | Ala | Leu | Asn | Ala | Tyr | Ser | Phe | Leu | |
| | | 320 | | | | | 325 | | | | | 330 | | | | |

```
TTT CGT AAC GGC GGATCCGGG                                                                    1029
Phe Arg Asn Gly
335
```

( 2 ) INFORMATION FOR SEQ ID NO:16:

( i ) SEQUENCE CHARACTERISTICS:
        ( A ) LENGTH: 338 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Asn Leu Asn Arg Phe Lys Arg Tyr Pro Leu Thr Phe Gly Pro Ser
 1               5                  10                 15

Pro Ile Thr Pro Leu Lys Arg Leu Ser Glu His Leu Gly Gly Lys Val
             20                  25                 30

Glu Leu Tyr Ala Lys Arg Glu Asp Cys Asn Ser Gly Leu Ala Phe Gly
         35                  40                  45

Gly Asn Lys Thr Arg Lys Leu Glu Tyr Leu Ile Pro Glu Ala Leu Glu
     50                  55                  60

Gln Gly Cys Asp Thr Leu Val Ser Ile Gly Gly Ile Gln Ser Asn Gln
65                  70                  75                  80

Thr Arg Gln Val Ala Ala Val Ala Ala His Leu Gly Met Lys Ser Val
                 85                  90                  95

Leu Val Glu Glu Asn Trp Val Asn Tyr Ser Asp Ala Val Tyr Asp Arg
             100                 105                 110

Val Gly Asn Ile Glu Met Ser Arg Ile Met Gly Ala Glu Val Arg Leu
         115                 120                 125

Asp Ala Ala Gly Phe Asp Ile Gly Ile Arg Pro Ser Trp Glu Lys Ala
130                 135                 140

Met Asp Asp Val Val Ala Arg Gly Gly Lys Pro Phe Pro Ile Pro Ala
145                 150                 155                 160

Gly Cys Ser Glu His Pro Tyr Gly Gly Leu Gly Phe Val Gly Phe Ala
                 165                 170                 175

Glu Glu Val Arg Glu Gln Glu Lys Gln Leu Gly Phe Thr Phe Asp Tyr
             180                 185                 190

Ile Val Val Cys Ser Val Thr Gly Ser Thr Gln Ala Gly Met Val Val
         195                 200                 205

Gly Phe Ala Ala Asp Gly Arg Ser Lys Asn Val Ile Gly Ile Asp Ala
210                 215                 220

Ser Ala Lys Pro Glu Gln Thr Lys Ala Gln Ile Leu Arg Ile Ala Arg
225                 230                 235                 240

His Thr Ala Glu Leu Val Glu Leu Gly Arg Glu Ile Thr Glu Asp Asp
                 245                 250                 255

Val Val Leu Asp Thr Arg Phe Ala Tyr Pro Glu Tyr Gly Leu Pro Asn
             260                 265                 270

Glu Gly Thr Leu Glu Ala Ile Arg Leu Cys Gly Ser Leu Glu Gly Val
         275                 280                 285

Leu Thr Asp Pro Val Tyr Glu Gly Lys Ser Met His Gly Met Ile Glu
290                 295                 300

Met Val Arg Arg Gly Glu Phe Pro Glu Gly Ser Lys Val Leu Tyr Ala
305                 310                 315                 320

His Leu Gly Gly Ala Pro Ala Leu Asn Ala Tyr Ser Phe Leu Phe Arg
                 325                 330                 335
```

Asn Gly ( 2 ) INFORMATION FOR SEQ ID NO:17:

( i ) SEQUENCE CHARACTERISTICS:
        ( A ) LENGTH: 597 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

```
TCATCAAAAT   ATTTAGCAGC   ATTCCAGATT   GGGTTCAATC   AACAAGGTAC   GAGCCATATC        60
ACTTTATTCA   AATTGGTATC   GCCAAAACCA   AGAAGGAACT   CCCATCCTCA   AAGGTTTGTA       120
AGGAAGAATT   CTCAGTCCAA   AGCCTCAACA   AGGTCAGGGT   ACAGAGTCTC   CAAACCATTA       180
GCCAAAAGCT   ACAGGAGATC   AATGAAGAAT   CTTCAATCAA   AGTAAACTAC   TGTTCCAGCA       240
CATGCATCAT   GGTCAGTAAG   TTTCAGAAAA   AGACATCCAC   CGAAGACTTA   AAGTTAGTGG       300
GCATCTTTGA   AAGTAATCTT   GTCAACATCG   AGCAGCTGGC   TTGTGGGGAC   CAGACAAAAA       360
AGGAATGGTG   CAGAATTGTT   AGGCGCACCT   ACCAAAAGCA   TCTTTGCCTT   TATTGCAAAG       420
ATAAAGCAGA   TTCCTCTAGT   ACAAGTGGGG   AACAAAATAA   CGTGGAAAAG   AGCTGTCCTG       480
ACAGCCCACT   CACTAATGCG   TATGACGAAC   GCAGTGACGA   CCACAAAAGA   ATTCCCTCTA       540
TATAAGAAGG   CATTCATTCC   CATTTGAAGG   ATCATCAGAT   ACTAACCAAT   ATTTCTC          597
```

CONTROL OF FRUIT RIPENING AND SENESCENCE IN PLANTS

This is a continuation-in-part of our application having U.S. Ser. No. 07/632,440 filed on Dec. 26, 1990 entitled "Control of Fruit Ripening and Senescence in Plants" now abandoned.

FIELD OF THE INVENTION

This invention relates in general to plant molecular biology and more particularly to a method for controlling the ripening of fruit and vegetables as well as controlling the effects of senescence in plants and recombinant DNA molecules capable of affecting the desired control.

BACKGROUND OF THE INVENTION

One of the major problems facing the fruit, vegetable and cut flower industry is the loss of a considerable amount of goods due to spoilage. It is estimated that 12 to 20 percent of the fruit and vegetable products become spoiled from the time they leave the farm until they get to the retail or processing outlets. In the cut flower industry, senescence (the wilting or dying) of the flower before it can be effectively marketed is a significant problem. The spoiling or senescence process observed in fruits, vegetables and cut flowers results in a number of undesirable problems. Chief among these problems is the short harvesting season for the goods and the short shelf life of the goods following the harvest. Furthermore, these spoilage losses ultimately result in a higher cost of the goods to the consumer.

A primary cause of the spoilage of fruits and vegetables is the natural ripening process of the fruit or vegetable. As the fruit or vegetable becomes more ripe it becomes softer and more easily bruised and susceptible to disease or other spoilage causing agents. It is known that ethylene production in the plant stimulates the fruit ripening process and is the key component in the ripening of fruits and vegetables. Others have attempted to control the ripening of fruits and vegetables in an attempt to extend the shelf life and/or harvesting season of the goods. Many of these attempts have been topical applications of chemicals to the fruit or vegetable itself. These chemical solutions have involved direct applications to the plant in the field or post-harvest applications to the fruit or vegetable itself. Several of these methods are discussed in U.S. Pat. No. 4,957,757 or U.S. Pat. No. 4,851,035. Due to the increasing importance of reducing additional stresses on the environment, a non-chemical means for controlling ripening would be advantageous and beneficial to the industry.

More recently, researchers have used a molecular biology approach to block ethylene synthesis in plants in an attempt to control the ripening of tomatoes. This approach involved transforming a tomato plant with an antisense gene that inhibited the synthesis of ethylene. The antisense gene produces (−) strand RNA that lowers the steady state levels of the (+) strand mRNA encoding a polypeptide involved in the conversion of 1-aminocyclopropane-1-carboxylic acid (ACC) to ethylene by the ethylene forming enzyme ACC oxidase. (Hamilton et al. 1990) While this method exhibits some degree of utility, it would be neither easy nor efficient to apply this technology to other plants, because the antisense gene would probably be species and gene specific which would entail obtaining a different antisense gene for each species of plant desired to be transformed.

Thus a need exists in the fruit, vegetable and cut flower industries for a non-chemical method of controlling fruit ripening and senescence in plants that can easily and efficiently be utilized across a wide variety of plant species.

SUMMARY OF THE INVENTION

A method for controlling the ripening of fruits and vegetables as well as a method for controlling senescence in cut flowers is presented. In general, the method involves expressing an ACC metabolizing enzyme in the desired plant tissue which lowers the level of ACC in the tissue which thereby reduces the level of ethylene in the desired plant tissue. More particularly, the method comprises transforming plant cells with a chimeric gene comprising a promoter that functions in plant cells to cause the production of an RNA sequence, a structural DNA sequence that causes the production of an RNA sequence that encodes an ACC deaminase enzyme and a 3' non-translated region that functions in plant cells to cause the addition of a stretch of polyadenyl nucleotides to the 3' end of the RNA sequence, with the promoter being heterologous with respect to the structural coding sequence, and then growing the plant to maturity. The expression of the ACC deaminase in the fruit delays the ripening process which provides an extended harvesting season and an extended shelf life for the goods. Likewise, expression of an ACC metabolizing enzyme in floral species suitable for use in the cut flower industry delays senescence of the flowers, thus extending the shelf life and marketability of the flowers.

In another aspect of the present invention, a recombinant, double stranded DNA molecule comprising a promoter that functions in plant cells to cause the production of an RNA sequence, a structural DNA sequence that encodes an ACC deaminase enzyme and a 3' non-translated region that functions in plant cells to cause the addition of a stretch of polyadenyl nucleotides to the 3' end of the RNA sequence, where the promoter is heterologous with respect to the structural DNA sequence, is also provided that enables one to obtain plants capable of expressing ACC deaminase in order to control ripening and senescence. The expression of the ACC deaminase in the plant cells extends the harvesting season and the shelf life of the goods by reducing the production of ethylene in the plants.

Among the many aims and objects of the present invention, one primary object is to provide a method of controlling ripening and senescence in plants utilizing a molecular biology technique that is efficiently and broadly applicable to many plant species.

Another object of the present invention is to provide a method for extending the harvesting season and shelf life of fruits, vegetables and flowers by controlling the production of ethylene in the plant by lowering the steady state levels of ACC using an ACC metabolizing enzyme, such as ACC deaminase or ACC malonyl transferase, expressed in the plant.

It is a further object of the present invention to reduce the synthesis of ethylene in plants by expressing the enzyme ACC deaminase in the plant.

It is still another object of the present invention to extend the market life of cut flowers by expressing the enzyme ACC deaminase in the flower thereby reducing the senescence effects of ethylene synthesis in the flower.

It is a still further object of the present invention to provide transformed plants expressing an enzyme, ACC deaminase, in the plant so as to delay ripening of the fruit of the plant whether the fruit is allowed to ripen on the vine or if picked at an unripe stage of development to be ripened at a later time.

It is also a primary aim of the present invention to provide a fruit-bearing plant capable of expressing ACC deaminase specifically in the fruit of the plant.

Other and further objectives and aims of the invention will be made clear or become apparent from the following description and claims when read in light of the accompanying drawings.

BRIEF DESCRIPTION OF THE DRAWINGS

FIG. 1 illustrates the contents of the bacterial collection used to screen for ACC deaminase.

FIG. 2 shows the nucleotide sequence of the ACC deaminase gene from Pseudomonas chloroaphis (isolate 6G5) (SEQ ID NO:1).

FIG. 14 illustrates the nucleotide sequence of the fruit specific promoter E8 with the 5' HindIII and 3'BglII restriction sites underlined (SEQ ID NO:10).

FIG. 15 illustrates the nucleotide sequence of the S-adenosyl methionine (SAM) decarboxylase gene (SEQ ID NO:9).

FIG. 16 illustrates the nucleotide sequence of the ACC synthase gene (SEQ ID NO:8).

FIG. 17 illustrates the nucleotide sequence of the ACC deaminase gene isolated from isolate 3F2. (SEQ ID NO:15)

FIG. 20 illustrates the DNA sequence of the chloroplast transit peptide CTP2. (SEQ ID NO:13)

FIG. 21 illustrates the DNA sequence of the CP4 synthetic 5-enolpyruvyl-3-shikimate phosphate synthase (EPSPS) gene. (SEQ ID NO:14)

FIG. 22 illustrates the DNA sequence of a full-length transcript promoter from figwort mosaic virus (SEQ ID NO:17).

DETAILED DESCRIPTION OF THE PREFERRED EMBODIMENTS

Figure 3:
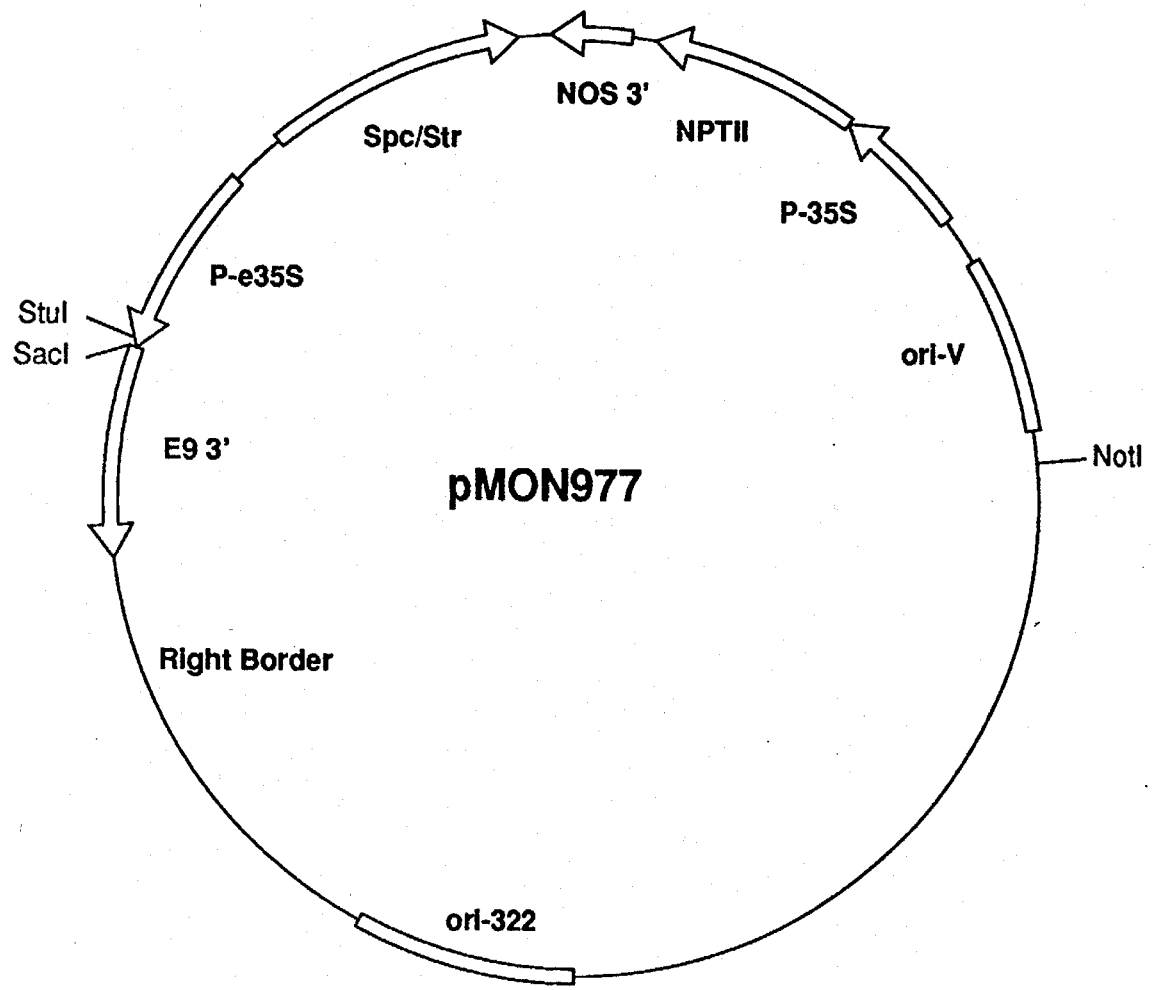
FIG. 3 illustrates a plasmid map of pMON977.

The metabolic pathway for the production of ethylene in plants is as follows:

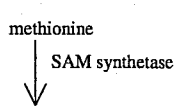

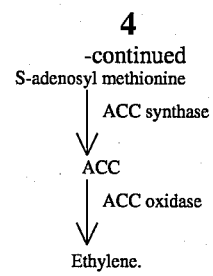

In order to inhibit the biosynthesis of ethylene in plant tissues, one possible method would be to metabolize 1-aminocyclopropane-1-carboxylic acid (hereinafter ACC) and remove it from the metabolic pool. While it was unknown whether any ACC metabolizing enzyme would be capable of reducing the level of ACC sufficient to inhibit ethylene biosynthesis, this approach was investigated. A number of enzymes are capable of metabolizing ACC. Examples of ACC metabolizing enzymes are ACC deaminase and ACC malonyl transferase. The ACC deaminase enzyme metabolizes ACC by converting it to α-ketobutyrate and ammonia. Thus, if the enzyme ACC deaminase, or another ACC metabolizing enzyme, having sufficient kinetic capabilities can be expressed at sufficient levels in the plant, the synthesis of ethylene would be inhibited by the removal of ACC from the metabolic pool in the tissues where the ACC metabolizing enzyme is being expressed. A significant aspect of the present invention is to provide a mechanism for delaying the ripening of fruit or senescence in plants by reducing the steady state levels of ACC in the plant tissues which reduces the level of ethylene in the plant tissues. It is preferred that the steady state concentrations of ethylene or ACC in the plant be reduced by at least about 70% from normal levels in a non-modified cultivar. Preferably, the ethylene or ACC concentrations are reduced by at least about 90% from normal levels. It is believed that the reduction of the steady state levels of ACC or ethylene in a plant or the fruit of a plant can be achieved by various methods, all of which are considered within the scope of the instant invention.

Regarding the delaying of ripening of fruit, it is preferred that the fruit be delayed from ripening on the vine by 1 to 30 days. This delay is to be measured from the onset of ripening and, specifically with respect to tomato, from when the fruit reaches the breaker stage of ripening. Likewise, the fruit is preferably delayed in ripening from 1 to 90 days following detachment from the vine and more preferably between 5 and 30 days. With respect to tomato, this delay in ripening is measured from the time of detachment of the fruit from the vine when the fruit is removed at the mature green or breaker stage of ripening. It is to be understood that the delay in ripening after detachment from the vine can be extended beyond the terms described by cold storage or other methods known in the art.

The enzyme ACC deaminase was chosen for further experimentation. ACC deaminase is not known in the art to be produced or expressed naturally in plants. Therefore, in order to pursue a method of inhibiting ethylene synthesis in plants by degrading ACC, an ACC deaminase encoding gene must be identified and then be made capable of being expressed in plants.

ACC deaminase is known to be expressed in certain microorganisms (Honma, M. and Shimomura, T. 1978). In order to isolate an ACC deaminase enzyme, a bacterial screen to isolate bacteria expressing the enzyme can be designed to identify such a bacteria or microorganism. Other methods for identifying an ACC deaminase enzyme, such as screening strains of yeast or fungi, would be equally applicable and routine to one of skill in the art. The following is a description of a bacterial screen that identified bacteria expressing an ACC deaminase enzyme.

A collection of bacterial strains (Drahos, D. 1988) was screened for organisms that are capable of degrading ACC. This bacterial collection was composed of 597 microorganisms. The majority of the organisms were fluorescent Pseudomonas species with the remaining being microbes typically found in the soil. A description of the bacterial collection is found in FIG. 1. The screen was designed to select for microorganisms that would grow in a minimal medium containing ACC at 3.0 mM as the sole source of nitrogen. A sample of each bacteria in the bacterial collection was grown individually in 96-well microliter dishes at 30° C. for four days. Each well contained 0.2 ml of DF medium supplemented with ACC. DF medium was made by combining in 1 liter of autoclaved water, 1 ml each of Reagent A, Reagent B, Reagent C and 5 mg of thiamine HCl. Reagent A is made up of 1 mg $H_3BO_3$, 1 mg $MnSO_4.7H_2O$, 12.5 mg $ZnSO_4.7H_2O$, 8 mg $CuSO_4.5H_2O$ and 1.7 mg $NaMoO_3.3H_2O$ in 100 mls of autoclaved water. Reagent B is made up of 0.1 g $FeSO_4.7H_2O$ in 100 mls of autoclaved water. Reagent C contains 20 g of $MgSO_4.7H_2O$ in 100 mls of autoclaved water. To the combined solution, carbon sources glucose, gluconate and citrate are added to final concentrations of 0.1% (w/v) each, inorganic phosphate is added to a final concentration of 1.0 mM (w/v) and ACC is added as the sole nitrogen source to a 3.0 mM (w/v) final concentration. Finally, Yeast Extract (DIFCO) is added to a final concentration of 0.01% (w/v).

Based on this screen, three organisms were identified as being capable of growing on ACC-containing medium. Their ability to grow on ACC-containing minimal medium was confirmed by regrowth in 300 ml liquid cultures of the same medium. The two isolates that grew best on ACC were chosen for further characterization. These two isolates were designated 3F2 and 6G5. Both of these organisms were determined to be Pseudomonads as was the organism not chosen for further characterization. Both of the selected organisms were screened for ACC deaminase enzyme activity by an in vitro assay described below. The 6G5 isolate was chosen for further experimentation. The 6G5 bacterium was identified as a *Pseudomonas chloroaphis* strain by gas chromatography analysis of fatty acid methyl esters as described in Miller (1982). From the above screen results, it is apparent that other bacterial strains could be identified which degrade ACC by performing more extensive screens. Thus, other ACC deaminases and those identified in the screen but not utilized for further experimentation are considered to be within the scope of the present invention.

A number of novel organisms capable of degrading ACC have also been isolated from diverse soil samples. These organisms were isolated on the basis of being able to grow on minimal medium with ACC as the sole nitrogen source. Soil samples were collected from St. Charles (Mo., USA), Sarawak (Malaysia), Iquitos (Peru), San Juan (Puerto Rico) and Mujindi (Tanzania). One gram of each soil sample was suspended into 99 ml of a Dilution buffer bottle (Fisher), shaken well and the soil suspension was diluted 1:100 before plating. Final dilution of the soil samples was $10^{-4}$. One hundred (100) microliters of the diluted sample was spread on the isolation media in petri-plates (100×15 mm) with a hockey-stick glass rod. The isolation media contains a minimal salt base with $K_2HPO_4$ (10 g/L), $MgSO_4.7H_2O$ (5 g/L), and trace metals: $FeSO_4$ (1 mg/L), $MnCl_2$ (1 mg/L), $CUSO_4$ (1 mg/L), $ZnSO_4$ (1 mg/L), $CaCl_2$ (1 mg/L). The pH of the base was adjusted to 7.0, before autoclaving, with 1N HCl. Noble agar (Difco) was used as the solidifying agent (1.5%). Any of the following three media may be used for isolation of ACC degrading microorganisms; (1) base+ glucose (5 g/L)+ACC (0.1 to 1.0 g/L); (2) base+$NH_4NO_3$ (5 g/L)+ACC (1 g/L); (3) base+ACC (0.1 to 1.0 g/L). ACC, glucose, $NH_4NO_3$ were dissolved in distilled water, filter-sterilized and added into the autoclaved base media cooling at 50° C. Plates were incubated at 30° C. for 1 week.

ACC was added to some of the soil samples obtained from St. Charles to enrich for ACC degrading bacteria in the soil. In these experiments, ACC (250 mg) was added into 50 ml of dilution buffer containing 0.5 g of St. Charles soil in a 250 ml Erlenmeyer flask. The flask was incubated on a rotary shaker (250 rpm, 30° C.) for 3 days. The ACC enriched sample was then plated as previously described for non-enriched samples. Bacterial colonies capable of growth in the presence of ACC on plates were then isolated into pure cultures and grown in test tubes (20×150 mm) containing 5 ml of the following medium: $KH_2PO_4$ (4 g/L), $K_2HPO_4$ (6.5 g/L), $MgSO_4.7H_2O$ (1 g/L), trace metals (same as isolation media), and ACC (0.3 g/L). Glucose (2 g/L) may be added to assist the growth of the bacteria. Bacterial strains which grew in the minimal salt medium with ACC as the sole carbon and nitrogen sources are listed in Table I.

TABLE I

| Strain | Line # | Source |
| --- | --- | --- |
| 388 | B27444 | St. Charles (ACC enriched) |
| 391 | B27447 | Malaysia |
| 392 | B27448 | Peru |
| 393 | B27449 | St. Charles |
| 401 | B27457 | St. Charles (ACC enriched) |
| T44 | B27817 | Tanzania |
| PR-1 | B27813 | Puerto Rico |

All of these organisms were shown to express ACC deaminase by two criteria. The first was that extracts from all of the organisms were capable of converting ACC to α-ketobutyric acid and the second was that all contained a protein of approximately 37,000 daltons that strongly cross-reacted with an antibody raised against the 6G5 ACC deaminase protein. To further demonstrate the equivalence of these organisms, kinetic parameters were determined for each of the isolated ACC deaminase enzymes.

The $K_m$ for the ACC deaminases isolated from the various soil sources was determined using crude, desalted extracts. Individual strains of bacteria were grown in liquid media containing 4 g $KH_2PO_4$, 6.5 g $K_2HPO_4$, 1 g $MgSO_4.7H_2O$, 2 g glucose, 1 mg $FeSO_4$, 1 mg $MnCl_2$, 1 mg $ZnSO_4$, 1 mg $CuSO_4$, 1 mg $CaCl_2$, and 300 mg ACC, all in 1 liter $H_2O$. Cells were grown for 2 to 3 days at 30° C. Cells were pelleted by centrifugation and resuspended in extraction buffer containing 0.1M phosphate, pH 7.5, 1 mM EDTA, 0.1% β-mercaptoethanol. The cells were broken with a French Press, 1000 psi, and the cell debris was pelleted by centrifugation. The supernatants were desalted on Sephadex G-25 columns pre-equilibrated with extraction buffer, which resulted in a crude, desalted extract. Glycerol was added to the extract (20% v/v) and enzyme solutions were stored at −20° C. ACC deaminase enzyme assays were conducted as described in the Examples to follow. The assay mixture contained 100 μl of 0.2M Tris buffer, pH 8.0, 30 μl of 500 mM ACC solution, and enzyme solution to make a final volume of 200 μl. Reactions were run for 10 minutes at 30° C. The reaction was stopped with 1.8 ml of 2N HCl. After adding 300 μl 0.1% 2,4-dinitrophenylhydrazine, the mixture was incubated for 15 minutes at 30° C. The solution was then made basic by adding 2 ml of 2N NaOH. The optical density of the resulting brownish-red solution was determined at 540 nm with a spectrophotometer.

The kinetic value, $K_m$, for ACC deaminase was determined against ACC as the enzyme substrate for each of the ACC deaminases isolated. ACC deaminase activity was shown to be linear with respect to enzyme concentration using saturating levels of ACC (50 mM). An estimated $K_m$ was determined for each extracted enzyme with ACC at sub-saturating concentrations. Activity was shown to be linear over time with respect to ACC concentration for the concentrations used to determine the actual $K_m$ values. Actual $K_m$ values were then determined for each extract using ACC concentrations between 0.2× and 2× of the estimated $K_m$, or ACC concentrations between 1 and 10 mM ACC. $K_m$ values were calculated from double reciprocal plots, plotting the reciprocal of the substrate concentration on the x-axis and the reciprocal of the velocity (α-ketobutyrate formed) on the y-axis. The x-intercept (at y equals 0) is equal to $-1/K_m$. The $K_m$ values for the ACC deaminases extracted from nine different strains were determined and were generally within 3-fold of one another (from ~4 to ~12 mM). The $K_m$ data demonstrates that essentially all ACC deaminases are functionally equivalent and can be used in the present invention. The $K_m$ values for ACC deaminases from numerous isolates are listed in Table II.

TABLE II

Kinetic Values for Different Bacterial Isolates

| Strain | $K_m$ [mM ACC] |
| --- | --- |
| 6G5 | 9.0 |
| 3F2 | 5.8 |
| 388 | 8.6 |
| 391 | 17.4 |
| 392 | 7.1 |
| 393 | 5.9 |
| 401 | 7.8 |
| T44 | 11.8 |
| PR-1 | 4.1 |

Once an isolate capable of degrading ACC is selected for further study, the gene encoding the ACC deaminase must be isolated. A general strategy for isolation and purification of the ACC deaminase gene from the selected Pseudomonas strain 6G5 is as follows. Isolate 6G5 is an exemplary embodiment for further illustrative embodiments, but other isolates would be useful as well. A cosmid bank of the Pseudomonas strain 6G5 is constructed, cloned and introduced into E. coli. The clone carrying the ACC deaminase gene is identified by selection on minimal media containing ACC as the sole nitrogen source. The coding region of the ACC deaminase gene is then identified and sequenced. Cloning and genetic techniques, unless otherwise indicated, are generally those described by Sambrook et al. (1989). While this strategy was utilized to obtain the ACC deaminase gene from the 6G5 strain, other strategies could be employed with similar success and are considered to be within the scope of the invention. The detailed procedure for isolating the ACC deaminase gene from the 6G5 strain is set forth below.

The cell pellet from a 200 ml L-Broth (Miller 1972) late log phase culture of strain 6G5 was resuspended in 10 ml of Solution I (Birnboim and Doly 1979) in order to obtain chromosomal DNA. Sodium dodecylsulfate (SDS) is added to a final concentration of 1% and the suspension subjected to three freeze-thaw cycles, each consisting of immersion in dry ice for 15 minutes and in water at 70° C. for 10 minutes. The lysate is then extracted four times with equal volumes of phenol:chloroform (1:1; phenol saturated with TE buffer at pH8.0) (TE=10 mM Tris; 1.0 mM EDTA) and the phases separated by centrifugation (15000 g; 10 minutes). The ethanol-precipitable material is pelleted from the supernatant by brief centrifugation (8000 g; 5 minutes) following addition of two volumes of ethanol. The pellet is resuspended in 5 mls of TE buffer and dialyzed for 16 hours at 4° C. against 2 liters of TE buffer. This preparation yields a 5 ml DNA solution of about 552 µg/ml.

Three 50 µg fractions of the Pseudomonas 6G5 DNA are then partially digested with EcoRI to generate fragments greater than 20 Kb. The three 50 µg fractions are digested with 0.125 units, 0.062 units, and 0.032 units, respectively, of EcoRI per µg DNA in a total volume of 1.25 ml each and incubated at 37° C. for 30 minutes. The fractions are pooled and extracted once with an equal volume of 1:1 phenol:chloroform saturated with TE buffer at pH 7.6 to remove the enzyme. The DNA is precipitated with two volumes of ethanol and pelleted by centrifugation (12000 g, 5 minutes). The dried DNA pellet is resuspended in 500 µl TE buffer, and layered on top of a sucrose gradient. The 10%–40% sucrose gradient is prepared in seven 5.5 ml layers using 5% sucrose increments in 50 Mm Tris pH8.0, 5 mM EDTA, 0.5 mM NaCl. The gradients are centrifuged at 26,000 rpm for 18 hours in a Beckmann SW28 rotor. The tube is punctured on the bottom and 1 ml fractions are collected. From each fraction, 20 µl aliquots are run on a 1% agarose gel along with lambda DNA HindIII digested size standards. The fractions which contain DNA fragments greater than 20 Kb are combined. In the instant description, seven fractions were combined. The pooled sample is desalted and concentrated over Amicon Centricon-10® columns. The 0.5 ml concentrated sample is rinsed with 2 ml TE buffer, and again concentrated to 0.5 ml. The DNA sample is precipitated with 1 ml ethanol and the dry pellet resuspended in 50 µl TE buffer. To estimate the DNA yield, 2 µl of the sample is run on a 1% agarose gel along with 0.8 µg lambda DNA cut with BstEII as a standard. From the gel, the concentration is estimated at 35 ng/µl of the Pseudomonas 6G5 DNA partial EcoRI fragments which are greater than 20 Kb.

A cosmid bank is constructed using the vector pMON17016. This vector is a derivative of the phage lambda cos plasmid pHC79 (Hohn and Collins 1980). The pMON17016 plasmid is constructed by introducing the HindIII-BglII fragment from pT7-7 (Tabor and Richardson 1985) containing the gene 10 promoter region from phage T7 into the HindIII-BamHI cut pHC79. The clone interrupts and inactivates the tetracycline resistance gene of pHC79 leaving the ampicillin resistance gene intact. The introduced T7 promoter is not required for the function of the cosmid clone. The pMON17016 vector is cut with EcoRI and treated with calf alkaline phosphatase (CAP) in preparation for cloning. The vector and target sequences are ligated as follows. 1.25 µg (25 µl of 50 ng/µl) of the pMON17016 vector DNA (EcoRI/CAP) is combined with 0.63 µg (18 µl of 35 ng/µl) of size fractionated 6G5 EcoRI fragments, and precipitated with two volumes of ethanol. The sample is centrifuged and the dry DNA pellet resuspended in 6 µl H₂O. To this solution, 1 µl of the 10× ligation buffer (250 mM Tris-HCl pH 8.0, 100 mM MgCl₂, 100 mM Dithiothreitol, 2 mM Spermidine), 2 µl of 100 mM ATP (Adenosine 5'-triphosphate) solution, and 1 µl of 400 unit/µl T4 DNA ligase (New England Biolabs) is added. The ligation mix is incubated at room temperature (RT) for 6 hours.

From the 10 µl of pMON17016/6G5 ligated DNA sample, 3 µl is packaged into lambda phage particles (Stratagene;

Gigapack Plus) using the manufacturer's procedure. To establish the cosmid titer, serial dilutions are made and used to infect the host bacteria. A culture of the host MM294 (Talmadge and Gilbert 1980) *E. coli* is grown at 30° C. in L-Broth containing 0.2% maltose. A 100 μl sample of MM294 is diluted with 100 μl SM buffer (SM=50 mM Tris pH7.5, 100 mM NaCl, 8 mM MgSO$_4$, 0.01% gelatin) and infected with 10 μl fractions of the packaged cosmid. The sample is incubated at RT for 15 minutes. One ml of L-Broth is added to the sample and incubated at 37° C. for 30 minutes. The infected bacteria are then concentrated by centrifugation (4000 rpm, 4 minutes.) and plated on L-Broth agar plates containing 100 μg/ml carbenicillin. The plates are incubated at 37° C. overnight. The cosmid titer typically observed is estimated at ~8.5×10$^5$ clones total from the 3 μl ligated pMON17016/6G5 DNA, or 2.8×10$^6$ clones per μg 6G5 EcoRI DNA.

To select the cosmid clones which contain the ACC deaminase gene, the 6G5 library is then plated on media containing ACC as a sole nitrogen source. The plates contain 1.5% nitrogen free agar, 2 mM MgSO$_4$, 0.2% glucose, 0.1 mM CaCl$_2$, 1× M9 salts (M9 salts=6 g Na$_2$HPO$_4$.7H$_2$O, 3 g KH$_2$PO$_4$, 1.5 g NaCl, per liter), 1 mM Thiamine-HCl, 100 μg/ml carbenicillin, and 3 mM ACC. The MM294 cells are infected with 35 μl (~5.6×10$^4$ clones) packaged cosmid as described above, washed two times with 1× M9 salts, and plated on five plates. Growth was evident after a 3 day incubation at 37° C. After a 6 day incubation, approximately 300 cosmids (1 per 200) grew on the minimal media plates containing ACC as a sole nitrogen source. There is no growth evident after 6 days on the control plate which did not contain ACC as a supplemental source of nitrogen.

Several colonies that grew on the minimal media containing ACC are then screened. All the samples in the instant description had different size cosmid inserts and most contained several common EcoRI fragments. The three smallest clones are screened by restriction deletions and subcloning of the common fragments. The activity of the ACC deaminase gene is monitored by plating the clones on minimal media containing ACC as described above. The screens identified a clone containing a ~10.6 Kb insert which retained activity. The insert is then subcloned on a BamHI-XbaI fragment into the pUC118 plasmid (Viera and Messing 1987). Subsequent HindIII and SinaI deletions narrowed down the ACC deaminase activity to the 2.4 Kb insert which allowed the clone to grow on minimal media with ACC as the sole nitrogen source. The pUC118 plasmid containing the 2.4 Kb insert is designated pMON10027.

Both strands of the 2.4 Kb insert of pMON10027 were then sequenced using the USB Sequenase® DNA sequencing kit following the manufacturer's directions. A 1017 base pair (bp) open reading frame was identified as the coding sequence of the ACC deaminase gene (FIG. 2). This sequence is identified as SEQ ID NO:1.

To further demonstrate the equivalence of the ACC deaminase genes from different organisms, the DNA sequence of a second gene was determined. The Pseudomonas 3F2 isolate was identified in the initial screen as an organism capable of growth on medium containing ACC as sole nitrogen source as previously described. Conversion of ACC to α-ketobutyric acid in vitro (as described for the 6G5 organism) demonstrated that this organism also contained an ACC deaminase enzyme. The polymerase chain reaction (PCR) was used to clone the 3F2 ACC deaminase. Oligodeoxynucleotides for priming off of 3F2 DNA based on the known 6G5 sequence were designed. The sequences of the 5' and 3' oligonucleotides are as follows:

5' oligonucleotide: CCCGGATCCATGAATCT-GAATCGTTTT (SEQ ID NO:11)

3' oligonucleotide: CCCGGATCCGCCGTTACGAAA-CAGGAA (SEQ ID NO:12)

These oligonucleotides begin with a sequence that incorporates a BamHI site into the PCR product to facilitate subsequent cloning. Each is identical to either the 6G5 sequence over the first 18 (5') or last 18 (3') nucleotides, which are underlined. The 3F2 DNA was prepared as previously described for 6G5. The PCR reaction was carded out under conditions that would permit annealing of the oligonucleotides to 3F2 DNA even if some mismatch between the 3F2 and 6G5 sequences existed. The PCR reaction was run for 30 cycles with 15 second extensions for each subsequent cycle. Each cycle consisted of:

| | |
|---|---|
| 94° C. | 1 minute |
| 40° C. | 2 minutes |
| 72° C. | 3 minutes plus 15 second extensions |

The PCR-amplified 3F2 DNA contains the first 18 (5') and last 18 (3') nucleotides of isolate 6G5's ACC deaminase nucleotide sequence incorporated into the oligonucleotides and thus may not correspond to the actual 3F2 gene in the areas of the first and last 18 nucleotides. Therefore, the actual identity of the first and last six amino acids of the 3F2 ACC deaminase may not be the same as the enzyme in the original 3F2 organism. Because a high degree of homology between the 3F2 DNA and the oligonucleotide primers is essential for successful DNA amplification, the 3F2 and 6G5 sequences must be quite similar.

The product of the PCR amplification was cloned into BamHI-cut pBSSK+ (Stratagene) and subjected to dideoxy DNA sequencing as previously described. The sequence of the gene was determined using a series of oligonucleotide primers derived from internal DNA sequences. The sequence of the 3F2 gene and the derived amino acid sequence of the ACC deaminase is shown in FIG. 17. The nucleotide sequence is identified as SEQ ID NO:15 and the amino acid sequence is identified as SEQ ID NO:16. A comparison of the derived amino acid sequences of the 6G5 and 3F2 enzymes indicates that they are highly homologous, having 96% identity and 99% similarity when conservative amino acid substitutions are considered. The sequence conservation, taken together with the kinetic data obtained on these two enzymes clearly indicates the conserved nature of the ACC deaminase in nature.

Once an ACC deaminase gene has been identified and isolated, it must be engineered for plant expression. To introduce the ACC deaminase gene into a plant, a suitable chimeric gene and transformation vector must be constructed. A typical chimeric gene for transformation into a plant will include a promoter region, a heterologous structural DNA coding sequence and a 3' non-translated polyadenylation site. A heterologous structural DNA coding sequence means a structural coding sequence that is not native to the plant being transformed or a structural coding sequence that has been engineered for improved characteristics of its protein product. Heterologous with respect to the promoter means that the coding sequence does not exist in nature in the same gene with the promoter to which it is now attached. Chimeric means a novel non-naturally occurring gene which is comprised of parts of different genes. In preparing the transformation vector, the various DNA fragments may be manipulated as necessary to create the desired vector. This includes using linkers or adaptors as necessary to form suitable restriction sites or to eliminate unwanted restriction sites or other like manipulations which are known to those of ordinary skill in the art.

Promoters which are known or found to cause transcription of the ACC deaminase gene in plant cells can be used in the present invention. Such promoters may be obtained from plants, plant pathogenic bacteria or plant viruses and include, but are not necessarily limited to, the 35S and 19S promoters of cauliflower mosaic virus (CaMV35S and CaMV19S), the full-length transcript promoter from the figwort mosaic virus (FMV35S) and promoters isolated from plant genes such as EPSP synthase, ssRUBISCO genes and promoters obtained from T-DNA genes of *Agrobacterium tumefaciens* such as nopaline and mannopine synthases. The particular promoter selected should be capable of causing sufficient expression to result in the production of an effective amount of ACC deaminase to substantially inhibit the production of ethylene. Those skilled in the art will recognize that the amount of ACC deaminase needed to inhibit ethylene production may vary with the type of plant and the tissues within the plant of interest.

Particularly useful promoters for use in the present invention are fruit specific promoters which are expressed during ethylene production in the fruit and the full-length transcript promoter from the figwort mosaic virus (FMV35S). The FMV35S promoter is particularly useful because of its ability to cause uniform and high levels of expression of ACC deaminase in plant tissues. The DNA sequence of a FMV35S promoter is presented in FIG. 22 and is identified as SEQ ID NO:17. Examples of fruit specific promoters include the E8, E4, E17 and J49 promoters from tomato (Lincoln, J. E., and Fischer, R. L. 1988), as well as the 2A11 promoter as described in U.S. Pat. No. 4,943,674.

The promoters used for expressing the ACC deaminase gene of this invention may be further modified if desired to alter their expression characteristics. For example, the CaMV35S promoter may be ligated to the portion of the ssRUBISCO gene which represses the expression of ssRUBISCO in the absence of light, to create a promoter which is active in leaves but not in roots. The resulting chimeric promoter may be used as described herein. As used herein, the phrase "CaMV35S" or "FMV35S" promoter includes variations of these promoters, e.g. promoters derived by means of ligation with operator regions, random or controlled mutagenesis, addition or duplication of enhancer sequences, etc.

The 3' non-translated region contains a polyadenylation signal which functions in plants to cause the addition of polyadenylated nucleotides to the 3' end of the RNA sequence. Examples of suitable 3' regions are the 3' transcribed, non-translated regions containing the polyadenylation signal of the tumor-inducing (Ti) plasmid genes of Agrobacterium, such as the nopaline synthase (NOS) gene, and plant genes like the 7s soybean storage protein genes and the pea E9 small subunit of the RuBP carboxylase gene (ssRUBISCO).

The RNA produced by a DNA construct of the present invention also preferably contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequences can be part of the 5' end of the non-translated region of the native coding sequence for the heterologous coding sequence, or part of the promoter sequence, or can be derived from an unrelated promoter or coding sequence as discussed above.

A DNA construct of the present invention can be inserted into the genome of a plant by any suitable method. Suitable plant transformation vectors include those derived from a Ti plasmid of *Agrobacterium tumefaciens*, such as those disclosed by Herrera-Estrella (1983), Bevan (1983), Klee (1985) and U.S. Pat. No. 4,940,838. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, particle gun technology, and transformation using viruses. Methods for the introduction of vectors into maize, or other monocot cells would include, but are not limited to, the injection method of Neuhaus et al. (1987), the injection method of de la Pena et al. (1987) or the microprojectile methods of Klein et al. (1987) and McCabe et al. (1988).

The construction of vectors capable of being inserted into a plant genome via *Agrobacterium tumefaciens* mediated delivery is known to those of ordinary skill in the art. Typical plant cloning vectors comprise selectable and scoreable marker genes, T-DNA borders, cloning sites, appropriate bacterial genes to facilitate identification of transconjugates, broad host-range replication and mobilization functions and other elements as desired.

If Agrobacterium mediated delivery is chosen, once the vector has been introduced into the disarmed Agrobacterium strain, the desired plant can then be transformed. Any known method of transformation that will work with the desired plant can be utilized.

Plants particularly suitable for use in this invention are tomato, banana, kiwi fruit, avocado, melon, mango, papaya, apple, peach, and other climacteric fruit plants. The present invention should also be suitable for use in the following non-climacteric species: strawberry, lettuce, cabbage, cauliflower, onions, broccoli, cotton, canola and oilseed rape. Other plant species that are affected by the ethylene induced ripening process may also benefit from the teachings of the present invention especially those in which ethylene production is critical to the growth of the plant or the ripening or development of the fruit of the plant. In the flower industry, particularly desirable flower species would be carnations, roses and the like. This list should be interpreted as only illustrative and not limiting in any sense.

In order to obtain constitutive expression of the ACC deaminase gene in plants, the gene was cloned into the transformation vector pMON977. The ACC deaminase gene isolated from the 6G5 isolate was used in the transformation vectors prepared herein. The pMON977 plasmid (FIG. 3) contains the following well characterized DNA segments. First, the 0.93 Kb fragment isolated from transposon Tn7 which encodes bacterial spectinomycin/streptomycin resistance (Spc/Str), and is a determinant for selection in *E. coli* and *Agrobacterium tumefaciens* (Fling et al. 1985). This is joined to the chimeric kanamycin resistance gene engineered for plant expression to allow selection of the transformed tissue. The chimeric gene consists of the 0.35 Kb cauliflower mosaic virus 35S promoter (P-35S) (Odell et al. 1985), the 0.83 Kb neomycin phosphotransferase type II gene (NPTII), and the 0.26 Kb 3'-nontranslated region of the nopaline synthase gene (NOS 3') (Fraley et al. 1983). The next segment is the 0.75 Kb origin of replication from the $RK_2$ plasmid (ori-V) (Stalker et al. 1981). This is joined to the 3.1 Kb SalI to PvuI fragment from pBR322 which provides the origin of replication for maintenance in E. coli (ori-322), and the bom site for the conjugational transfer into the Agrobacterium tumefaciens cells. Next is the 0.36 Kb PvuI to BclI fragment from the pTiT37 plasmid, which contains the nopaline-type T-DNA right border region (Fraley et al. 1985). The last segment is the expression cassette consisting of the 0.65 Kb cauliflower mosaic virus (CaMV) 35S promoter enhanced by duplication of the promoter sequence (P-E35S) (Kay et al. 1987), a synthetic multilinker with several unique cloning sites, and the 0.7 Kb 3' nontranslated region of the pea rbcS-E9 gene (E9 3') (Coruzzi et al. 1984 and Morelli et al. 1985).

Figure 4:
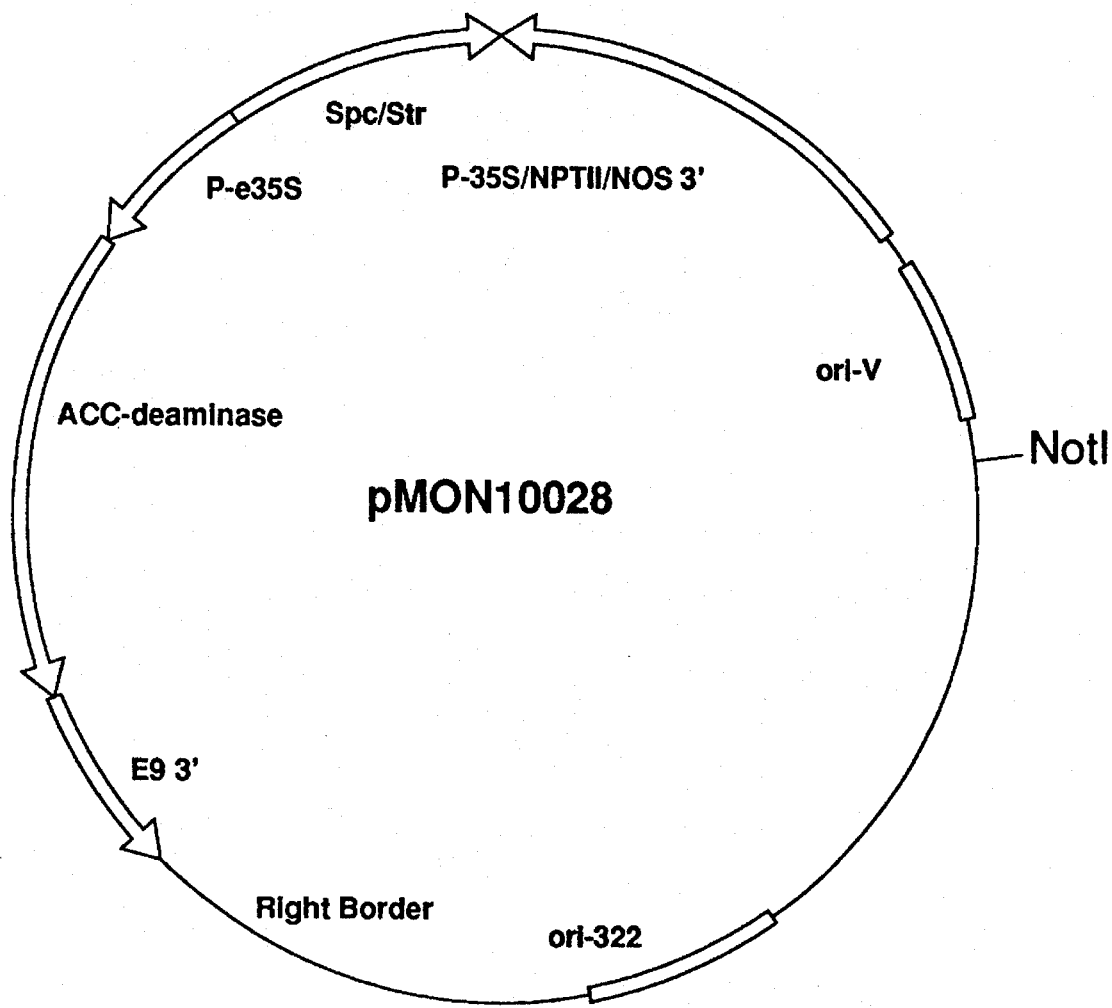
FIG. 4 illustrates a plasmid map of pMON10028.
Figure 5:
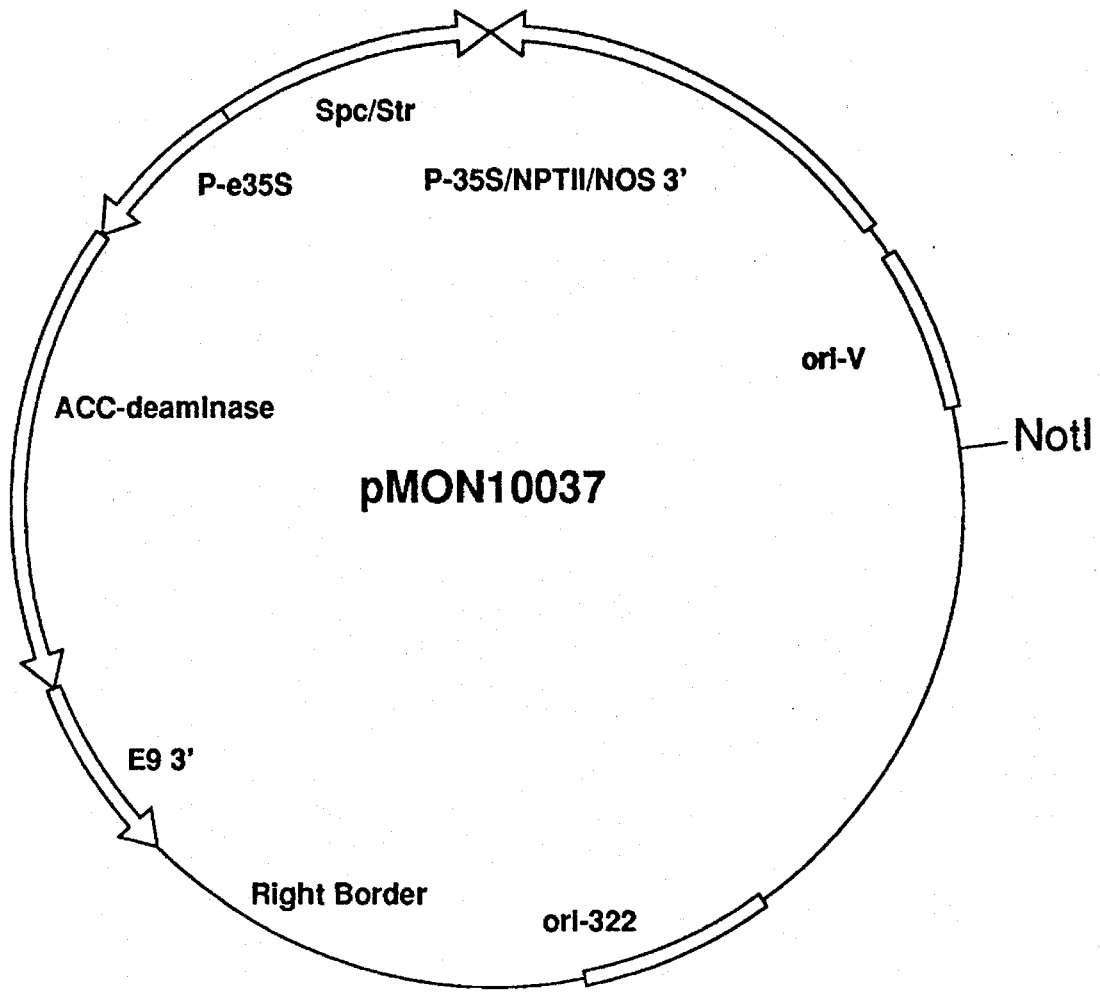
FIG. 5 illustrates a plasmid map of pMON10037.

Two different size fragments both containing the ACC deaminase gene from pMON10027 were introduced between the E35S promoter and the E9 3' end of pMON977. First, the 1071 bp EcoRV-SacI fragment from pMON10027 was introduced into the StuI-SacI cut pMON977, generating the pMON10028 vector (FIG. 4). Second, the 1145 bp EcoRV-EcoRV fragment from pMON10027 was introduced into the StuI cut pMON977, generating the pMON10037 vector (FIG. 5).

In order to construct vectors capable of directing expression of ACC deaminase specifically to fruit, a tomato fruit specific transcriptional promoter needed to be isolated. The promoter that was chosen is known to be induced to express at high levels in the presence of ethylene and is also known to be limited to the tomato fruit (Lincoln, J. and Fischer, R. 1988). The DNA sequence of the promoter for this gene, E8, has been published (Deikman et al. 1988). The DNA sequence of the E8 promoter is designated SEQ ID NO:10 and is illustrated in FIG. 14. While this promoter was chosen, other fruit specific promoters would also be useful and their identification and isolation routine to one of ordinary skill in the art. The promoter fragment E8 was isolated using standard polymerase chain reaction techniques. Oligonucleotides complementary to the E8 promoter were synthesized. The DNA sequences of the 5' and 3' oligonucleotides were as follows:

5' oligonucleotide: GAAGGAAGCT TCACGAAATC GGCCCTTATT C (SEQ ID NO:2)

3' oligonucleotide: GGGGCTTTAG ATCTTCTTTT GCACTGTGAA TG (SEQ ID NO:3).

The 5' oligonucleotide introduced a HindIII site approximately 1040 nucleotides 5' to the start of transcription. The 3' oligonucleotide introduces a BglII site approximately 20 nucleotides beyond the start of transcription. The PCR product is an approximately 1060 nucleotide fragment that can be cloned as a HindIII to BglII fragment. This promoter fragment will confer tissue-specific expression upon any coding sequence placed adjacent to it in an appropriate orientation.

The PCR reaction was performed essentially as recommended by the manufacturer of the GeneAmp kit (Perkin Elmer-Cetus). The reaction mix consisted of the following:

| water | 58.5 µl |
| 10X buffer | 10 µl |
| dNTP mix | 16 µl |
| 5' primer | 75 pM in 3.0 µl |
| 3' primer | 75 pM in 3.0 µl |
| tomato DNA | 1.24 µg in 2 µl |
| Ampltaq DNA polymerase | 0.5 µl |

The PCR reaction was run using the following temperature/time combination for 28 cycles:

| 94° C. | 1 minute |
| 60° C. | 2 minutes |
| 72° C. | 3 minutes. |

Figure 6:
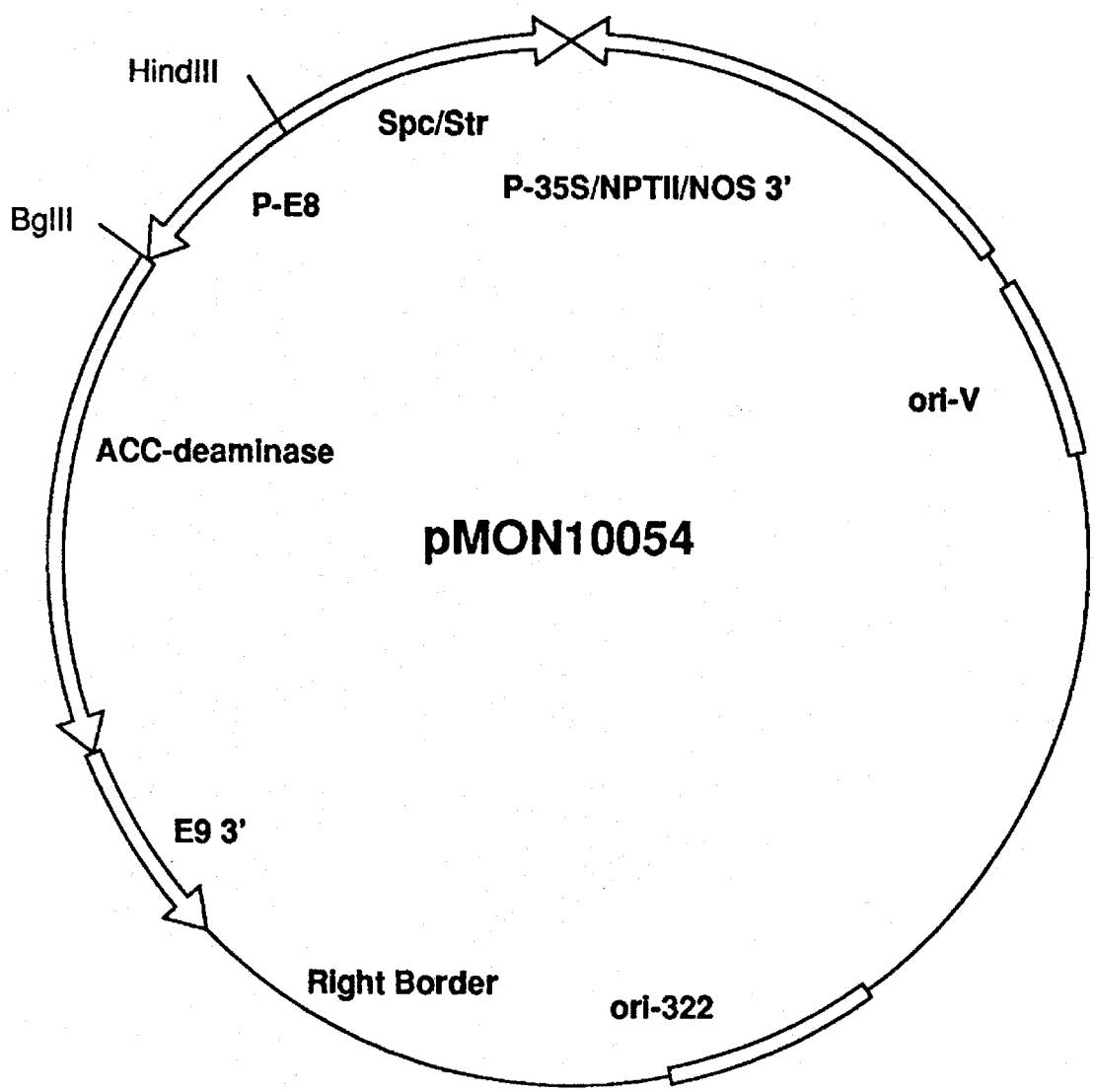
FIG. 6 illustrates a plasmid map of pMON10054.

Following completion, a PCR product of the correct size was observed. The fragment was purified by extraction with an equal volume of 1:1 phenol:chloroform followed by ethanol precipitation. The PCR fragment was then cut with HindIII and BglII so that it could be ligated to pMON10037 DNA. The PCR fragment was then ligated to pMON10037 DNA that had been cut with the same enzymes to remove the CaMV35S promoter sequence. The resulting plasmid contains the E8 promoter in the same location as the CaMV35S promoter of pMON10037 and was named pMON10054 (FIG. 6).

Both of the pMON10028 and pMON10037 vectors can be mobilized into the ABI Agrobacterium strain. The ABI strain is the A208 Agrobacterium tumefaciens carrying the disarmed pTiC58 plasmid pMP90RK (Koncz and Schell 1986). The Ti plasmid does not carry the T-DNA phytohormone genes, and the strain is therefore unable to cause the crown gall disease. Mating of pMON vectors into ABI is done by the triparental conjugation system using the helper plasmid pRK2013 (Ditta et al. 1980). When the plant tissue is incubated with the ABI::pMON conjugate, the vector is transferred to the plant cells by the vir functions encoded by the disarmed pMP90RK Ti plasmid. The vector opens at the T-DNA right border region, and the entire pMON vector sequence is inserted into the host plant chromosome. The Ti plasmid does not transfer to the plant cell but remains in the Agrobacterium.

The following examples further demonstrate several preferred embodiments of this invention. Those skilled in the art will recognize numerous equivalents to the specific embodiments described herein. Such equivalents are intended to be within the scope of the claims.

EXAMPLE 1

Transformed tobacco plants have been generated using the ABI::pMON10028 and the ABI::pMON10037 vectors, to demonstrate the expression of the ACC deaminase gene in plants.

Tobacco cells were transformed using the tobacco leaf disc method. The tobacco leaf disc transformation protocol employed healthy leaf tissue about 1 month old. After a 15–20 minute surface sterilization with 10% Clorox plus a surfactant, the tobacco leaves were rinsed 3 times in sterile water. Using a sterile paper punch, leaf discs were punched and placed upside down on MS104 media (MS salts 4.3 g/l, sucrose 30 g/l, B5 vitamins 500× 2 ml/l, NAA 0.1 mg/l, and BA 1.0 mg/l) for a 1 day preculture.

The discs were then inoculated with an overnight culture of disarmed Agrobacterium ABI containing the subject vector that had been diluted ⅕ (i.e. about 0.6 OD). The inoculation was done by placing the discs in centrifuge tubes with the culture. After 30 to 60 seconds, the liquid was drained off and the discs were blotted between sterile filter paper. The discs were then placed upside down on MS104 feeder plates with a filter disc to co-culture.

After 2–3 days of co-culture, the discs were transferred, still upside down, to selection plates with MS104 media. After 2–3 weeks, callus formed, and individual clumps were separated from the leaf discs. Shoots were cleanly cut from the callus when they were large enough to distinguish from stems. The shoots were placed on hormone-free rooting media (MSO: MS salts 4.3 g/l, sucrose 30 g/l, and B5 vitamins 500× 2 ml/l) with selection. Roots formed in 1–2 weeks. Any leaf callus assays were preferably done on rooted shoots while still sterile. Rooted shoots were placed in soil and were kept in a high humidity environment (i.e. plastic containers or bags). The shoots were hardened off by gradually exposing them to ambient humidity conditions.

In order to assay for ACC deaminase in the leaves, tobacco leaf samples were collected and frozen in liquid nitrogen. One gram of tissue was kept frozen under liquid nitrogen and ground to a fine powder. One ml of extraction buffer (100 mM Tris pH7.1, 10 mM EDTA, 35 mM KCl, 20% glycerol, 5 mM DTT, 5 mM L-ascorbate, 1 mM benzamidine, 1 mg/ml BSA) was added to the sample and ground for 45 seconds, then immediately centrifuged (12,000 g, 3 minutes) to remove the leaf debris. To remove small molecules, 250 µl of the extract was run over a 1 ml Sephadex G-50 spin column which was previously equilibrated with the above extraction buffer (less the BSA).

The extracts were assayed for the relative amount of the ACC deaminase enzyme activity in the transformed plant tissue. The ACC deaminase enzyme converts the ACC substrate into α-ketobutyrate and ammonia. The α-ketobutyrate was reacted with 2-4-dinitrophenyl-hydrazine hydrochloride to form a hydrazone derivative whose optical density was measured at 520 nm following addition of NaOH. The optical density values are a measure of the amount of ACC deaminase in the plant extract. The assay reaction mix contained a 50 µl sample of the tobacco leaf extract, 100 mM Tris pH8.6, and 50 mM ACC in a final volume of 150 µl. The reaction was incubated at 30° C. for 1 minute, and terminated with 50 µl of 0.56M HCl. A 0.6 ml aliquot of 0.1% 2,4-dinitrophenyl-hydrazine in 2N HCl was added. The sample was boiled for 2 minutes, cooled to room temperature, and 0.2 ml of 40% NaOH was added. A centrifugation (12,000 g, 5 minutes) removes the precipitate. The optical density of the supernatant was measured at 520 nm, which indicated the relative amount of the ACC deaminase enzyme being produced in the plants. Non-transformed tobacco plants were used as negative controls.

Several tobacco leaf extracts were assayed and the ACC deaminase activity was found to range from 0.6 to 7.5 mmoles product (α-ketobutyrate acid)/mg total protein/minute. These assay results demonstrated that the ACC deaminase was being expressed in the tobacco plant.

EXAMPLE 2

Transformed tomato plants have been generated using the ABI::pMON10028 and the ABI::pMON10037 vectors, and the expression of the ACC deaminase gene has been demonstrated in these plants.

Tomato plant cells were transformed utilizing the Agrobacterium strains described above generally by the method as described in McCormick et al. (1986). In particular, cotyledons were obtained from 7–8 day old seedlings. The seeds were surface sterilized for 20 minutes in 30% Clorox bleach and were germinated in Plantcons boxes on Davis germination media. Davis germination media is comprised of 4.3 g/l MS salts, 20 g/l sucrose and 10 mls/l Nitsch vitamins, pH5.8. The Nitsch vitamin solution is comprised of 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine. The seeds were allowed to germinate for 7–8 days in the growth chamber at 25° C., 40% humidity under cool white lights with an intensity of 80 einsteins $m^{-2}s^{-1}$. The photoperiod was 16 hours of light and 8 hours of dark.

Once germination occurred, the cotyledons were explanted using a #15 feather blade by cutting away the apical meristem and the hypocotyl to create a rectangular explant. These cuts at the short ends of the germinating cotyledon increased the surface area for infection. The explants were bathed in sterile Davis regeneration liquid to prevent desiccation. Davis regeneration media is composed of 1× MS salts, 3% sucrose, 1× Nitsch vitamins, 2.0 mg/l zeatin, pH 5.8. This solution was autoclaved with 0.8% Noble Agar.

The cotyledons were pre-cultured on "feeder plates" composed of media containing no antibiotics. The media is composed of 4.3 g/l MS salts, 30 g/l sucrose, 0.1 g/l myo-inositol, 0.2 g/l $KH_2PO_4$, 1.45 mls/l of a 0.9 mg/ml solution of thiamine HCl, 0.2 mls of a 0.5 mg/ml solution of kinetin and 0.1 ml of a 0.2 mg/ml solution of 2,4 D. This solution was adjusted to pH 6.0 with KOH. These plates were overlaid with 1.5–2.0 mls of tobacco suspension cells (TXD's) and a sterile Whitman filter which was soaked in 2COO5K media. 2COO5K media is composed of 4.3 g/l Gibco MS salt mixture, 1 ml B5 vitamins (1000× stock), 30 g/l sucrose, 2 mls/l PCPA from 2 mg/ml stock, and 10 µl/l kinetin from 0.5 mg/ml stock. The cotyledons were cultured for 1 day in a growth chamber at 25° C. under cool white lights with a light intensity of 40–50 einsteins $m^{-2}s^{-1}$ with a continuous light photoperiod.

Cotyledons were then inoculated with a log phase solution of Agrobacterium containing the desired transgenic gene. The concentration of the Agrobacterium was approximately $5 \times 10^8$ cells/ml. The cotyledons were allowed to soak in the bacterial solution for six minutes and were then blotted to remove excess solution on sterile Whatman filter disks and were subsequently replaced to the original feeder plate where they were allowed to co-culture for 2 days. After the two days, cotyledons were transferred to selection plates containing Davis regeneration media with 2 mg/l zeatin fiboside, 500 µg/ml carbenicillin, and 100 µg/ml kanamycin. After 2–3 weeks, cotyledons with callus and/or shoot formation were transferred to fresh Davis regeneration plates containing carbenicillin and kanamycin at the same levels. The experiment was scored for transformants at this time. The callus tissue was subcultured at regular 3 week intervals and any abnormal structures were trimmed so that the developing shoot buds would continue to regenerate. Shoots developed within 3–4 months.

Once shoots developed, they were excised cleanly from callus tissue and were planted on rooting selection plates. These plates contained 0.5× MSO containing 50 µg/ml kanamycin and 500 µg/ml carbenicillin. These shoots formed roots on the selection media within two weeks. If no roots appeared after 2 weeks, shoots were trimmed and replanted on the selection media. Shoot cultures were incubated in percivals at a temperature of 22° C. Shoots with roots were then potted when roots were about 2 cm in length. The plants were hardened off in a growth chamber at 21° C. with a photoperiod of 18 hours light and 6 hours dark for 2–3 weeks prior to transfer to a greenhouse. In the greenhouse, the plants were grown at a temperature of 26° C. during the day and 21° C. during the night. The photoperiod was 13 hours light and 11 hours dark and the plants were allowed to mature.

Green tomato fruit and leaf samples were collected and frozen in liquid nitrogen. The samples were extracted and assayed using the procedures described for tobacco. The tomato extraction buffer contained 100 mM Tris pH7.1, 1 mM EDTA, 10% glycerol, 5 mM DTT, 5 mM L-ascorbate, 1 mM benzamidine, 1 mg/ml BSA. The extracts were assayed and the ACC deaminase activity was found to range from 1.6 to 11.2 mmoles of product/mg total protein/minutes reaction for the leaf tissue, and from 3.0 to 25.1 mmoles of product/mg total protein/minutes reaction for the tomato fruit tissue. The results of these assays demonstrated that the ACC deaminase was being expressed constitutively in the tomato plant.

EXAMPLE 3

Tomato plants transformed with a chimeric gene encoding ACC deaminase have also been assayed to determine the effect of the expression of ACC deaminase on the ripening of fruit of the tomato plant.

Plasmids pMON10028 and pMON10037 were introduced into tomato (*Lycopersicon esculentum* cv. UC82B) as described in Example 2.

Plants containing the genes were initially identified by resistance to kanamycin. Kanamycin resistant plants were further analyzed by ACC deaminase enzyme assays (as described above) and by routine western blot analysis using antibody prepared against purified ACC deaminase protein. Plants that expressed the ACC deaminase protein were chosen for further analysis.

Tomato plants that were identified as expressing the ACC deaminase gene were examined for inhibition of fruit ripening. R1 progeny of the primary transformants from two lines, designated 5673 and 5854, as well as nontransformed UC82B plants were grown under identical conditions in a greenhouse. Progeny of the transgenic plants were screened for the presence of the NPTII gene, indicating inheritance of the T-DNA. All plants, including the UC82B controls, produced flowers and initiated fruit development simultaneously. Plants were then scored for the day at which fruit entered the breaker stage (the stage when the fruit begins to turn red), indicating initiation of ripening. Plants that had been scored as NPTII positive from both of the transgenic lines showed a significant delay in initiation of ripening. The delay in onset of ripening was approximately one week. Fruits from the transgenic plants as well as UC82B controls were then removed from the plants at the breaker stage. Fruits were stored individually in 200 ml beakers at room temperature and allowed to ripen. The fruits from transgenic plants exhibited delays of from two to six weeks in the time it took to reach a fully ripe state. Thus, tomato plants expressing the ACC deaminase gene exhibited delays in both the initiation of ripening and the time that it took to progress through the stages of ripening after the process had been initiated.

EXAMPLE 4

*Nicotiana tabacum* plants transformed with pMON10028 and pMON10077 as described above have also been assayed to determine the effect of the expression of ACC deaminase in the plant on the life of the tobacco flowers. Tobacco plants expressing the ACC deaminase gene were identified using the same enzyme assay as used for the tomato plants. Enzyme assays were performed on tobacco leaves and flowers. Plants expressing the gene were assayed for the length of time that flowers were retained. Flowers were tagged at the point of anthesis (flower opening) and the time it took to reach a senesced stage was measured. While flowers from control plants showed significant wilting two days after anthesis, flowers from the transgenic plants expressing ACC deaminase were delayed in wilting by a full day.

EXAMPLE 5

The present invention may also be used in combination with other methods known to delay ripening in fruits. One such combination involves use of the ACC deaminase gene in combination with an antisense gene that inhibits ethylene production. A plasmid containing ACC deaminase in combination with an antisense gene for the pTOM13 cDNA has been prepared for this purpose (Holdsworth et al. 1987). The gene designated pTOM13 has been previously shown to inhibit ethylene production when placed in an antisense orientation in plants (Hamilton et al. 1980). It has been postulated that this gene encodes an enzyme that converts ACC to ethylene (presumably the enzyme is ACC oxidase) and inhibition of the synthesis of this enzyme with an antisense RNA leads to accumulation of ACC in plant tissue. A cDNA clone corresponding to the pTOM13 gene was isolated from a cDNA library prepared from ripening tomato fruit on the basis of its ability to hybridize to synthetic oligonucleotides prepared from the published pTOM13 sequence.

A cDNA library was purchased from Stratagene (Cat. #936004). This library was prepared from RNA isolated from ripening tomato fruit in the bacteriophage lambda cloning vector lambda-ZAP II. Oligonucleotide probes were prepared from segments of the pTOM13 published sequence as follows:

Oligonucleotide 1: 5' GGTGAACCAT GGAATTCCAC ATG 3' (SEQ ID NO:4)

Oligonucleotide 2: 5' GCAATTGGAT CCCTTTCCAT AGC 3' (SEQ ID NO:5)

Twenty thousand phage were plated on agar-containing plates as recommended by the manufacturer. The *E. coli* strain XL1-Blue, supplied by the manufacturer, was used for phage preparation. Phage plaques were transferred to nitrocellulose filters and baked in an 80° C. oven for 2 hours. Plates were prehybridized at 65° C. for 2 hours in the following solution:

6× SSC, 5× Denhardt's solution, 100 µg/ml denatured salmon sperm DNA, 20 mm Tris:HCl, pH 7.0, 0.1% SDS, 1.0 mM EDTA.

50× Denhardt's Solution=1.0% each of Ficoll, polyvinylpyrrolidone, bovine serum albumin (Fraction V; Sigma) in water.

20× SSC=175 g sodium chloride and 88.2 g sodium citrate per liter of water. pH adjusted to 7.0 with NaOH.

After prehybridization, $^{32}$P-labelled oligonucleotides (Sambrook et al. 1989) were added to a final concentration of 500,000 cpm/ml hybridization solution for each oligonucleotide. Hybridization was performed at 50° C. for 48 hours. Filters were washed twice in 6× SSC at room temperature for 15 minutes and once at 50° C. for 15 minutes. They were then dried and exposed to X-ray film for 48 hours. Plaques corresponding to hybridizing phage were isolated and purified by repeating the above procedure at a density of phage where single plaques could easily be separated from adjacent, non-hybridizing plaques. The pTOM13 cDNA insert was rescued in the plasmid vector pBS SK- as described by the manufacturer (Stratagene). This plasmid was designated pMON11023.

Figure 7:
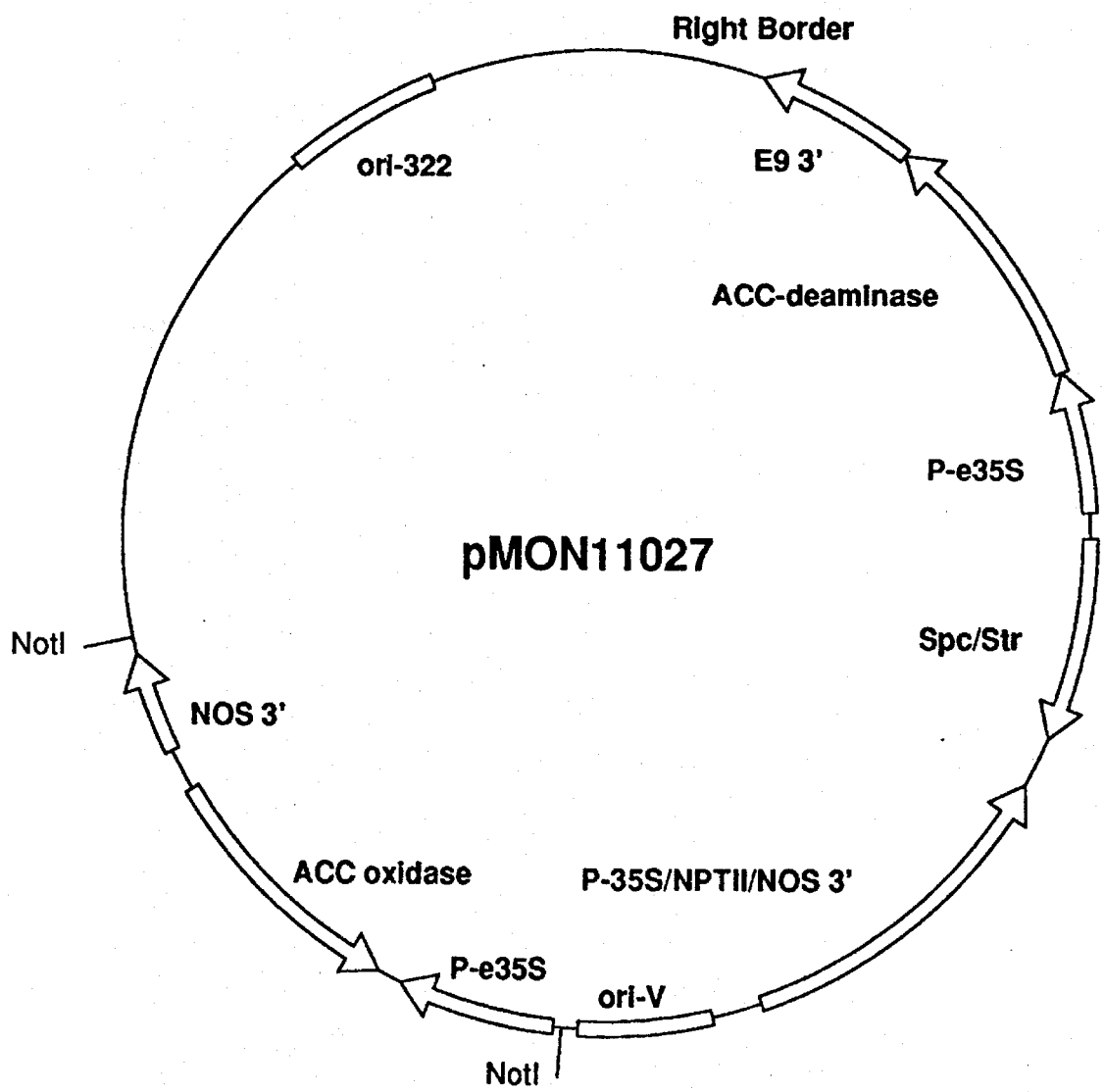
FIG. 7 illustrates a plasmid map of pMON11027.

A vector designed for expression of the pTOM13 cDNA insert in an antisense orientation was then prepared. The cDNA insert with adjacent polylinker was excised from pMON11023 by cutting with the restriction endonucleases BamHI and ClaI. The cDNA-containing portion of the plasmid was then cloned into pMON999 which had been cut with BglII and ClaI and treated with calf intestinal alkaline phosphatase. The resulting plasmid, pMON11025, contains the cDNA insert in an antisense orientation with respect to the CaMV35S promoter and a nopaline synthase 3' transcriptional terminator/polyadenylation site. This gene cassette can be excised as a single 2.2 kb NotI fragment. This NotI fragment was excised from pMON11025 and placed into the unique NotI site of pMON10028 to create pMON11027 (FIG. 7). This plasmid thus contains an antisense pTOM13 gene and a CaMV35S/ACC deaminase gene. This plasmid was introduced into Agrobacterium ABI using triparental mating as described above and used to transform tomato plants.

The resulting transformed plants should significantly inhibit the production of ethylene in the plant. It is expected that the action of the ACC deaminase gene in combination with the pTOM13 antisense gene will virtually eliminate ethylene synthesis and should further delay ripening of the fruit. It is expected that the combination of the ACC deaminase and the pTOM13 antisense gene will exhibit synergistic properties in the reduction of the formation of ethylene in the fruit or plant.

EXAMPLE 6

An alternate approach to reducing the rate of ethylene production in plant tissue involves overexpression of the gene encoding S-adenosylmethionine (SAM) decarboxylase. This enzyme degrades SAM which is the immediate precursor of ACC. The decarboxylated SAM is then converted to spermidine, a common polyamine. Since polyamines have themselves been reported to have antisenescence properties in plants, it is anticipated that SAM decarboxylase may prevent ripening in two ways 1) the production of spermidine and 2) degradation of a precursor to ethylene.

The gene encoding SAM decarboxylase (SEQ ID NO:9), illustrated in FIG. 15, has been cloned and its DNA sequence has been reported (Tabor and Tabor). The gene was cloned using PCR as described above in the protocol for isolation of the E8 promoter. *E. coli* DNA was purified as described above for the isolation of Pseudomonas 6G5 genomic DNA. Purified DNA was subjected to PCR as described above using the following oligonucleotides as primers:

5' oligonucleotide: GGAGAAGATA AGATCTATGA AAAAACTGAA ACTGC (SEQ ID NO:6)

3' oligonucleotide: GCAGAAGTAA ATAGATCTGG CGGAGCC (SEQ ID NO:7).

Figure 8:
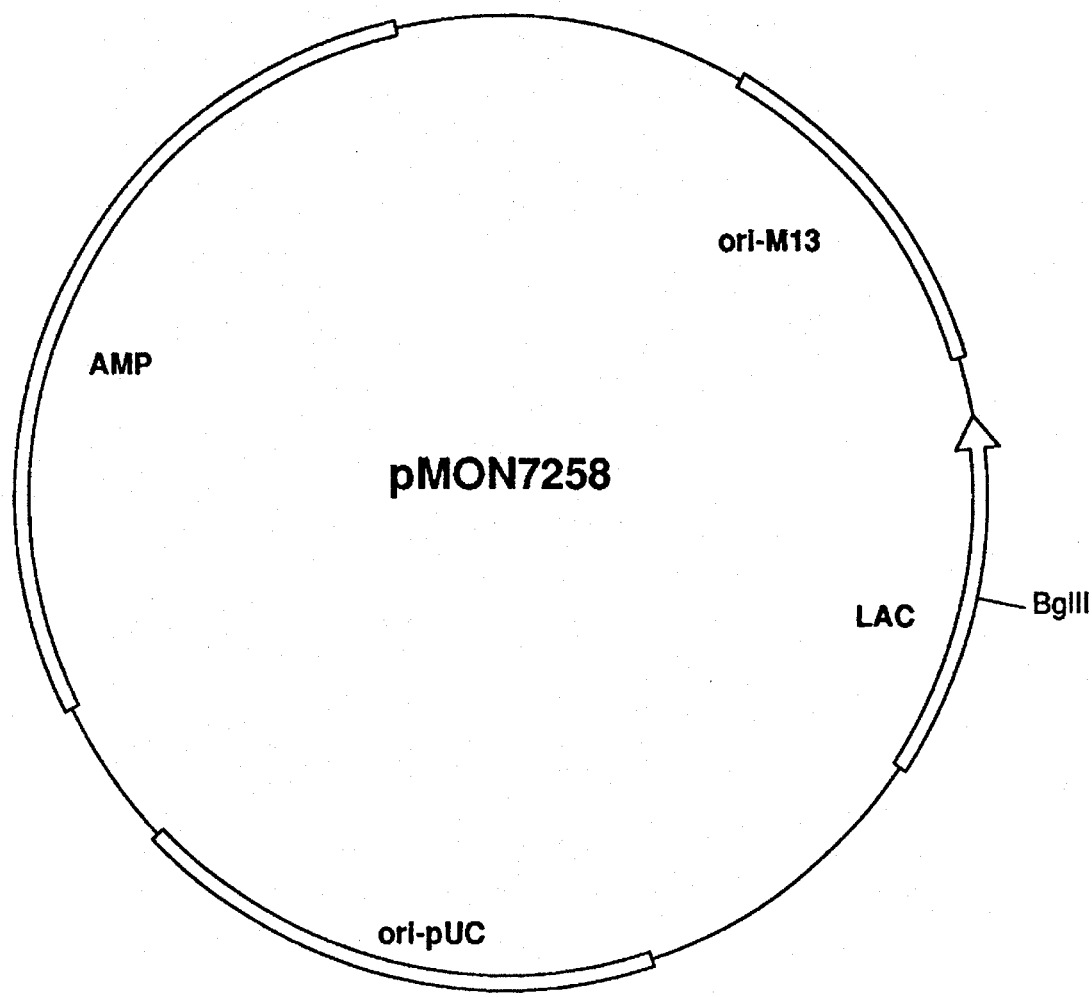
FIG. 8 illustrates a plasmid map of pMON7258.
Figure 9:
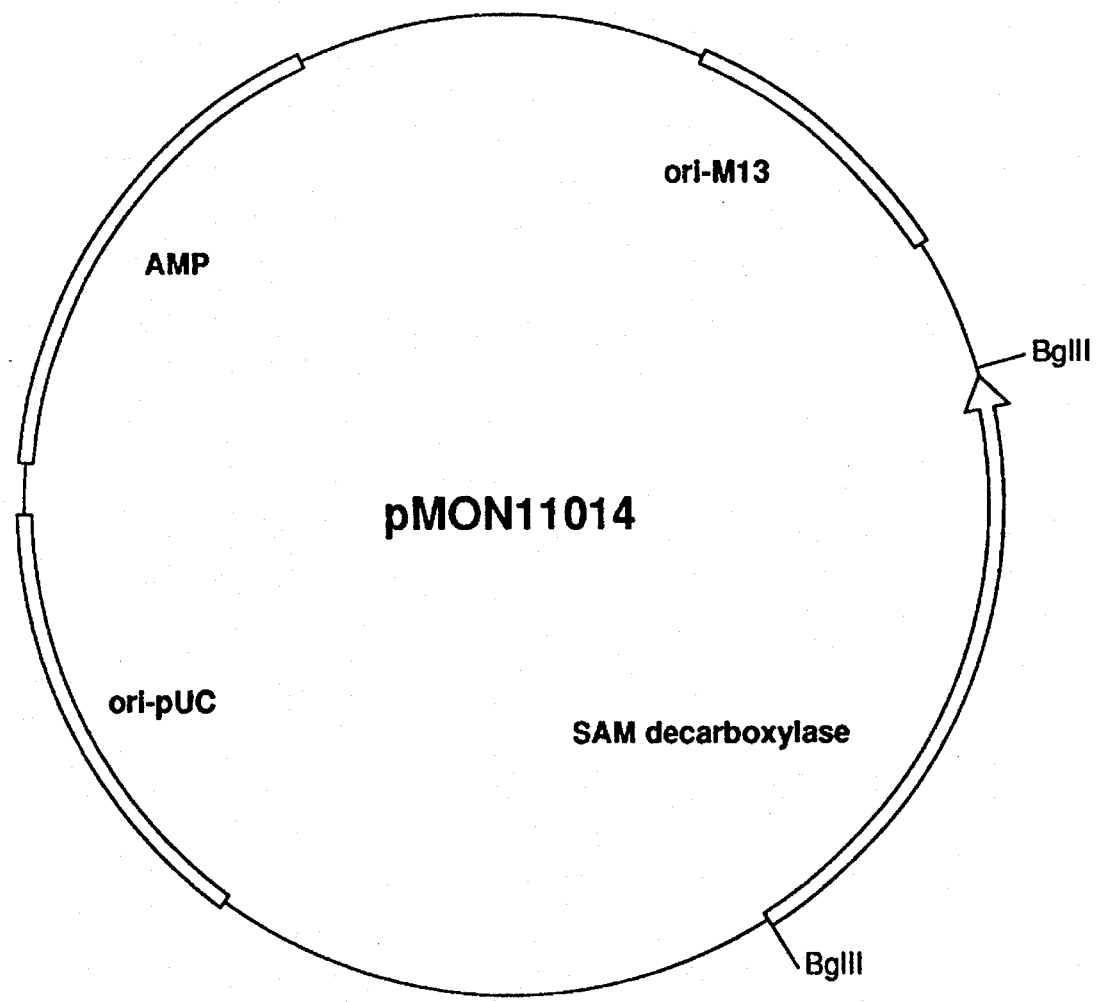
FIG. 9 illustrates a plasmid map of pMON11014.
Figure 10:
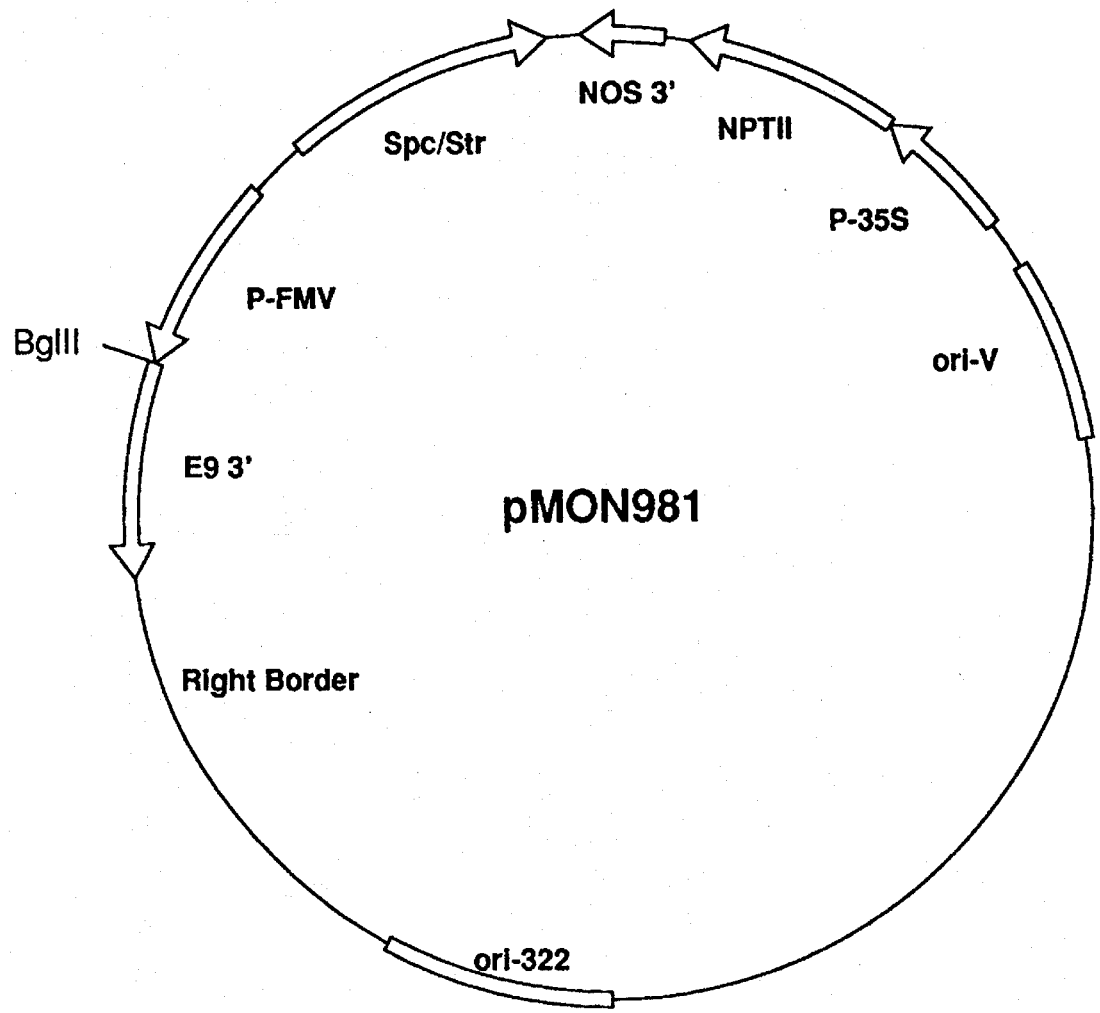
FIG. 10 illustrates a plasmid map of pMON981.
Figure 11:
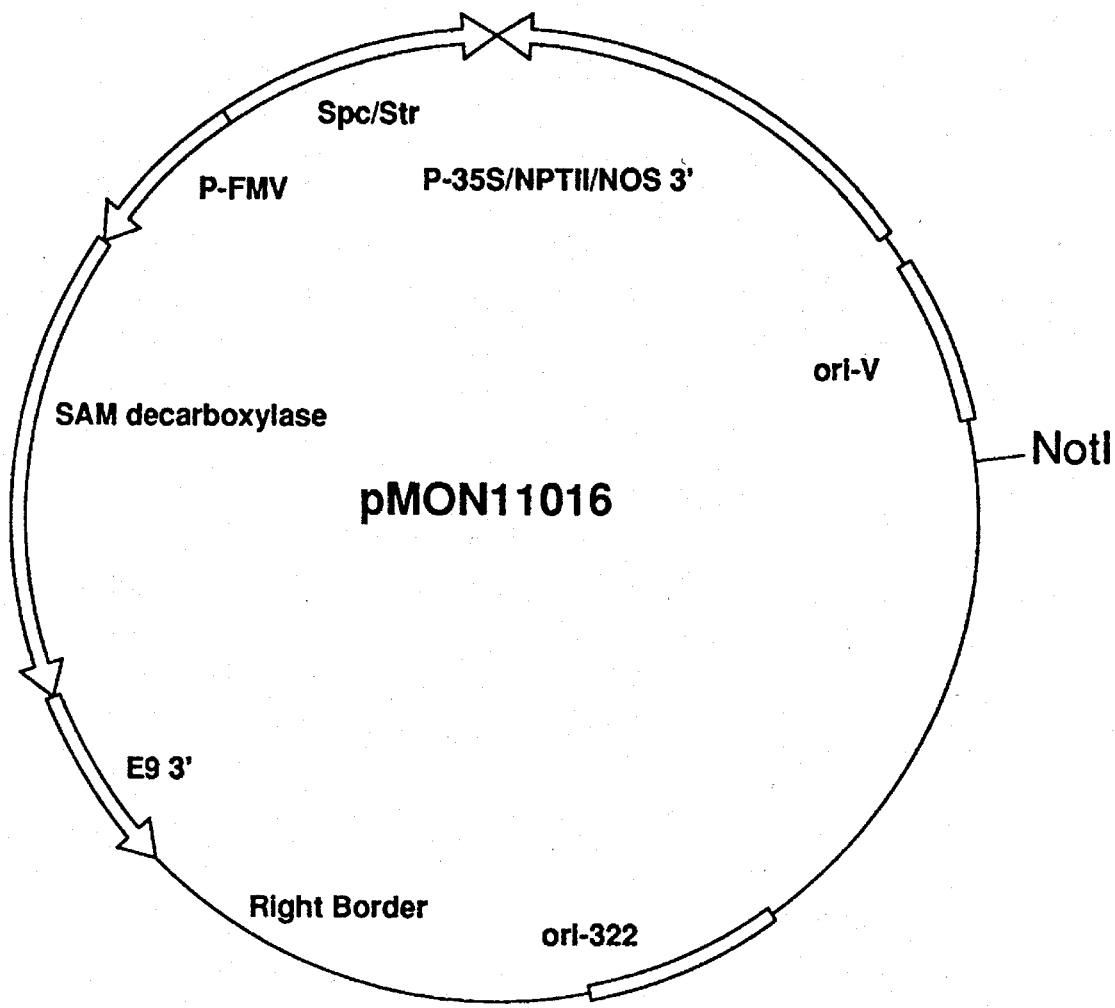
FIG. 11 illustrates a plasmid map of pMON11016.
Figure 12:
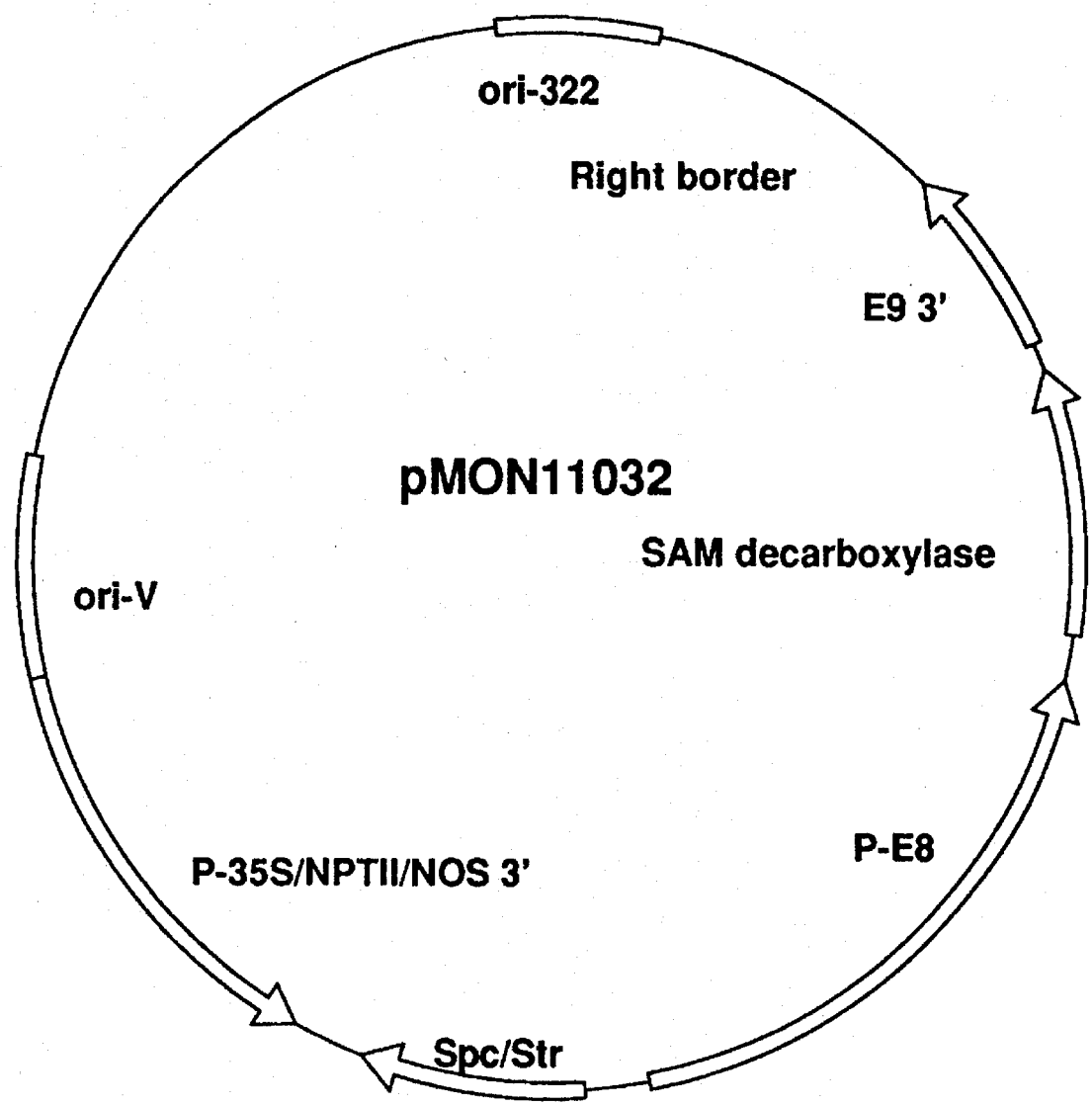
FIG. 12 illustrates a plasmid map of pMON11032.
Figure 13:
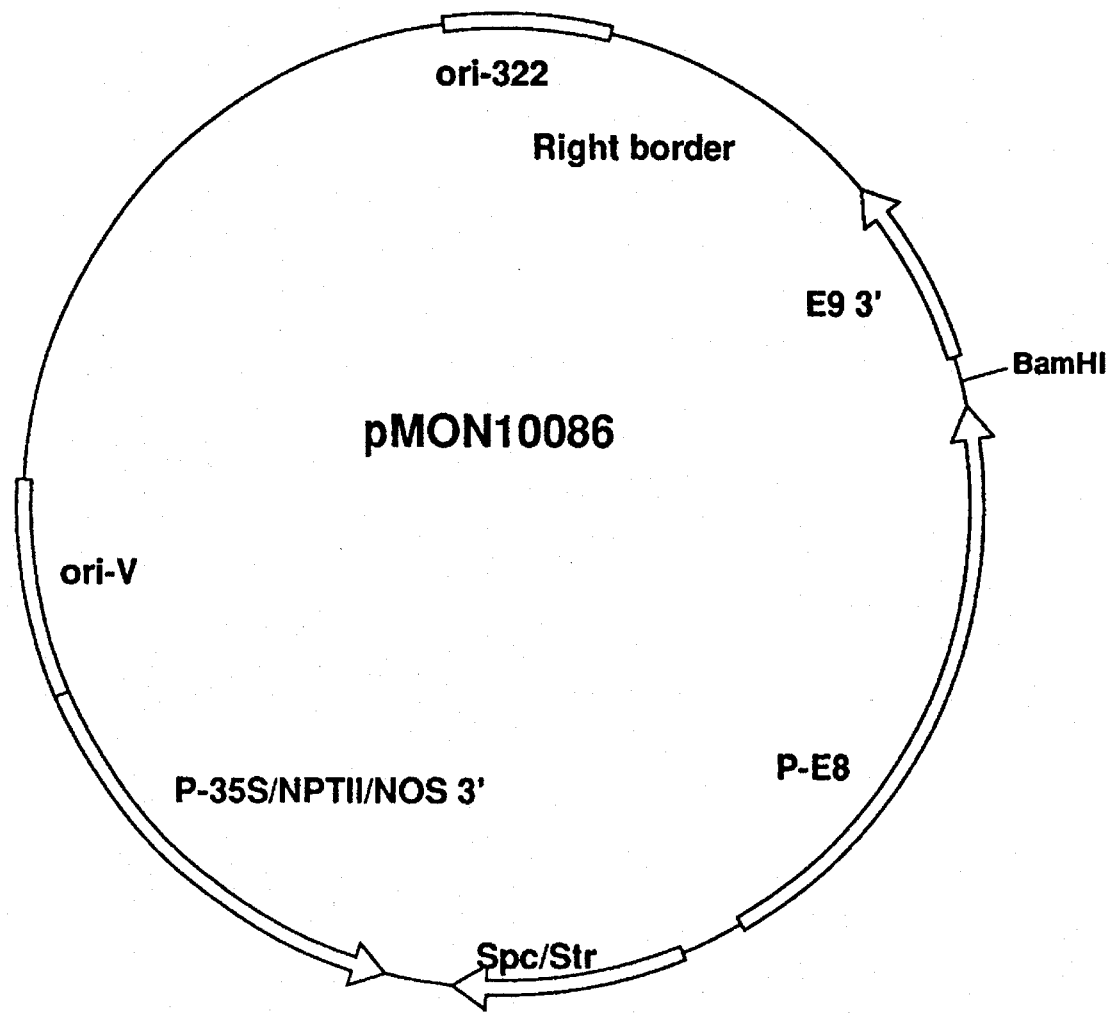
FIG. 13 illustrates a plasmid map of pMON10086.

The two primers used each introduced a BglII restriction site into the amplified DNA sequence to facilitate subsequent cloning steps. Following amplification, the DNA was cut with BglII and ligated with BglII cut pMON7258 (FIG. 8). The resultant plasmid, pMON11014 (FIG. 9), contained the SAM decarboxylase gene. The gene was subsequently cloned into plant transformation vectors that would permit expression of the gene under the control of either a constitutive promoter such as the full length transcript promoter from FMV or a fruit specific promoter such as the E8 promoter discussed above. The constitutive expression vector was constructed by cloning the pMON11014 BglII fragment containing SAM decarboxylase into BglII cut pMON981 (FIG. 10). The resulting plasmid, pMON11016 (FIG. 11), contained the gene in the correct orientation for expression in plants. The tissue specific expression vector, pMON11032 (FIG. 12), was constructed by insertion of the same BglII fragment from pMON11014 into BamHI cut pMON10086 (FIG. 13). Both transformation vectors were then introduced into Agrobacterium ABI using triparental mating. The Agrobacterium strains containing either pMON11016 or pMON11032 were then used to transform tomato plants as described above.

It is expected that plants expressing the ACC deaminase gene in combination with the SAM decarboxylase gene will inhibit synthesis of ethylene in plants, in a synergistic manner, such that the ripening or senescence process in the resulting plant is controlled to enhance the shelf life of the goods derived from the plant.

EXAMPLE 7

An ACC metabolizing enzyme such as ACC deaminase may also be used in combination with an antisense ACC synthase gene. The DNA sequence for ACC synthase is known (Van Der Straeten et al. 1990) (SEQ ID NO:8) and is presented in FIG. 16. Through routine manipulations, one can isolate a cDNA of the ACC synthase gene from a suitable cDNA library and prepare a vector containing the ACC synthase gene in an antisense orientation. This vector would contain the ACC synthase gene in an antisense direction and an ACC metabolizing enzyme such as ACC deaminase in addition with the other DNA fragments necessary for successful plant transformation. Preferably, both the antisense ACC synthase and the ACC deaminase are under the transcriptional control of a fruit specific promoter, such as E8.

The resulting transformed plants should significantly inhibit the production of ethylene in the fruit of the plant transformed. It is expected that the action of the ACC metabolizing enzyme in combination with the ACC synthase antisense gene will virtually eliminate ethylene synthesis and further delay ripening of the fruit. The fruit may be ripened at a desired time by exposure of the fruit to ambient ethylene.

EXAMPLE 8

This experiment was performed to evaluate the effect of reduction in ethylene levels in a plant when an ACC deaminase is expressed at high levels in the plant. Plant lines 5673 and 5854, as described in Example 3, were examined for ethylene generation in the plants and for phenotypic effects of expression of the ACC deaminase gene in the plant. Ethylene generation assays were performed on young leaf tissue from the plants by enclosing whole leaves or fruit in sealed containers and withdrawing 1.0 ml gas samples after one hour. Ethylene was quantified on a gas chromatograph (Ward et al. 1978) equipped with an alumina column and flame ionization detector. The results of ethylene generation assays are shown in Table 3 below.

TABLE 3

| | Ethylene Synthesis (nl/g/h) | |
|---|---|---|
| Plant | Leaf | Fruit |
| UC82B | 5.15 ± 0.69 | 11.73 ± 0.86 |
| UB82B-2 | 5.53 ± 0.37 | ND |
| 5673 | 0.60 ± 0.09 | 1.43 ± 0.36 |
| 5673-2 | 0.18 ± .02 | ND |
| 5854 | 1.14 ± 0.21 | ND |

(ND = not determined)

The ethylene level in plant line 5673 was reduced by 90% in one experiment utilizing young leaf tissue and by 97% in a second experiment. Plant line 5854 showed a reduction of approximately 78%. These data are consistent with the gene expression data in these plant lines. Line 5673 contained approximately 0.5% of the soluble protein as ACC deaminase while plant line 5854 contained approximately 0.05% of the soluble protein as ACC deaminase, as measured by protein gel blot analysis.

Protein gel blotting was performed by boiling protein samples for three minutes in the gel-loading buffer (50 mm TrisCl, pH 7, 100 mm dithiothreitol, 2% SDS, 10% glycerol, 0.1% bromophenol blue) and run on a 4–20% polyacrylamide MINI-PROTEAN II ready gels (BIO-RAD). The protein was transferred to nitrocellulose membrane using a MilliBlot-SDE electroblotting apparatus (Millipore, Bedford, Mass.) following the manufacturers directions. The membrane was incubated overnight at 4° C. in 1% BSA, TBST (10 mM Tris, pH 8, 150 mM NaCl, 0.05% Tween-20). The incubations were performed at room temperature with gentle agitation to hybridize the membrane. The primary ACC deaminase antibody was bound by incubating the membrane in a 1:1000 dilution of the goat serum in TBST for one hour. This was followed by three 10 minute washes in TBST. The secondary reagent was bound by incubating the membrane with 5 μC of $^{125}$I-labelled protein G in 20 ml of TBST for 30 minutes. The membrane was washed four times for 10 minutes with 0.1% Triton X-100 and exposed to film. Antibodies were obtained to the ACC deaminase protein by injecting a goat with 1.5 mg of protein and isolating antibodies from the goat pursuant to standard techniques known to those skilled in the art.

Figure 18:
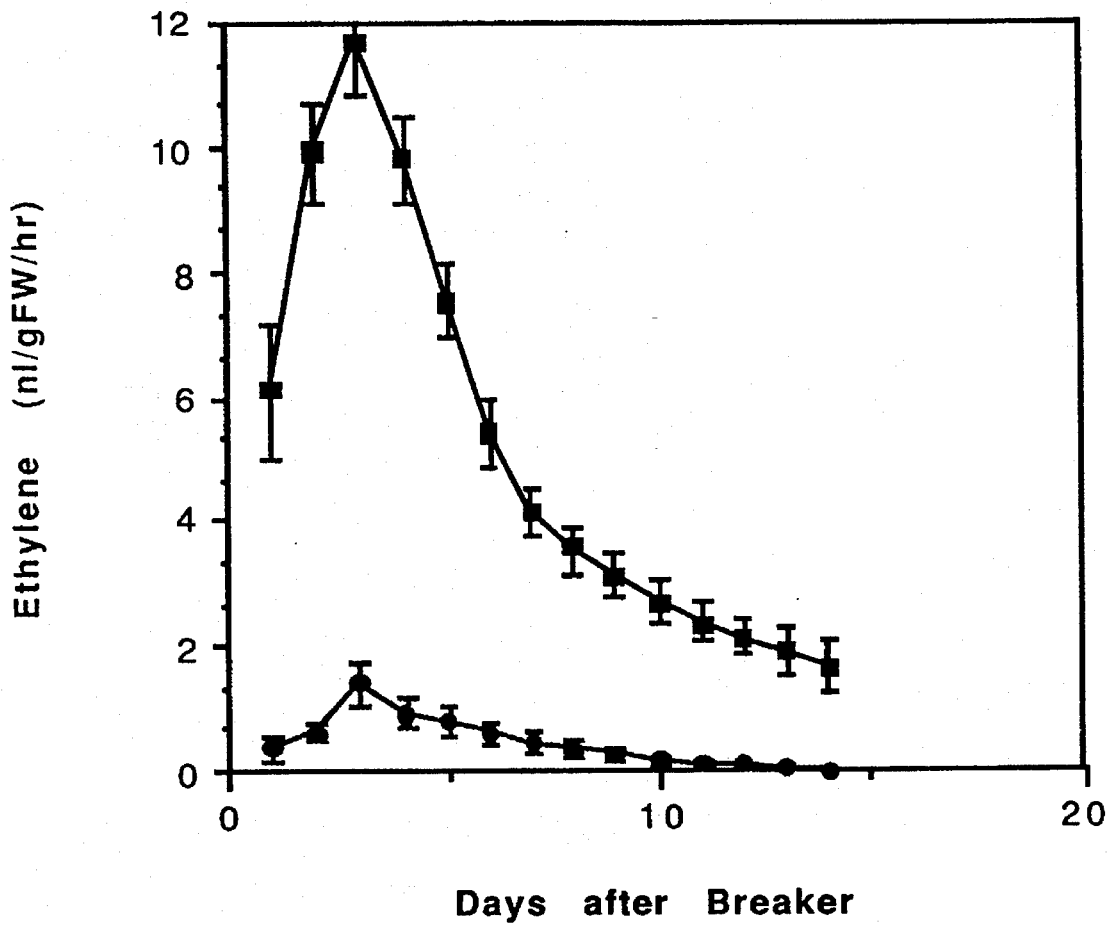
FIG. 18 illustrates graphically the relationship between the level of ethylene in control tomato fruit and transgenic tomato fruit expressing ACC deaminase.

Homozygous plants from plant line 5673 were also examined for phenotypic effects. Seed from the transgenic plants germinated normally, and plants were phenotypically indistinguishable from controls. The plants exhibited no delay in the onset of flowering or ripening. They did, however, show significant differences in the progression of ripening. The fruits of transgenic plants exhibited a peak of ethylene synthesis concomitant with control fruit, but at a level of only 10% that of controls. This is illustrated in FIG. 18. Ethylene generation by transgenic plants is represented by -●- and ethylene generation by control plants (UC82B) is represented by -■-. The bars represent means±standard error at specific time points. The fruit was detached at the breaker stage and ethylene generation measured daily as previously described. The delay in ripening of fruits detached at the breaker stage was also significant. Control fruit passed from breaker to fully red in seven days and exhibited a marked degree of softening after only two weeks. Transgenic tomato fruit reached the fully red stage after 24 days and remained firm for an extended period from the breaker stage. Fruit from transgenic plants remained firm for longer than 40 days and did not abscise while the control fruit had abscised after 14 days. These data are presented in Table 4.

TABLE 4

| | Ripening Stage | | | |
|---|---|---|---|---|
| Plant | 3 | 4 | 5 | 6 |
| Transgenic | 2.8 ± 0.53 | 5.3 ± 0.98 | 11.3 ± 3.1 | 23.5 ± 3.8 |
| Control | 1.4 ± 0.19 | 2.8 ± 0.26 | 5.1 ± 0.45 | 7.0 ± 0.53 |

The data in Table 4 are expressed as the number of days to reach a particular ripening stage after being detached, with a standard error. Ripening stages were defined as follows: Breaker, first sign of color change: 3, fully orange; 4, orange to red; 4, greater than 50% red; 6, fully red.

EXAMPLE 9

This example illustrates the expression of the ACC deaminase protein in a flowering plant species. The ACC deaminase gene was transformed into petunia plants. The petunia plants were transformed with a transformation vector that allows for the direct selection of transformed plants on glyphosate. Petunia explants were generally prepared for pre-culture as described for the tobacco plants in Example 1. Leaves from a one month old petunia plant were surface sterilized for fifteen minutes in a solution of 10% Clorox plus surfactant and washed three times with distilled water. The explants were cut in 0.5 cm squares, removing the leaf edges, mid-rib, tip, and petiole end for uniform tissue type. The explants were then placed in a single layer, upside down, on MS104 plates containing 2 mL 4COO5K media to moisten the surface and pre-cultured for 1–2 days. Explants were inoculated using an overnight culture of Agrobacterium containing the plant transformation vector that has been adjusted to a titer of $1.2 \times 10^9$ bacteria/mL with 4COO5K media. Explants were placed into a centrifuge tube, the Agrobacterium suspension was added and the mixture of bacteria and explants was "vortexed" on maximum setting for 25 seconds to insure even penetration of bacteria. The bacteria were poured off and the explants were blotted between layers of dry sterile filter paper to remove excess bacteria. The blotted explants were placed upside down on MS104 plates to which 2 mL 4COO5K media and a filter disk have been placed on top of the agar and co-cultured for two to three days. The explants were transferred to MS104 plates containing carbenicillin 1000 mg/l and cefotaxime at 100 mg/l for 3 days. The explants were then transferred to a new MS104 media that contains glyphosate at 0.05 mM, carbenicillin at 1000 mg/l and cefotaxime at 100 mg/l for the selection phase. At 4–6 weeks, shoots were cut from callus and placed on MSO and carbenicillin at 500 mg/l rooting media. Roots formed in 3–5 days, at which time leaf pieces were taken from rooted plates to confirm glysophate tolerance and that the material was transformed.

Figure 19:
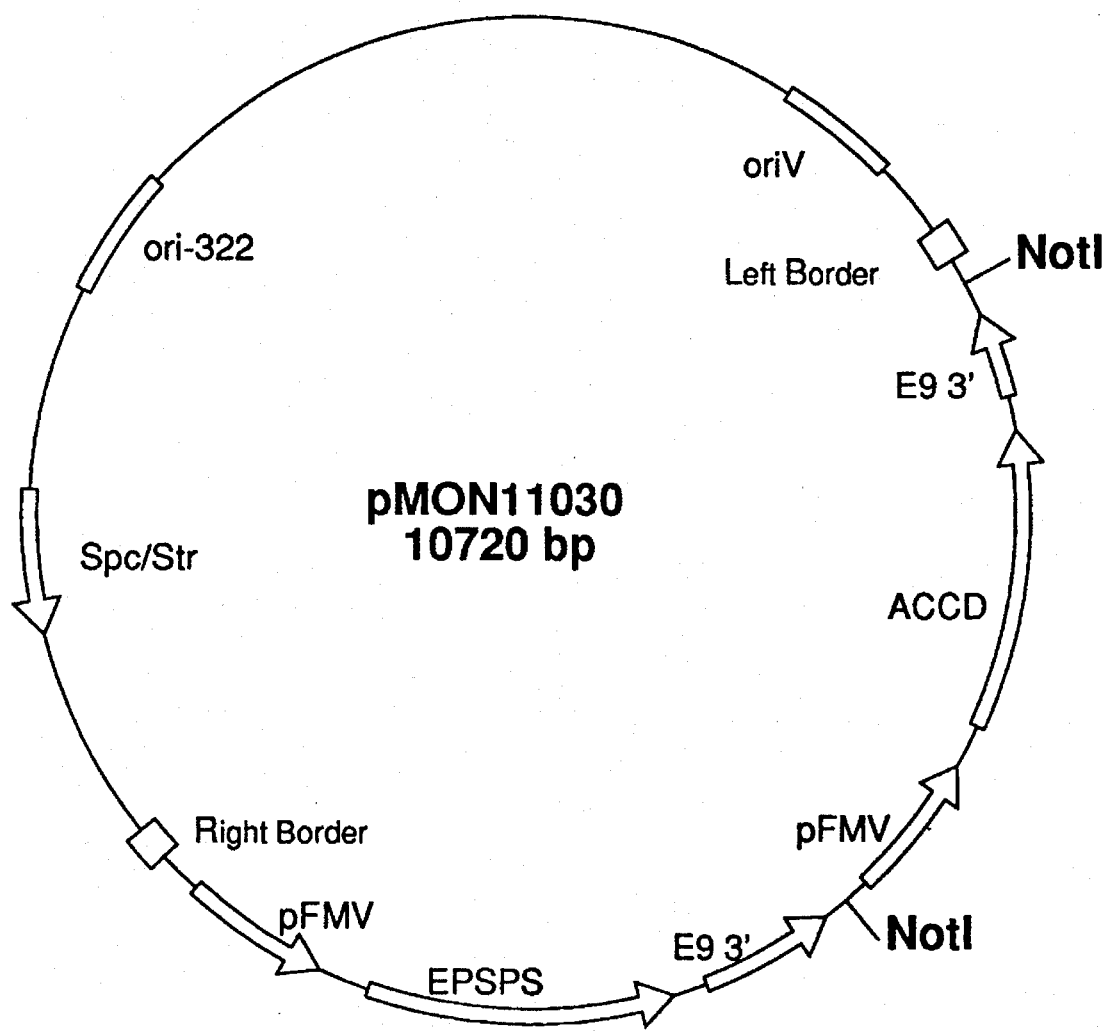
FIG. 19 illustrates a plasmid map of pMON11030.

The petunia plants were transformed with plant transformation vector pMON11030. A map of pMON11030 is presented in FIG. 19. This plasmid is essentially composed of the previously described bacterial replicon system that enables this plasmid to replicate in *E. coli* and to be introduced into and to replicate in Agrobacterium. Referring to FIG. 19, this plasmid additionally contains the bacterial spectinomycin-/streptomycin selectable marker gene (Spc/Str), and located between the T-DNA right border and left border is the CTP2-CP4 synthetic 5-enolpyruvyl-3-shikimate phosphate synthase (EPSPS) gene in the FMV35S promoter-E9 3' cassette. The CTP2-CP4 synthetic gene permits for selection of transformed cells by their ability to grow in the presence of glyphosate. The CTP2 is a chloroplast transit peptide and its DNA sequence is presented in FIG. 20 (SEQ ID NO:13). The DNA sequence of the CP4 EPSPS, a gene capable of conferring resistance to glyphosate, is presented in FIG. 21 (SEQ ID NO:14). The ACC deaminase gene from isolate 6G5 was placed between the FMV promoter and a nopaline synthase 3' region as a 2.0 kb NotI fragment into the unique NotI site to create pMON11037.

The presence of the ACC deaminase protein in transformed petunia tissues has been confirmed by immunoblot analysis of leaf discs as described in Example 8. ACC deaminase protein has been detected in leaf tissues in five out of six regenerated petunia plants.

Ethylene levels of transgenic petunia plants transformed with pMON11030 have also been determined in petunia plants expressing ACC deaminase. The level of ethylene in the plant is reduced to about one-half of the ethylene level in a control plant that has not been transformed. The results of ethylene generation assays are presented in Table 5 below.

TABLE 5

| Plant Line | ETHYLENE SYNTHESIS (nl/g/h) Leaf Tissue |
|---|---|
| 35861 | 0.58 |
| 35860 | 0.53 |
| 35862 | 0.62 |
| Control | 1.09 |

These data illustrate that transgenic plants expressing the ACC deaminase protein have reduced ethylene levels in leaf tissues. It is expected that such plants will show reduced senescence of flowers and leaves when compared to non-transformed plants.

All publications and patents mentioned in this specification are herein incorporated by reference as if each individual publication or patent was specifically and individually stated to be incorporated by reference.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

BIBLIOGRAPHY

Birnboim, H. C. and Doly, J. (1979) A rapid alkaline extraction procedure for screening recombinant plasmid DNA. Nucl. Acids. Res. 7:1513–1525.

Coruzzi, G., Broglie, R., Edwards, C., and Chua, N. H. (1984). Tissue-specific and light-regulated expression of a pea nuclear gene encoding the small subunit of ribulose-1,5-bisphosphate carboxylase. EMBO J 3, 1671–1679.

Deikman, J. and Fischer, R. (1988). Interaction of a DNA binding factor with the 5'-flanking region of an ethylene-responsive fruit ripening gene from tomato. EMBO J. 7, 3315–3320.

de la Pena, A., Lorz, H. and Schell, J. (1987) Nature 325:274–276.

Ditta, G., Stanfield, S., Corbin, D., and Helinski, D. R. (1980). Broad host range DNA cloning system for Gram-Negative bacteria: construction of a gene bank of Rhizobium meliloti. Proc Natl Acad Sci USA 77, 7347–7351.

Drahos, D., Barry, G., Hemming, B., Brandt, F., Skipper, H., Kline, E., Kluepful, D., Hughes, T., and Gooden, D., in The Release of Genetically-Engineered Microorganisms. (1988). Sussman, M., Collins, C., Skinner, F. and Stewart-Tull, D. eds. Academic Press, New York.

Fling, M. E., Kopf, J., and Richards, C. (1985). Nucleotide sequence of the transposon Tn7 gene encoding an aminoglycoside-modifying enzyme, 3"(9)-O-nucleotidyl-transferase. Nucleic Acids Research 13 no.19, 7095–7106.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L., and Woo, S. C. (1983). Expression of bacterial genes in plant cells. Proc Natl Acad Sci USA 80, 4803–4807.

Fraley, R. T., Rogers, S. G., Horsch, R. B., Eichholtz, D. A., Flick, J. S., Fink, C. L., Hoffmann, N. L., and Sanders, P. R. (1985). The SEV system: a new disarmed Ti plasmid vector system for plant transformation. Biotechnology 3, 629–635.

Hamilton, A., Lycett, G. and Grierson, D. (1990). Antisense gene that inhibits synthesis of the hormone ethylene in transgenic plants. Nature 346:284–287.

Hohn, B. and Collins J. (1980) A small cosmid for efficient cloning of large DNA fragments. Gene 11: 291–298.

Holdsworth, M. Schuch, W. and Grierson, D. (1987). Nucleotide sequence of an ethylene-related gene from tomato. Nucleic Acids Res. 15:10600

Honma, M. and Shimomura, T. (1978). Metabolism of 1-Aminocyctopropane-1-carboxylic Acid. Agric, Biol. Chem. 42(10), pp 1825–1831.

Kay, R., Chan, A., Daly, M., and McPherson, J. (1987). Duplication of the CaMV 35S promoter sequence creates a strong enhancer for plants. Science 236, 1299–1302.

Klein, T. M., Wold, E. D., Wu, R. and Sanford, J. C. (1987) Nature 327:70–73.

Koncz, C., and Schell, J. (1986). The promoter of TL-DNA gene 5 controls the tissue-specific expression of chimeric genes carried by novel type of Agrobacterium binary vector. Mol Gen Genet 204, 383–396.

Lincoln, J. and Fischer, R. (1988). Diverse mechanisms for the regulation of ethylene-inducible gene expression. Mol Gen Genet 212, 71–75.

McCabe, D. E., et al. (1988) Bio/Technology 6:923.

Miller, J. H. (1972). Experiments in Molecular Genetics. Cold Spring Harbor Laboratory, Cold Spring Harbor, N.Y.

Miller, L. T. (1982). Single derivatization method for routine analysis of bacterial whole-cell fatty acid methyl esters, including hydroxy acids. J. Clinical Microbiology 16:584–586.

Morelli, G., Nagy, F., Fraley, R. T., Rogers, S. G., and Chua, N. H. (1985). A short conserved sequence is involved in the light-inducibility of a gene encoding ribulose 1,5-bisphosphate carboxylase small subunit of pea. Nature 315, 200–204.

Neuhaus, G. et al. (1987) Theor. Appl. Genet. 75:30.

Odell, J. T., Nagy, F., and Chua, N. H. (1985). Identification of DNA sequences required for activity of the cauliflower mosaic virus 35S promoter. Nature 313, 810–812.

Sambrook, J., Fritsch, E. F., and Maniatis, T. (1989) Molecular Cloning: A Laboratory Manual—second edition. Cold Spring Harbor Laboratory Press, Cold Spring Harbor, N.Y.

Stalker, D. M., Thomas, C. M., and Helinski, D. R. (1981). Nucleotide sequence of the region of the origin of replication of the broad host range plasmid RK2.Mol Gen Genet 181, 8–12.

Tabor, S., and Richardson, C. C. (1985). A bacteriophage T7 RNA polymerase/promoter system for controlled expression of specific genes. Proc. Natl. Acad. Sci. USA 82, 1074–1078.

Tabor, C. and Tabor H. 1987. The speEspeD operon of *E. coli*. J. Biol. Chem. 262:16037–16040.

Talmadge, K., and Gilbert, W., "Construction of plasmid vectors with unique PstI cloning sites in the signal sequence coding region" Gene, (12) 235–241 (1980).

Van Der Straeten, D., Van Wiemeersch, L., Goodman, H. and Van Montagu, M. (1990) Proc. Natl. Acad. Sci. USA 87:4859–4863.

Vieira, J. and Messing, J., Production of single-stranded plasmid DNA. Methods. Enzymol. 153: 3 (1987).

Ward, T., Wright, M., Roberts, J., Self, R., and Osborne, D. (1978) Analytical procedures for the assay and identification of ethylene. In Isolation of plant growth substances, J. Hillman, ed. (Cambridge: Cambridge University Press), pp. 135–151.

We claim:

1. A recombinant, double-stranded DNA molecule which functions in tomato plants to delay ripening of tomato fruit by causing a reduction of ethylene biosynthesis, said molecule comprising in sequence in the 5' to 3' direction:

(i) a promoter region which functions in ripening tomato fruit to cause the production of an RNA sequence, said promoter region operably linked to;

(ii) a structural DNA sequence that causes the production of an RNA sequence that encodes a 1-aminocyclopropane-1-carboxylic acid deaminase enzyme, said structural sequence operably-linked to;

(iii) a 3' non-translated region that functions in plant cells to polyadenylate the 3' end of said RNA sequence;

wherein said promoter is heterologous with respect to said structural DNA sequence.

2. A method for producing tomatoes which exhibit a delayed-ripening phenotype which comprises:

a) obtaining regenerable cells of a tomato plant;

b) transforming said cells by inserting into the genome of said cells a recombinant, double-stranded DNA molecule which causes a reduction of ethylene biosynthesis, said molecule comprising in sequence in the 5' to 3' direction:

(i) a promoter region which functions in ripening tomato fruit to cause the production of an RNA sequence, said promoter region operably linked to;

(ii) a structural DNA sequence that causes the production of an RNA sequence that encodes a 1-aminocyclopropane-1-carboxylic acid deaminase enzyme, said structural sequence operably-linked to;

(iii) a 3' non-translated region that functions in plant cells to polyadenylate the 3' end of said RNA sequence, wherein said promoter is heterologous with respect to said structural DNA sequence;

c) regenerating a tomato plant from the transformed tomato plant cell; and d) growing said transformed tomato plant to produce tomatoes which demonstrate delayed ripening.

3. A transgenic tomato plant which exhibits a delayed-ripening phenotype, said plant comprising a recombinant, double-stranded DNA molecule which causes a reduction of ethylene biosynthesis, said molecule comprising in sequence in the 5' to 3' direction:

(i) a promoter region that causes the production of an RNA sequence in ripening tomato fruit, said promoter region operably-linked to;

(ii) a structural DNA sequence that causes the production of an RNA sequence that encodes a 1-aminocyclopropane-1-carboxylic acid deaminase enzyme, said structural sequence operably-linked to;

(iii) a 3' non-translated region that functions in plant cells to polyadenylate the 3' end of said RNA sequence;

wherein said promoter is heterologous with respect to said structural DNA sequence.

4. A transgenic tomato fruit which exhibits a delayed-ripening phenotype, said tomato comprising a recombinant, double-stranded DNA molecule which causes a reduction of ethylene biosynthesis, said molecule comprising in sequence in the 5' to 3' direction:

(i) a promoter region that causes the production of an RNA sequence in ripening tomato fruit, said promoter region operably-linked to;

(ii) a structural DNA sequence that causes the production of an RNA sequence that encodes a 1-aminocyclopropane-1-carboxylic acid deaminase enzyme, said structural sequence operably-linked to;

(iii) a 3' non-translated region that functions in plant cells to polyadenylate the 3' end of said RNA sequence;

wherein said promoter is heterologous with respect to said structural DNA sequence.

5. A recombinant, double-stranded DNA molecule of claim 1 in which the promoter is selected from the group consisting of the CaMV35S, FMV35S, 2A11 and E8 promoters.

6. A method of claim 2 in which the promoter is selected from the group consisting of the CaMV35S, FMV35S, 2A11 and E8 promoters.

7. A transgenic tomato plant of claim 3 in which the promoter is selected from the group consisting of the CaMV35S, FMV35S, 2A11 and E8 promoters.

8. A transgenic tomato fruit of claim 4 in which the promoter is selected from the group consisting of the CaMV35S, FMV35S, 2A11 and E8 promoters.

9. A recombinant, double-stranded DNA molecule of claim 5 in which the structural DNA encodes the protein encoded by SEQ ID NO: 1 and the promoter is selected from the group consisting of the CaMV35S, FMV35S, and E8 promoters.

10. A method of claim 6 in which the structural DNA encodes the protein encoded by SEQ ID NO: 1 and the promoter is selected from the group consisting of the CaMV35S, FMV35S, and E8 promoters.

11. A transgenic tomato plant of claim 7 in which the structural DNA encodes the protein encoded by SEQ ID NO: 1 and the promoter is selected from the group consisting of the CaMV35S, FMV35S, and E8 promoters.

12. A transgenic tomato fruit of claim 8 in which the structural DNA encodes the protein encoded by SEQ ID NO: 1 and the promoter is selected from the group consisting of the CaMV35S, FMV35S, and E8 promoters.

13. A recombinant, double-stranded DNA molecule of claim 9 in which the structural DNA is SEQ ID NO: 1.

14. A method of claim 10 in which the structural DNA is SEQ ID NO: 1.

15. A transgenic tomato plant of claim 11 in which the structural DNA is SEQ ID NO: 1.

16. A transgenic tomato fruit of claim 12 in which the structural DNA is SEQ ID NO: 1.

17. A recombinant, double-stranded DNA molecule of claim 5 in which the promoter is a CaMV35S promoter.

18. A method of claim 6 in which the promoter is a CaMV35S promoter.

19. A transgenic tomato plant of claim 7 in which the promoter is a CaMV35S promoter.

20. A transgenic tomato fruit of claim 8 in which the promoter is a CaMV35S promoter.

21. A recombinant, double-stranded DNA molecule which functions in tomato to delay ripening of tomato fruit, said molecule comprising in sequence in the 5' to 3' direction:
(i) a CaMV 35S promoter region, said promoter region operably linked to;
(ii) a structural DNA sequence that encodes the protein encoded by SEQ ID NO. 1, said structural sequence operably-linked to;
(iii) a 3' non-translated region that functions in plant cells to polyadenylate the 3' end of said RNA sequence.

22. A method for producing tomatoes which have a delayed-ripening phenotype which comprises:
a) obtaining regenerable cells of a tomato plant;
b) transforming said cells by inserting into the genome of said cells a recombinant, double-stranded DNA molecule capable of causing a reduction of ethylene biosynthesis, said molecule comprising in sequence in the 5' to 3' direction:
(i) a CaMV 35S promoter region, said promoter region operably linked to;
(ii) a structural DNA sequence that encodes the protein encoded by SEQ ID NO. 1, said structural sequence operably-linked to;
(iii) a 3' non-translated region that functions in plant cells to polyadenylate the 3' end of said RNA sequence;
c) regenerating a tomato plant from said transformed tomato plant cell; and
d) growing said transformed tomato plant to produce tomatoes which have a delayed ripening phenotype.

23. A transgenic tomato plant which exhibits a delayed-ripening phenotype, said plant comprising a recombinant, double-stranded DNA molecule which causes a reduction of ethylene biosynthesis, said molecule comprising in sequence in the 5' to 3' direction:
(i) a CaMV 35S promoter region, said promoter region operably linked to;
(ii) a structural DNA sequence that encodes the protein encoded by SEQ ID NO. 1, said structural sequence operably-linked to;
(iii) a 3' non-translated region that functions in plant cells to polyadenylate the 3' end of said RNA sequence.

24. A transgenic tomato fruit which exhibits a delayed-ripening phenotype, said tomato comprising a recombinant, double-stranded DNA molecule which causes a reduction of ethylene biosynthesis, said molecule comprising in sequence in the 5' to 3' direction:
(i) a CaMV 35S promoter region, said promoter region operably linked to;
(ii) a structural DNA sequence that encodes the protein encoded by SEQ ID NO. 1, said structural sequence operably-linked to;
(iii) a 3' non-translated region that functions in plant cells to polyadenylate the 3' end of said RNA sequence.

25. A recombinant, double-stranded DNA molecule of claim 21 in which the structural DNA is SEQ ID NO: 1.

26. A method of claim 22 in which the structural DNA is SEQ ID NO: 1.

27. A transgenic tomato plant of claim 23 in which the structural DNA is SEQ ID NO: 1.

28. A transgenic tomato fruit of claim 24 in which the structural DNA is SEQ ID NO: 1.

* * * * *